(12) United States Patent
Lv et al.

(10) Patent No.: US 12,377,151 B2
(45) Date of Patent: *Aug. 5, 2025

(54) IMMOBILIZED ENDOGLYCOSIDASE FUSION PROTEIN AND USE THEREOF

(71) Applicant: GENEQUANTUM HEALTHCARE (SUZHOU) CO., LTD., Suzhou (CN)

(72) Inventors: Cao Lv, Suzhou (CN); Jinduo Yuan, Suzhou (CN); Gang Qin, Suzhou (CN); Meijun Xiong, Suzhou (CN)

(73) Assignee: GENEQUANTUM HEALTHCARE (SUZHOU) CO., LTD., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/787,110

(22) Filed: Jul. 29, 2024

(65) Prior Publication Data
US 2024/0398960 A1 Dec. 5, 2024

Related U.S. Application Data

(63) Continuation of application No. PCT/CN2023/104549, filed on Jun. 30, 2023.

(30) Foreign Application Priority Data

Jul. 1, 2022 (CN) .......................... 202210774352.7
Mar. 15, 2023 (CN) .......................... 202310251354.2

(51) Int. Cl.
*A61K 47/54* (2017.01)
*A61K 47/22* (2006.01)
(Continued)

(52) U.S. Cl.
CPC ............ *A61K 47/549* (2017.08); *A61K 47/22* (2013.01); *A61K 47/26* (2013.01); *A61K 47/545* (2017.08);
(Continued)

(58) Field of Classification Search
None
See application file for complete search history.

(56) References Cited

U.S. PATENT DOCUMENTS

| 9,175,326 B2 | 11/2015 | Wang |
| 9,850,473 B2 | 12/2017 | Wang |

(Continued)

FOREIGN PATENT DOCUMENTS

| CN | 104220603 A | 12/2014 |
| CN | 109071630 A | 12/2018 |

(Continued)

OTHER PUBLICATIONS

Zhang et al., ACS Chem. Biol. 2021, 16, 2502-2514 (Year: 2021).*

(Continued)

*Primary Examiner* — Karl J Puttlitz
(74) *Attorney, Agent, or Firm* — Hoxie & Associates LLC

(57) ABSTRACT

A method for preparing an antibody-drug conjugate. The antibody-drug conjugate is formed by means of site-directed conjugation on the basis of an N-glycosylation site of an Fc region of an antibody. The method comprises: (1) providing a donor containing an oxazoline oligosaccharide, an antibody containing a GlcNAc motif, and an immobilized endoglycosidase having a glycoside transfer activity; and (2) covalently linking the activated donor containing the oxazoline oligosaccharide to the antibody containing the GlcNAc motif by means of the catalytic action of the endoglycosidase; therefore, one-step conjugation is realized. The present invention also relates to an endoglycosidase fusion protein, which comprises a covalently linked endoglycosidase, a Halo tag, and/or a His tag. The present invention also relates to an immobilized endoglycosidase fusion protein obtained by means of immobilizing an endoglycosidase fusion protein on a support, a prepacked column filled with the immobilized fusion protein, and a method for (Continued)

purifying an antibody conjugate by using the immobilized endoglycosidase fusion protein.

17 Claims, 14 Drawing Sheets

Specification includes a Sequence Listing.

(51) Int. Cl.
  *A61K 47/26* (2006.01)
  *A61K 47/68* (2017.01)
  *C12N 9/24* (2006.01)
(52) U.S. Cl.
  CPC ............ *A61K 47/68* (2017.08); *C12N 9/2402* (2013.01); *C07K 2317/41* (2013.01); *C07K 2317/52* (2013.01)

(56) References Cited

U.S. PATENT DOCUMENTS

| | | |
|---|---|---|
| 9,884,123 B2 | 2/2018 | Sengupta et al. |
| 10,836,815 B2 | 11/2020 | Wang et al. |
| 10,851,174 B2 | 12/2020 | Wang et al. |
| 11,459,380 B2 | 10/2022 | Wang et al. |
| 11,559,581 B2 | 1/2023 | Davis et al. |
| 11,643,450 B2 | 5/2023 | Wang et al. |
| 11,834,688 B2 | 12/2023 | Qin et al. |
| 11,845,970 B2 | 12/2023 | Wang et al. |
| 12,012,582 B2 | 6/2024 | Qin et al. |
| 2012/0226024 A1 | 9/2012 | Wang et al. |
| 2020/0323995 A1 | 10/2020 | Satomaa et al. |
| 2023/0355791 A1 | 11/2023 | Van Delft et al. |
| 2024/0082419 A1 | 3/2024 | Qin et al. |
| 2024/0197900 A1 | 6/2024 | Huang et al. |

FOREIGN PATENT DOCUMENTS

| | | | |
|---|---|---|---|
| CN | 114395051 A | 4/2022 | |
| CN | 114480115 A | 5/2022 | |
| WO | WO-2007133855 A2 * | 11/2007 | ............. C07K 16/00 |
| WO | 2013/120066 A1 | 8/2013 | |
| WO | 2018/036403 A1 | 3/2018 | |
| WO | 2018/039373 A1 | 3/2018 | |
| WO | 2020/006176 A1 | 1/2020 | |
| WO | 2022/174834 A1 | 8/2022 | |
| WO | 2022/226420 A2 | 10/2022 | |
| WO | 2023/232144 A1 | 12/2023 | |

OTHER PUBLICATIONS

Wang et al., J. Am. Chem. Soc. 2008, 130, 13790 (Year: 2008).*
Davis et al., J. Am. Chem. Soc. 2012, 134, 8030 (Year: 2012).*
Huang et al., J. Am. Chem. Soc. 2012, 134, 12308 (Year: 2012).*
Li et al., Carbohydrate Research 458-459 (2018) 77e84 (Year: 2018).*
J. Döbber, et al., Journal of Biotechnology 241 (2017) 170-174 (Year: 2017).*
Parsons et al., Angew. Chem. Int. Ed. 2016, 55, 2361-2367 (Year: 2016).*
Boeggeman, E. et al. "Site specific conjugation of fluoroprobes to the remodeled Fc N-glycans of monoclonal antibodies using mutant glycosyltransferases: Application for cell surface antigen detection," Bioconjug Chem., vol. 20, No. 6, pp. 1228-1236, (2009).
Chuang, H. et al. "Development of biotinylated and magnetic bead-immobilized enzymes for efficient glyco-engineering and isolation of antibodies," Bioorganic Chemistry, vol. 112, (2021), Abstract Only, DOI: 10.1016/j.bioorg.2021.104863.
Danishefsky, I. et al. "Investigations on the Chemistry Heparin V. Disaccharides Obtained after Partial Hydrolysis," Bioconjugate Chemistry, vol. 101, No. 1, pp. 37-45, (1965).
Dickgiesser, S. et al. "Site-Specific Conjugation of Native Antibodies Using Engineered Microbial Transglutaminases," Bioconjugate Chemistry, vol. 31, No. 4, pp. 1070-1076, (2020).
English language machine translation for WO 2018/036403 A1, retrieved from WIPO on May 20, 2024, 34 pages.
Huang, W. et al. "Chemoenzymatic Glycoengineering of Intact IgG Antibodies for Gain of Functions," J Am Chem Soc., vol. 134, No. 29, pp. 12308-12318, (2012).
Li, X., et al. "Preparation of well-defined antibody-drug conjugates through glycan remodeling and strain-promoted azide-alkyne cycloadditions," Angew Chem Int Ed Engl., vol. 53, No. 28, pp. 7179-7182, (2014).
Shi, W. et al. "One-step synthesis of site-specific antibody-drug conjugates by reprograming IgG glycoengineering with LacNAc-based substrates," Acta Phamaceutica Sinica. B, vol. 12, No. 5, pp. 2417-2428, (2022), DOI: 10.1016/j.apsb.2021.12.013.
Van Geel, R. et al. "Chemoenzymatic Conjugation of Toxic Payloads to the Globally Conserved N-Glycan of Native mAbs Provides Homogeneous and Highly Efficacious Antibody-Drug Conjugates," Bioconjug Chem., vol. 26, No. 11, pp. 2233-2242, (2015).
Wang, L. et al., "Glycoengineering of Antibodies for Modulating Functions," Annu Rev Biochem, vol. 88, pp. 433-459, (2019).
Zang, X. et al. "Synthesis and Evaluation of Three Azide-Modified Disaccharide Oxazolines as Enzyme Substrates for Single-Step Fc Glycan-Mediated Antibody-Drug Conjugation," Bioconjugate Chemistry, vol. 33, No. 6, pp. 1179-1191, (2022).
Zeng, Y. et al. "Recent advances in synthetic glycoengineering for biological applications," Curr Opin Biotechnol., vol. 74, pp. 247-255, (2022).
Zhang, X. et al. "General and Robust Chemoenzymatic Method for Glycan-Mediated Site-Specific Labeling and Conjugation of Antibodies: Facile Synthesis of Homogeneous Antibody-Drug Conjugates," ACS Chem Biol., vol. 16, No. 11, pp. 2502-2514, (2021).
Zhou, Q. et al. "Site-specific antibody-drug conjugation through glycoengineering," Bioconjug Chem., vol. 25, No. 3, pp. 510-520, (2014).
Zhu, Z. et al. "Site-specific antibody-drug conjugation through an engineered glycotransferase and a chemically reactive sugar," MAbs, vol. 6, No. 5, pp. 1190-1200, (2014).
Zuberbühler, K. et al. "Fucose-specific conjugation of hydrazide derivatives to a vascular-targeting monoclonal antibody in IgG format," Chem Commun, vol. 48, pp. 7100-7102, (2012).
Zhang, X., et al. "Synthesis and Evaluation of Three Azide-Modified Disaccharide Oxazolines as Enzyme Substrates for Single-Step Fc Glycan-Mediated Antibody-Drug Conjugation," HHS Public Access, Author manuscript, available in PMC 2023, 25 pages, front page states: Published in final edited form as: Bioconjug Chem. Jun. 15, 2022; 33(6): 1179-1191. doi:10.1021/acs.bioconjchem. 2c00142.

* cited by examiner

IMMOBILIZED ENDOGLYCOSIDASE FUSION PROTEIN AND USE THEREOF

CROSS REFERENCE TO RELATED APPLICATIONS

This application claims priority to and is a continuation of International Application No. PCT/CN2023/104549, filed on Jun. 30, 2023, which claims priority to and the benefit of Chinese Patent Application No. 202310251354.2, filed on Mar. 15, 2023, and Chinese Patent Application No. 202210774352.7, filed on Jul. 1, 2022, the disclosures of which are incorporated herein by reference in its entirety

REFERENCE TO A SEQUENCE LISTING

This application contains a Sequence Listing as a separate part of the disclosure. The contents of the Sequence Listing (2024-07-29-GQH-19-PCTC-Sequence Listing.xml; Size 12,922 bytes; and Date of Creation: Jul. 29, 2024) are incorporated herein by reference.

TECHNICAL FIELD

The present disclosure relates to the field of biotechnology, in particular to a method for preparing a drug conjugate or an antibody-drug conjugate by using immobilized endoglycosidase fusion protein with glycoside transfer activity, where the antibody-drug conjugate is subjected to one-step site-specific conjugation, based on an N-glycosylation site in an Fc region of the antibody. The present disclosure further relates to an endoglycosidase fusion protein including endoglycosidase, a Halo tag and/or a His tag that are covalently attached, and an immobilized endoglycosidase fusion protein obtained by immobilizing the endoglycosidase fusion protein on a support.

BACKGROUND

Demands for high-quality conjugates, especially bioconjugates, such as those for bioscience research, diagnosis or therapeutics purposes, are increasing rapidly. However, the high-quality stable production of the bioconjugates is far from satisfying, partially because that the complex nature of biomolecules and scale-up difficulty make the high-quality standards for bioconjugates difficult to be met.

Antibody-drug conjugates (ADCs) are a type of novel targeted drug included in the category of bioconjugates, in which highly active small molecule drugs are connected with monoclonal antibodies via chemical linking. Therefore, the antibody-drug conjugate has both the high activity of a small molecule drug and the targeting property of an antibody drug. The ADC can overcome toxic and side effects of small molecule toxins on the human body better, and meanwhile, overcome the limitation of the therapeutic effect of an antibody therapy on solid tumors, and thus, it become a type of anti-tumor drugs with great development prospects.

With the development and gradual maturity of the ADCs, an antibody conjugation technology has evolved through several iterative upgrades, and has roughly evolved through three generations: random conjugation, antibody gene engineering-based site-specific conjugation, and antibody gene engineering-independent site-specific conjugation (Walsh S J, Bargh J D, Dannheim F M, et al., Site-selective modification strategies in antibody-drug conjugates, Chem. Soc. Rev. 2021, 50, 1305-1353). According to the first generation of conjugation technology, lysine or cysteine residue-based random conjugation is mainly employed, which generally results in a highly heterogeneous mixture with random conjugation sites and an inhomogeneous drug/antibody ratio (DAR). As a result, it is prone to problems in process stability, quality control, drug stability, metabolic consistency, safety, etc. According to the second generation of conjugation technology, it is usually necessary to introduce a specific amino acid into an antibody or insert a polypeptide fragment of a specific sequences through engineering mutation. On this basis, site-specific conjugation of the antibody is achieved through site-specific chemical conjugation or enzymatic conjugation. According to the third generation of conjugation technology, engineering of an antibody is not needed, and it is focused on performing site-specific conjugation by selecting specific amino acid sites and utilizing specific conditions or a proximity effect, including modification of interchain disulfide bonds, chemical selectivity modification, proximity effect-based modification, and glycosyl modification. By comprehensive comparison, the glycosyl modification has become a research focus of the antibody conjugation technology due to its advantages, such as no need of the engineering of the antibody, no changes in core skeleton structure of antibody, no effect on the binding ability of an antigen-binding region of the antibody, no need of fine adjustment of chemical reaction conditions, good conjugation repeatability and homogeneity, etc. Highly conserved glycosylation is found in asparagine at position 297 in an Fc region of the antibody (N-297 Glycan). Site-specific attachment of different molecules on the antibody can be achieved by the glycan chain remodeling at this site (Wang L X, Tong X, Li C. Glycoengineering of Antibodies for Modulating Functions, Annu Rev Biochem, 2019, 88, 433-459). Site-specific conjugation technologies based on antibody Fc glycosyl modification mainly include:

1) glycosyl-based chemical modification: using sodium periodate to oxidize core fucose (Zuberbuhler K, Casi G, Bernardes G J et al., Fucose-specific conjugation of hydrazide derivatives to a vascular-targeting monoclonal antibody in IgG format, Chem Commun, 2012, 48, 7100-7102) or o-diol in sialic acid at the end of the glycosyl (Zhou Q, Stefano J E, Manning C et al., Site-specific antibody-drug conjugation through glycoengineering, Bioconjugate Chem, 2014, 25, 510-520) to obtain corresponding aldehydes, and aldehydic carbonyl can be conjugated with small molecule toxin fragments to prepare ADCs. Such methods, due to the diversity of glycosyl structures at N-297 site, and not all monoclonal antibody glycosyls contain reactive sites of core fucose or sialic acid, have certain limitations to substrates.

2) enzymatic catalysis-based modification: using deglycosylation-transglycosylation tandem catalysis with tool enzymes such as endoglycosidase and glycosyltransferase to achieve glycan chain remodeling to introduce a biologically orthogonal reactive group, and then site-specific conjugation preparation of ADCs is achieved through subsequent chemical reactions (Wang L X, Tong X, Li C, Glycoengineering of antibodies for modulating functions, Annu Rev Biochem, 2019, 88, 433-459; and Zeng Y, Tang F, Shi W et al., Recent advances in synthetic glycoengineering for biological applications, Current Opinion in Biotechnol, 2022, 74, 247-255).

In 2012, Wang Laixi et al. reported site-specific conjugation technology of antibody glycan chain remodeling based on the tandem catalysis of endoglycosidase Endo S and its mutant, synthesizing a glycan chain remodeled antibody with a single glycoform structure and containing azido modifications (Huang W, Giddens J, Fan S Q et al., Chemoenzymatic glycoengineering of intact IgG antibodies for gain of functions, *J. Am. Chem. Soc.*, 2012, 134, 12308). Base on this work, Wang Laixi and Huang Wei et al. have developed a large type of ADC site-specific conjugation synthesis technologies, in which deglycosylation-transglycosylation-click chemistry three-step process was involved, based on the tandem catalysis of tool enzymes such as endoglycosidase Endo S or Endo S2 and their mutants (Zeng Y, Tang F, Shi W, et al., Recent advances in synthetic glycoengineering for biological applications, *Current Opinion in Biotechnol*, 2022, 1074, 247-255). In 2021, Wang Laixi et al. reported Endo S2-catalyzed site-specific conjugation of antibody glycan chain remodeling in a one-pot manner, where a bioorthogonal azide functional group is introduced to the antibody, and then ADC molecules are obtained after a click reaction step (Zhang X, Ou C, Liu H, et al., General and robust chemoenzymatic method for glycan-mediated site-specific labeling and conjugation of antibodies: facile synthesis of homogeneous antibody-drug conjugates, *ACS Chem. Biol.*, 2021, 16, 11, 2502-2514).

Another type of commonly used tool enzymes in the site-specific conjugation technology of glycan chain remodeling is β-1,4-galactosyltransferase (β-1,4-Gal-T1) and its mutants (β-1,4-Gal-T1 Y289L). Uridine diphosphate galactose (Gal-UDP) is taken as a donor in this enzyme to transfer galactose (Gal) to a non-reducing end of acetylglucosamine (Glc-NAc) of glycoprotein. Based on this strategy, in 2009, Qasba et al. (Boeggeman E, Ramakrishnan B, Pasek M, et al., Site specific conjugation of fluoroprobes to the remodeled Fc N-glycans of monoclonal antibodies using mutant glycosyltransferases: application for cell surface antigen detection, *Bioconjugate Chem.*, 2009, 20, 6, 1228-1236) first reported a site-specific conjugation technology in which β-1,4-Gal-T1 and β-1,4-Gal-T1 Y289L were used as tool enzymes, and C2-keto-Gal-UDP or N-azidoacetylgalactosamine-UDP (GalNAz-UDP) as a donor, preparing Ketocarbonyl- or azido-modified antibodies. Subsequently, they reported a first ADC molecular synthesis method in 2014, in which three sequential steps including deglycosylation, transglycosylation and bioorthogonal reaction were involved, based on the catalysis of β-1,4-Gal-T1 and its mutant (Zhu Z, Ramakrishnan B, Li J, et al., Site-specific antibody-drug conjugation through an engineered glycotransferase and a chemically reactive sugar, mAbs, 2014, 6, 1190-1200). On the basis of the above work, a three-step ADC synthesis method involving deglycosylation-transglycosylation-bioorthogonal reaction process was developed by Synaffix via combined use of the tandem catalysis of tool enzymes endoglycosidases Endo S and β-1,4-Gal-T1 Y289L (Van Geel R, Wijdeven M A, Heesbeen R, et al., Chemoenzymatic conjugation of toxic payloads to the globally conserved N-glycan of native mAbs provides homogeneous and highly efficacious antibody-drug conjugates, *Bioconjugate Chem.*, 2015, 26, 2233-2242). Furthermore, a four-step synthesis method for ADCs through deglycosylation-transglycosylation-transglycosylation-bioorthogonal reaction process was reported in the literature (Li X, Fang T, Boons G J, Preparation of well-defined antibody-drug conjugates through glycan remodeling and strain-promoted azide-alkyne cycloadditions, *Angew. Chem. Int. Ed.*, 2014, 53, 7179-7182), and a total of three tool enzymes, β-1,4-Gal-T1, β-1,4-Gal-T1 Y289L and sialyltransferase, were used in this method.

For the above-mentioned conjugation technologies of glycan chain remodeling, liquid-phase enzyme-catalyzed multi-step reactions are utilized, which has certain limitations. For example, liquid-phase enzyme catalysis requires a large proportion of endoglycosidase catalytic equivalents, the requirement on enzyme purity is high (complex process and high preparation cost), and it is prone to introduction of a large number of enzyme related impurities (such as host proteins and nucleic acids) into a reaction system, which poses significant challenges for subsequent downstream removal of impurities from the drug conjugate.

At present, there are only a few publicly reported glycan chain conjugation reaction modes based on catalysis of immobilized enzymes. For example, in 2018, Wang Laixi et al. reported that deglycosylation-transglycosylation continuous flow tandem catalysis is achieved based on tandem column conjugation of a covalently immobilized Endo S2 enzyme and a covalently immobilized Endo S2 D184M enzyme to obtain glycosyl-modified glycan chain homogeneous antibodies (Li T, Li C, Quan D N, et al., Site-specific immobilization of endoglycosidases for streamlined chemoenzymatic glycan remodeling of antibodies, *Carbohydr. Res.* 2018, 458-459, 77-84). In 2021, Wu Zongyi et al. reported that glycosyl-modified glycan chain homogeneous antibodies are obtained by tandem catalysis with liquid-phase-suspended immobilized enzymes Endo S2 and Endo S2 T138Q (Chuang H, Huang C, Hung T, et al., Development of biotinylated and magnetic bead-immobilized enzymes for efficient glyco-engineering and isolation of antibodies, *Bioorg. Chem.* 2021, 112, 104863). There have been currently no reports on one-step preparation of the ADCs by glycan chain remodeling based on the catalysis of the immobilized enzymes. In summary, existing glycan chain remodeling reaction avoids the problem that antibodies need to be engineered in other site-specific conjugation technologies, but still with very big limitations. For example, the glycan chain remodeling reaction has lengthy conjugation steps and cumbersome operation, and at least two steps of enzymatic reaction and one step of chemical reaction are required. That is, at least three steps of reaction and three times of complete purification are required to obtain the ADCs. In another aspect, most of the existing glycan chain remodeling is based on liquid-phase enzyme-catalyzed reactions, which have problems such as scale-up difficulty, difficulty in isolation and removal of glycosidase, and great challenges in industrialization. According to literature reports, even residual trace amounts of tool enzymes in ADC products may cause deglycosylation of the ADC products to make toxin molecules shed (Li T, Li C, Quan D N, et al., Site-specific immobilization of endoglycosidases for streamlined chemoenzymatic glycan remodeling of antibodies, *Carbohydrate Research* 2018, 458-459, 77-84), which may cause serious toxic reactions, bring major challenges to drug development and production, and also bring major hidden dangers to the safety of the ADCs. The present disclosure aims to solve these problems.

SUMMARY

Antibody-drug conjugates can be conjugated based on site-specific conjugation technology of glycan chain remodeling. Highly conserved glycosylation is found in asparaginate at position 297 in an Fc region of an antibody. Site-specific conjugation of different molecules on the antibody can be achieved by glycan chain remodeling at this site. Proteins (such as an Fc fusion protein) containing the Fc region can also achieve, based on the asparagine at position 297 in the Fc region of the antibody, site-specific conjugation of different molecules, wherein the asparagine at position 297 in the protein containing the Fc region is localized in order of amino acids of the antibody.

In this application, an Fc-terminus glycan chain of the antibody is remodeled by an immobilized endoglycosidase with glycosyltransferase activity, and a linker-payload is efficiently and specifically conjugated to an Fc-containing protein or antibody by a suspended liquid-phase catalysis or column continuous flow catalysis process to obtain an antibody-drug conjugate with good homogeneity in one step.

In one aspect, the present disclosure provides a method for preparing a drug conjugate, wherein the drug conjugate is subjected to site-specific conjugation, based on an N-glycosylation site in an Fc region, and the method includes the steps of:
(1) providing a donor containing oxazoline oligosaccharide, a protein containing the Fc region, and an immobilized endoglycosidase with glycosyltransferase activity; wherein the Fc contains a GlcNAc motif; and
(2) covalently attaching the donor containing the oxazoline oligosaccharide to the protein containing the Fc region under the catalytic action of the endoglycosidase.

In some embodiments, the protein containing the Fc region is an antibody or an Fc fusion protein.

In one aspect, the present disclosure provides a method for preparing an antibody-drug conjugate, wherein the antibody-drug conjugate is subjected to site-specific conjugation, based on an N-glycosylation site in an Fc region of an antibody, and the method includes the steps of:
(1) providing a donor containing oxazoline oligosaccharide, an antibody containing a GlcNAc motif, and an immobilized endoglycosidase with glycosyltransferase activity;
(2) covalently attaching the activated donor containing the oxazoline oligosaccharide to the antibody containing the GlcNAc motif under the catalytic action of the endoglycosidase.

In some embodiments, the oxazoline oligosaccharide-containing donor further contains a payload. In some embodiments, the payload is selected from the group consisting of: a small molecule compound, an agonist, nucleic acid, a nucleic acid analog, a fluorescent molecule, a radionuclide, and an immunomodulatory protein (such as interleukin). In some embodiments, the payload is selected from the group consisting of: small molecule compounds (e.g., small molecule drugs with various mechanisms of action, including various traditional small molecule drugs, photoacoustic dynamic therapy drugs, photothermal therapy drugs, e.g., chemotherapy drugs, small molecule targeted drugs, immune agonists, and the like, e.g., traditional cytotoxic drugs such as cis-platinum, paclitaxel, 5-fluorouracil, cyclophosphamide and bendamustine; small molecule targeted drugs such as imatinib mesylate, gefitinib and anlotinib; immune agonists such as STING agonists and TLR agonists), nucleic acids and nucleic acid analogs, tracer molecules (including fluorescent molecules, biotin, fluorophores, chromophores, spin resonance probes, radioactive labels and the like), short peptides, polypeptides, peptidomimetics and proteins.

In some embodiments, the oxazoline oligosaccharide is selected from one or more in the group consisting of: disaccharide oxazoline, trisaccharide oxazoline, tetrasaccharide oxazoline, pentasaccharide oxazoline, hexasaccharide oxazoline, heptasaccharide oxazoline, octasaccharide oxazoline, nonasaccharide oxazoline, decasaccharide oxazoline, and undecasaccharide oxazoline. In some embodiments, the oxazoline oligosaccharide has the following structure:

first hexosyl or its derivative-(second hexosyl or its derivative)-β-D-glucopyranosyloxazoline, wherein f is 0, 1, 2, 3, 4, 5 or 6; the β-D-glucopyranosyloxazoline has the following structure:

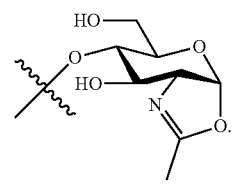

In some embodiments, the first hexosyl or its derivative is selected from the group consisting of: glucosyl, mannosyl, galactosyl, fructosyl, gulosyl, idosyl or their derivatives, and/or carbon at position 6 of the first hexosyl or its derivative is in the form —C(O)—; and/or the second hexosyl or its derivative, at each occurrence, is independently selected from the group consisting of: glucosyl, mannosyl, galactosyl, fructosyl or their derivatives; and/or individual monosaccharide moieties in the oligosaccharide structure are attached by β-(1→4) glycosidic bonds; and/or the derivatives (i.e., the first hexosyl derivative and the second hexosyl derivative) are independently selected from derivatives in which hydroxyl of uronic acid or monosaccharide is replaced by acylamino.

In some embodiments, the oxazoline oligosaccharide has the following structure:

first hexosyl or its derivative-β-D-glucopyranosyloxazoline, and wherein the first hexosyl or its derivative is mannitol (mannosyl) or its derivative.

In some embodiments, the oxazoline oligosaccharide has the following structure:

first hexosyl or its derivative-β-D-glucopyranosyloxazoline, and wherein the first hexosyl or its derivative is galactosyl or its derivative.

In some embodiments, the oxazoline oligosaccharide has the following structure:

first hexosyl or its derivative-β-D-glucopyranosyloxazoline, and wherein the first hexosyl or its derivative is glucosyl or its derivative; or the oxazoline oligosaccharide has the following structure: first hexosyl or its derivative-β-D-glucopyranosyloxazoline, and wherein the first hexosyl or its derivative is fructosyl or its derivative; or the oxazoline oligosaccharide has the following structure: first hexosyl or its derivative-β-D-glucopyranosyloxazoline, and wherein the first hexosyl or its derivative is gulosyl or its derivative; or the oxazoline oligosaccharide has the following structure: first hexosyl or its derivative-β-D-glucopyranosyloxazoline, and wherein the first hexosyl or its derivative is idosyl or its derivative.

In some embodiments, the oxazoline oligosaccharide has the following structure:

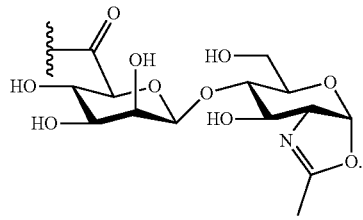

In some embodiments, the oxazoline oligosaccharide has the following structure:

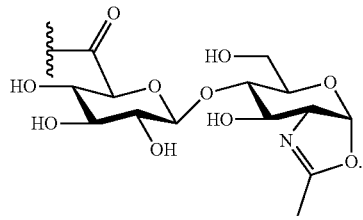

In one aspect, the present disclosure provides a method for preparing a drug conjugate, wherein the antibody-drug conjugate is subjected to site-specific conjugation, based on an N-glycosylation site in an Fc region, and the method includes the steps of:

(1) providing a donor containing oxazoline oligosaccharide, a protein containing the Fc region, and an immobilized endoglycosidase with glycosyltransferas activity, wherein the Fc comprises a GlcNAc motif;

wherein the donor containing the oxazoline oligosaccharide is a linker-payload compound of formula (I):

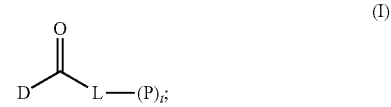

and (2) covalently attaching the donor containing the oxazoline oligosaccharide to the protein containing the Fc region under the catalysis of the endoglycosidase;

wherein the drug conjugate has a structure as shown in formula (II):

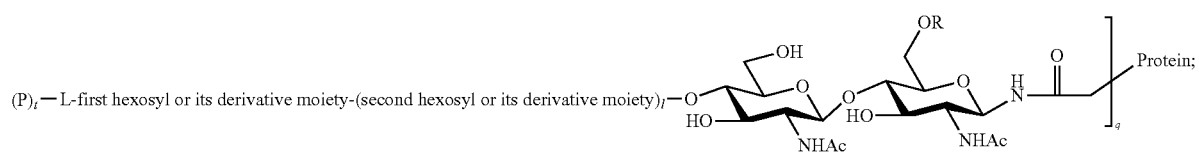

wherein P is a payload;

D-C(O)-L- is a linker;

carbon at position 6 of first hexosyl or its derivative moiety is in the form of —C(O)—, and f is 0, 1, 2, 3, 4, 5 or 6;

L is a linker end, and L is directly attached to carbonyl in D-C(O)— via —NH— therein, wherein when L is an unbranched linker end, L is attached to one P, and t is 1; while when L is a branched linker end, each branch can be attached to one P, and t is an integer greater than 1;

R is hydrogen or α-L-fucosyl;

q is 1 or 2; and

Protein is the protein containing the Fc region.

In some embodiments, -L-(P)t is shown in formula I-1 or formula I-2 below.

In some embodiments, the first hexosyl or its derivative is selected from glucosyl, mannosyl, galactosyl, fructosyl, gulosyl, idosyl or their derivatives; and/or the second hexosyl or its derivative, at each occurrence, is independently selected from glucosyl, mannosyl, galactosyl, fructosyl or their derivatives; and/or individual monosaccharide moieties in an oligosaccharide structure are attached by β-(1→4) glycosidic bonds; and/or the first hexosyl derivative and the second hexosyl derivative are independently selected from derivatives in which hydroxyl of uronic acid or monosaccharide is replaced by acylamino. In some embodiments, the protein containing the Fc region is an antibody or an Fc fusion protein.

In one aspect, the present disclosure provides a method for preparing an antibody-drug conjugate, wherein the antibody-drug conjugate is subjected to site-specific conjugation, based on an N-glycosylation site in an Fc region of an antibody, and the method includes the steps of:

(1) providing a donor containing oxazoline oligosaccharide, an antibody containing a GlcNAc motif, and an immobilized endoglycosidase with glycosyltransferase activity;

wherein the donor containing the oxazoline oligosaccharide is a linker-payload compound of formula (I):

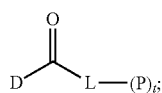

(I)

and (2) covalently attaching the donor containing the oxazoline oligosaccharide to the antibody containing the GlcNAc motif under the catalysis of the endoglycosidase;

wherein the antibody-drug conjugate has a structure as shown in formula (II-1), (II-2), (II-3), (II-4) or (II-5):

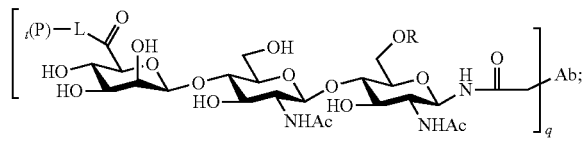

(II-1)

-continued

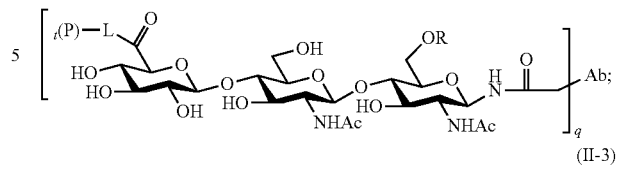

(II-2)

(II-3)

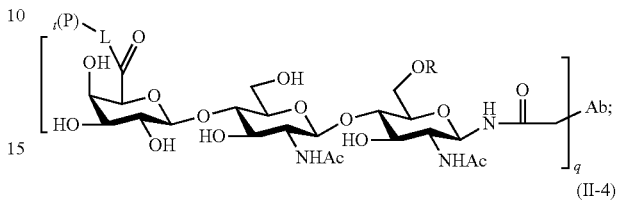

(II-4)

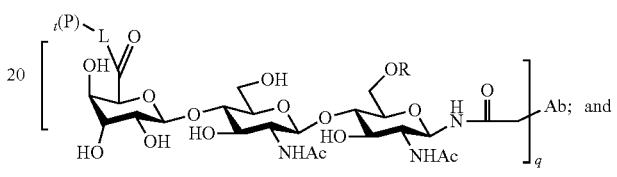

(II-5)

wherein P is a payload;

D-C(O)-L- is a linker;

D-C(O)— is a disaccharide structure;

L is a linker end, and L is directly attached to carbonyl in D-C(O)— via —NH— therein, wherein when L is an unbranched linker end, L is attached to one P, and t is 1; while when L is a branched linker end, each branch can be attached to one P, and t is an integer greater than 1;

R is hydrogen or α-L-fucosyl;

q is 1 or 2; and

Ab is an antibody or its antigen-binding fragment.

In one aspect, the present disclosure provides a method for preparing an antibody-drug conjugate, wherein the antibody-drug conjugate is subjected to site-specific conjugation, based on an N-glycosylation site in an Fc region of an antibody, and the method includes the steps of:

(1) providing a donor containing oxazoline oligosaccharide, an antibody containing a GlcNAc motif, and an immobilized endoglycosidase with glycosyltransferase activity;

wherein the donor containing the oxazoline oligosaccharide is a linker-payload compound of formula (I):

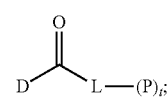

(I)

and (2) covalently attaching the donor containing the oxazoline oligosaccharide to the antibody containing the GlcNAc motif under the catalysis of the endoglycosidase;

wherein the antibody-drug conjugate has a structure as shown in formula (II):

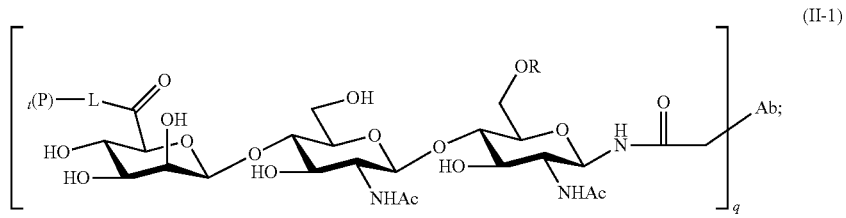

(II-1)

wherein P is a payload;
D-C(O)-L- is a linker;
D-C(O)— is a disaccharide structure

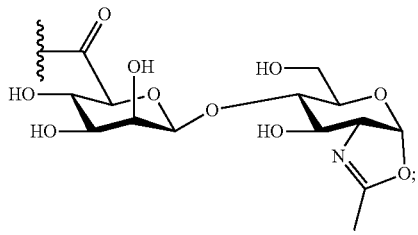

L is a linker end, and L is directly attached to carbonyl in D-C(O)— via —NH— therein, where when L is an unbranched linker end, L is attached to one P, and t is 1; while when L is a branched linker end, each branch can be attached to one P, and t is an integer greater than 1;
R is hydrogen or α-L-fucosyl;
q is 1 or 2; and
Ab is an antibody or its antigen-binding fragment.
In some embodiments, -L-(P)$_t$ in formula (I) is -L$^2$-L$^1$-B-P, wherein formula (I) is:

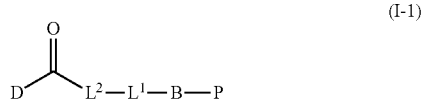

(I-1)

wherein
B is independently absent, or is 1) below, or 2) below, or a combination of 1) and 2) below: 1) a self-immolative spacer Sp1; 2) a divalent group, or a combination of two or more divalent groups, wherein the divalent group is selected from: —CR$^1$R$^2$—, C$_{1-10}$ alkylene, C$_{4-10}$ cycloalkylene, C$_{4-10}$ heterocyclylene and —(CO)—;
L$^1$ is independently absent, or is an uncleavable sequence; or is a cleavable sequence including an amino acid sequence that is enzymatically cleavable, and the amino acid sequence that is enzymatically cleavable includes 1, 2, 3, 4, 5, 6, 7, 8, 9 or 10 amino acids;
L$^2$ is independently absent; or is 1) below; or 2) below; or a combination of 1) and 2) below:
1) —NH—C$_{2-20}$ alkylene, wherein one or more —CH$_2$— structures in the alkylene are optionally replaced by the following groups: —CR$^3$R$^4$—, —O—, —(CO)—, —S—, —S(=O)$_2$—, —NR$^5$—, —N$^{\oplus}$R$^6$R$^7$—, C$_{4-10}$ cycloalkylene, C$_{4-10}$ heterocyclylene and phenylene, wherein the cycloalkylene, the heterocyclylene and the phenylene are each independently unsubstituted or substituted with at least one substituent selected from halogen, —C$_{1-10}$ alkyl, —C$_{1-10}$ haloalkyl, —C$_{1-10}$ alkylene-NH—R$^8$ and —C$_{1-10}$ alkylene-O—R$^9$;
2) an amino acid residue sequence, i.e., -*(AA)$_n$**-, wherein n is an integer from 1, 2, 3, 4, 5, 6, 7, 8, 9 or 10 to 100, AA, at each occurrence, is independently an amino acid residue, * represents an N-terminus of a corresponding amino acid and ** represents a C-terminus of the corresponding amino acid, and —(C$_2$H$_4$—O)$_m$—(CH$_2$)$_p$— is optionally present between amino and α-carbon of an amino acid, wherein m is 1, 2, 3, 4, 5, 6, 7, 8, 9 or 10; p is 0, 1, 2 or 3, and the * terminus forms an amide bond with the carbonyl in the disaccharide structure;
R$^1$, R$^2$, R$^3$, R$^4$, R$^5$, R$^6$, R$^7$, R$^8$ and R$^9$ are each independently selected from hydrogen, halogen, substituted or unsubstituted —C$_{1-10}$ alkyl, and C$_{4-10}$ cycloalkylene; or R$^1$ and R$^2$ and carbon atoms attached thereto together form a 3 to 6-membered cycloalkylene, and/or R$^3$ and R$^4$ and carbon atoms attached thereto together form a 3 to 6-membered cycloalkylene;
P is a payload attached to moiety B, or moiety L$^1$, or moiety L$^2$.

In one aspect, the present disclosure provides a method for preparing an antibody-drug conjugate, wherein the antibody-drug conjugate is subjected to site-specific conjugation, based on an N-glycosylation site in an Fc region of an antibody, and the method includes the steps of:
(I) providing a linker-payload compound of formula (I), an antibody, and an immobilized endoglycosidase with glycosyltransferase activity:

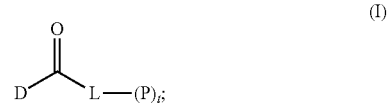

(I)

the antibody-drug conjugate is formed under the catalysis of the endoglycosidase;
wherein P is a payload;
D-C(O)-L- is a linker;
D-C(O)— is disaccharide oxazoline, which has the following structure:
first hexosyl or its derivative-β-D-glucopyranosyloxazoline, and wherein the first hexosyl or its derivative is galactosyl or its derivative;
L is a linker end, and L is directly attached to carbonyl in D-C(O)— via —NH— therein, wherein when L is an unbranched linker end, L is attached to one P, and t is 1; while when L is a branched linker end, each branch can be attached to one P, and t is an integer greater than 1;

R is hydrogen or α-L-fucosyl;

q is 1 or 2; and

Ab is an antibody or its antigen-binding fragment.

In some embodiments, -L-(P)$_t$ in formula (I) is -L$^2$-L$^1$-B-P, where formula (I) is:

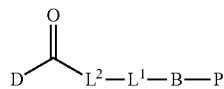

(I-1)

wherein

B is independently absent, or is 1) below, or 2) below, or a combination of 1) and 2) below: 1) a self-immolative spacer Sp1; 2) a divalent group, or a combination of two or more divalent groups, where the divalent group is selected from: —CR$^1$R$^2$—, C$_{1-10}$ alkylene, C$_{4-10}$ cycloalkylene, C$_{4-10}$ heterocyclylene and —(CO)—;

L$^1$ is independently absent, or is an uncleavable sequence; or is a cleavable sequence including an amino acid sequence that is enzymatically cleavable, and the amino acid sequence that is enzymatically cleavable includes 1, 2, 3, 4, 5, 6, 7, 8, 9 or 10 amino acids;

L$^2$ is independently absent; or is 1) below; or 2) below; or a combination of 1) and 2) below:

1) —NH—C$_{2-20}$ alkylene, wherein one or more —CH$_2$— structures in the alkylene are optionally replaced by the following groups: —CR$_3$R$_4$—, —O—, —(CO)—, —S—, —S(=O)$_2$—, —NR$^5$—, —N$^\oplus$R$^6$R$^7$—, C$_{4-10}$ cycloalkylene, C$_{4-10}$ heterocyclylene and phenylene, wherein the cycloalkylene, the heterocyclylene and the phenylene are each independently unsubstituted or substituted with at least one substituent selected from halogen, —C$_{1-10}$ alkyl, —C$_{1-10}$ haloalkyl, —C$_{1-10}$ alkylene —NH— R$^8$ and —C$_{1-10}$ alkylene —O—R$^9$;

2) an amino acid residue sequence, i.e., -*(AA)$_n$**-, wherein n is an integer from 1, 2, 3, 4, 5, 6, 7, 8, 9 or 10 to 100, AA, at each occurrence, is independently an amino acid residue, * represents an N-terminus of a corresponding amino acid and ** represents a C-terminus of the corresponding amino acid, and —(C$_2$H$_4$—O)$_m$—(CH$_2$)$_p$— is optionally present between amino and α-carbon of an amino acid, wherein m is 1, 2, 3, 4, 5, 6, 7, 8, 9 or 10; p is 0, 1, 2 or 3, and the * terminus forms an amide bond with the carbonyl in the disaccharide structure;

R$^1$, R$^2$, R$^3$, R$^4$, R$^5$, R$^6$, R$^7$, R$^8$ and R$^9$ are each independently selected from hydrogen, halogen, substituted or unsubstituted —C$_{1-10}$ alkyl, and C$_{4-10}$ cycloalkylene; or R$^1$ and R$^2$ and carbon atoms attached thereto together form a 3 to 6-membered cycloalkylene, and/or R$^3$ and R$^4$ and carbon atoms attached thereto together form a 3 to 6-membered cycloalkylene;

P is a payload attached to moiety B, or moiety L$^1$, or moiety L$^2$.

In some embodiments, -L-(P)t is

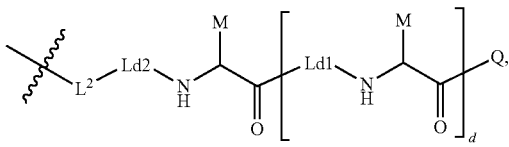

that is, formula (I) is:

formula (I-2)

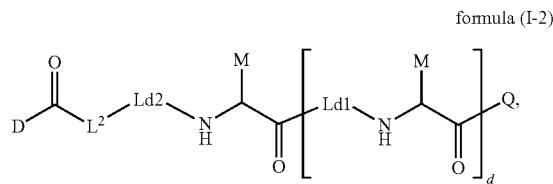

wherein

Ld2 and each Ld1 are independently bonds, or are selected from —NH—C$_{1-20}$ alkylene-(CO)— and —NH-(PEG)$_i$-(CO)—, or are natural amino acids independently unsubstituted or substituted with —CO-(PEG)$_j$-R$^{11}$ on a side chain or oligomeric natural amino acids with a polymerization degree of 2 to 10 (i.e., 2, 3, 4, 5, 6, 7, 8, 9 or 10); R$^{11}$ is C$_{1-10}$ alkyl;

d is 0, 1, 2, 3, 4, 5 or 6;

-(PEG)$_i$- and -(PEG)$_j$- are each a PEG fragment, including a specified number of continuous —(O—C$_2$H$_4$)-structural units or continuous —(C$_2$H$_4$—O)— structural units, optionally with C$_{1-10}$ alkylene attached at one end; each i is independently an integer from 1 to 100, and each j is independently an integer from 1 to 100;

M is hydrogen or LKa-L$^2$-L$^1$-B-P:

Q is NH$_2$ or L$^2$-L$^1$-B-P:

provided that the following cases are excluded: M is hydrogen and Q is NH$_2$;

each LKa is independently selected from

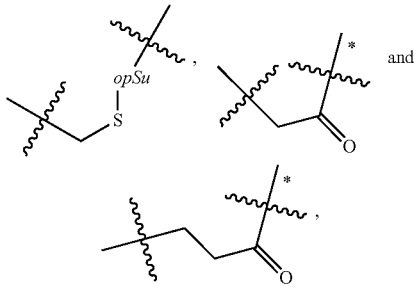

opSu is

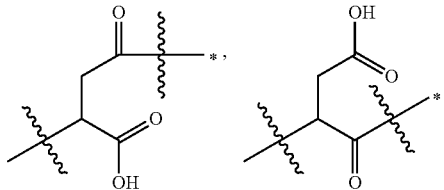 [SMILES: *C(=O)CC(*)C(=O)O ; *C(=O)C(*)CC(=O)O]

or a mixture thereof; where * represents a moiety attached to L$^2$;

B is independently absent, or is 1) below, or 2) below, or a combination of 1) and 2) below: 1) a self-immolative spacer Sp1; 2) a divalent group, or a combination of two or more divalent groups, wherein the divalent group is selected from: —CR$^1$R$^2$—, C$_{1-10}$ alkylene, C$_{4-10}$ cycloalkylene, C$_{4-10}$ heterocyclylene and —(CO)—;

L$^1$ is independently absent, or is an uncleavable sequence; or is a cleavable sequence including an amino acid sequence that is enzymatically cleavable, and the amino acid sequence that is enzymatically cleavable includes 1, 2, 3, 4, 5, 6, 7, 8, 9 or 10 amino acids;

L¹ is independently absent; or is 1) below; or 2) below; or a combination of 1) and 2) below:
1) —NH—$C_{2-20}$ alkylene, where one or more —$CH_2$— structures in the alkylene are optionally replaced by the following groups: —$CR^3R^4$—, —O—, —(CO)—, —S—, —S(=O)$_2$13, —$NR^5$—, —$N^{\oplus}R^6R^7$—, $C_{4-10}$ cycloalkylene, $C_{4-10}$ heterocyclylene and phenylene, wherein the cycloalkylene, the heterocyclylene and the phenylene are each independently unsubstituted or substituted with at least one substituent selected from halogen, —$C_{1-10}$ alkyl, —$C_{1-10}$ haloalkyl, —$C_{1-10}$ alkylene —NH—$R^8$ and —$C_{1-10}$ alkylene —O—$R^9$;
2) an amino acid residue sequence, i.e., -*(AA)$_n$**-, wherein n is an integer from 1, 2, 3, 4, 5, 6, 7, 8, 9 or 10 to 100, AA, at each occurrence, is independently an amino acid residue, * represents an N-terminus of a corresponding amino acid and ** represents a C-terminus of the corresponding amino acid, and —($C_2H_4$—O)$_m$—($CH_2$)$_p$— is optionally present between amino and α-carbon of an amino acid, wherein m is 1, 2, 3, 4, 5, 6, 7, 8, 9 or 10; p is 0, 1, 2 or 3, and the * terminus forms an amide bond with the carbonyl in the disaccharide structure;

$R^1$, $R^2$, $R^3$, $R^4$, $R^5$, $R^6$, $R^7$, $R^8$ and $R^9$ are each independently selected from hydrogen, halogen, substituted or unsubstituted —$C_{1-10}$ alkyl, and $C_{4-10}$ cycloalkylene; or $R^1$ and $R^2$ and carbon atoms attached thereto together form a 3 to 6-membered cycloalkylene, and/or $R^3$ and $R^4$ and carbon atoms attached thereto together form a 3 to 6-membered cycloalkylene;

P is a payload attached to moiety B, or moiety L¹, or moiety L².

In some embodiments, L² is an amino acid residue sequence, i.e., -*(AA)$_n$**-, where n is an integer from 1 to 100, AA, at each occurrence, is independently an amino acid residue, * represents the N-terminus of a corresponding amino acid and ** represents the C-terminus of the corresponding amino acid, and —($C_2H_4$—O)$_m$—($CH_2$)$_p$— is optionally present between amino and α-carbon of an amino acid, where m is 1, 2, 3, 4, 5, 6, 7, 8, 9 or 10; p is 0, 1, 2 or 3, and the * terminus forms an amide bond with the carbonyl in the oligosaccharide structure. In some embodiments, AA, at each occurrence, is independently any one of Phe, Lys, Gly, Ala, Leu, Asn, Val, Ile, Pro, Trp, Ser, Tyr, Cys, Met, Asp, Gln, Glu, Thr, Arg and His, or any combination thereof.

In some embodiments, n is any integer from 1 to 100. In some embodiments, n is 1, 2, 3, 4, 5, 6, 7, 8, 9, 10, 11, 12, 14, 20, 22, 25, 28, 32, 34, 40, 50, 52, 60, 70, 86, 90, 100, or an interval value (or endpoint value) between any two values. In some embodiments, n is about 1 to 50. In some embodiments, n is about 1 to 30. In some embodiments, n is about 1 to 20. In some embodiments, n is about 1 to 10.

In some embodiments, L¹ is a cleavable sequence including an amino acid sequence that is enzymatically cleavable, wherein the amino acid sequence that is enzymatically cleavable includes 1, 2, 3, 4, 5, 6, 7, 8, 9 or 10 amino acids. In some embodiments, L¹ is any one of Val, Cit, Phe, Lys, Gly, Ala, Leu, Asn or any combination thereof, preferably -Gly-Gly-Phe-Gly-, -Phe-Lys-, -Val-Cit-, -Val-Lys-, -Gly-Phe-Leu-Gly-, -Ala-Leu-Ala-Leu-, -Ala-Ala-Ala-, and a combination thereof. In some embodiments, L¹ is -Val-Cit-.

In some embodiments, B is selected from:

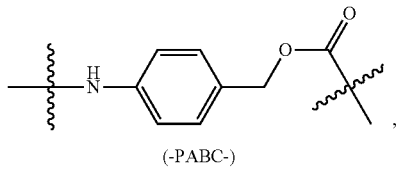 [SMILES: *Nc1ccc(COC(*)=O)cc1]

(-PABC-)

—NH—$CH_2$-U-, or —NH—$CH_2$-U-($CH_2$)$_g$—(CO)—; wherein g is 1, 2, 3, 4, 5 or 6; U is absent, $CH_2$, O, S or NH, preferably O or S.

In some embodiments, -L¹-B- represents -Val-Cit-PABC-. In some embodiments, -L²-L¹-B- represents -Gly-Gly-Gly-Val-Cit-PABC-.

In some embodiments, the payload is selected from the group consisting of: small molecule compounds (e.g., small molecule drugs with various mechanisms of action, including various traditional small molecule drugs, photoacoustic dynamic therapy drugs, photothermal therapy drugs, e.g., chemotherapy drugs, small molecule targeted drugs, immune agonists, and the like, e.g., traditional cytotoxic drugs such as cis-platinum, paclitaxel, 5-fluorouracil, cyclophosphamide and bendamustine; small molecule targeted drugs such as imatinib mesylate, gefitinib and anlotinib; immune agonists such as STING agonists and TLR agonists), nucleic acids and nucleic acid analogs, tracer molecules (including fluorescent molecules, biotin, fluorophores, chromophores, spin resonance probes, radioactive labels and the like), short peptides, polypeptides, peptidomimetics and proteins. In some embodiments, the payload is a cytotoxin or its fragment, having an optional derivation moiety to attach to L in the compound of formula (I).

In some embodiments, the cytotoxin is selected from the group consisting of: taxanes, maytenins, auristatins, epothilones, combretastatin A-4 phosphate, combretastatin A-4 and its derivatives, indole-sulfonamides, vinblastines such as vinblastine, vincristine, vindesine, vinorelbine, vinflunine, vinglycinate, anhy-drovinblastine, dolastatin 10 and its analogs, halichondrin B, eribulin, indole-3-oxoacetamides, podophyllotoxins, 7-diethylamino-3-(2'-benzoxazolyl)-coumarin (DBC), discodermolide, laulimalide, camptothecins and its derivatives, mitoxantrone, mitoguazone, nitrogen mustards, nitrosoureas, aziridines, benzodopa, carboquone, meturedepa, uredepa, dynemicin, esperamicin, neoearcinostatin, aclacinomycin, actinomycin, anthramycin, bleomycins, actinomycin C, carabicin, carminomycin, sarkomycin, carminomycin, actinomycin D, daunorubicin, detorubicin, doxorubicin, epirubicin, esorubicin, idarubicin, marcellomycin, mitomycins, nogalamycin, olivomycin, peplomycin, porfiromycin, puromycin, quelamycin, rodorubicin, streptonigrin, streptozocin, zinostatin, zorubicin, trichothecenes, T-2 toxin, verracurin A, roridin A, anguidine, ubenimex, azaserine, 6-diazo-5-oxo-L-norleucine, denopterin, methotrexate, pteropterin, trimetrexate, edatrexate, fludarabine, 6-purinethiol, thiamiprine, thioguanine, ancitabine, gemcitabine, enocitabine, azacitidine, 6-azauridine, carmofur, cytarabine, dideoxyuridine, doxifluridine, floxuridine, calusterone, dromostanolone propionate, epitiostanol, mepitiostane, testolactone, aminoglutethimide, mitotane, trilostane, flutamide, nilutamide, bicalutamide, leuprolide acetate, protein kinase inhibitors, and proteasome inhibitors; and/or the cytotoxin is selected from the group consisting of vinblastins, colchicines, taxanes, auristatins, maytansinoids, calicheamicin, doxonubicin, duocarmucin, SN-38, cryptophycin analogs, deruxtecan, duocarmazine, calicheamicin, centanamycin, dolastansine, pyrrolobenzodiazepine and exatecan and its derivatives; and/or the cytotoxin is selected from auristatin, especially MMAE, MMAF or MMAD; and/or the cytotoxin is selected from exatecan and its derivative, for example DX8951f; and/or the cytotoxin is selected from DXd-(1) and DXd-(2), preferably DXd-(1).

In some embodiments, the linker-payload compound (I-2) is as shown in formula:

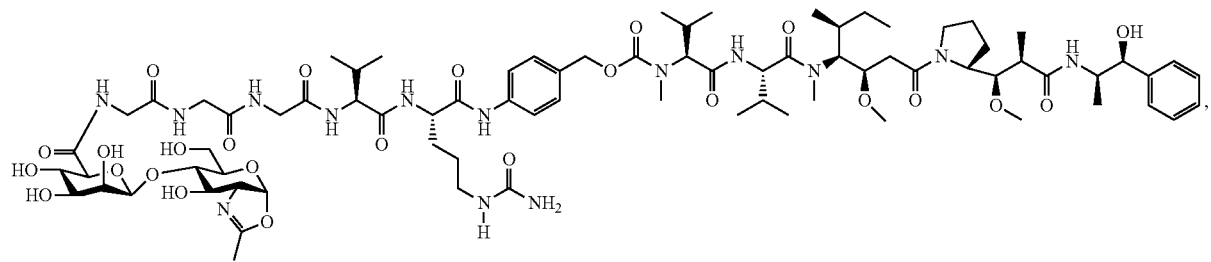
(I-3)
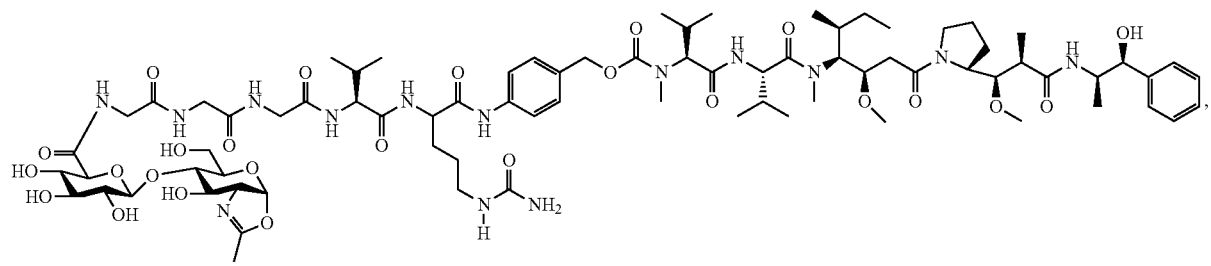
(I-4)
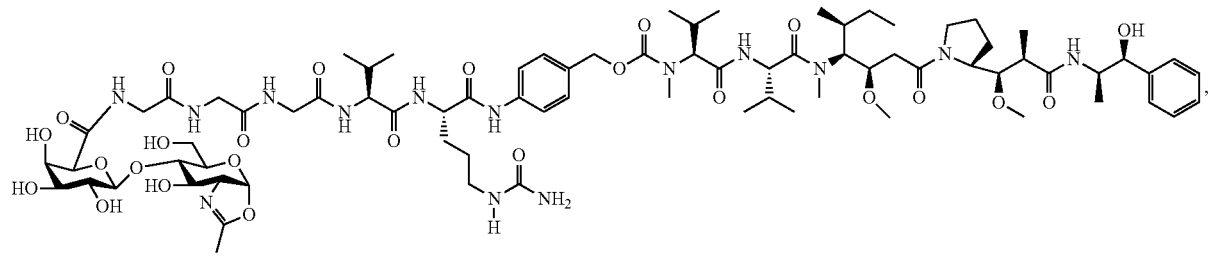
(I-5)
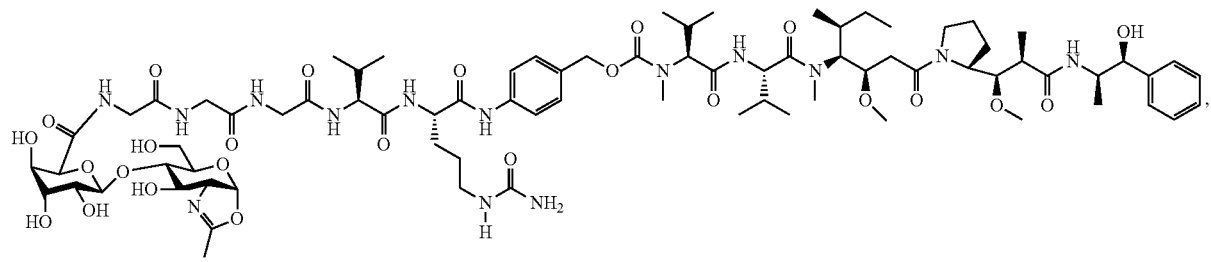
(I-6)
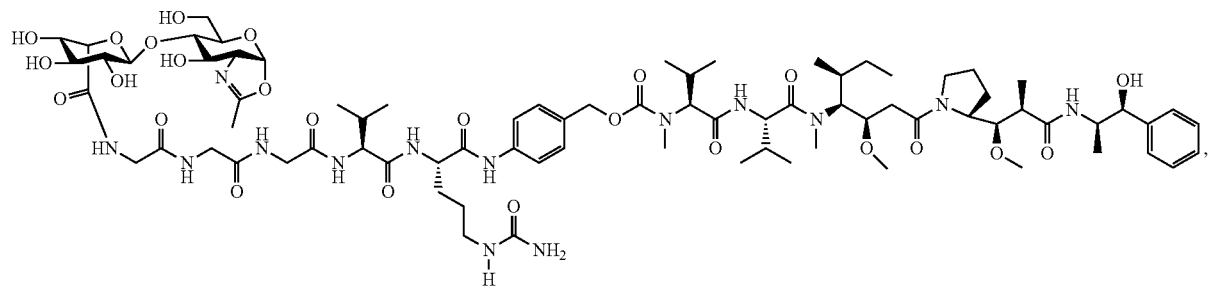
(I-7)

-continued
(I-8)
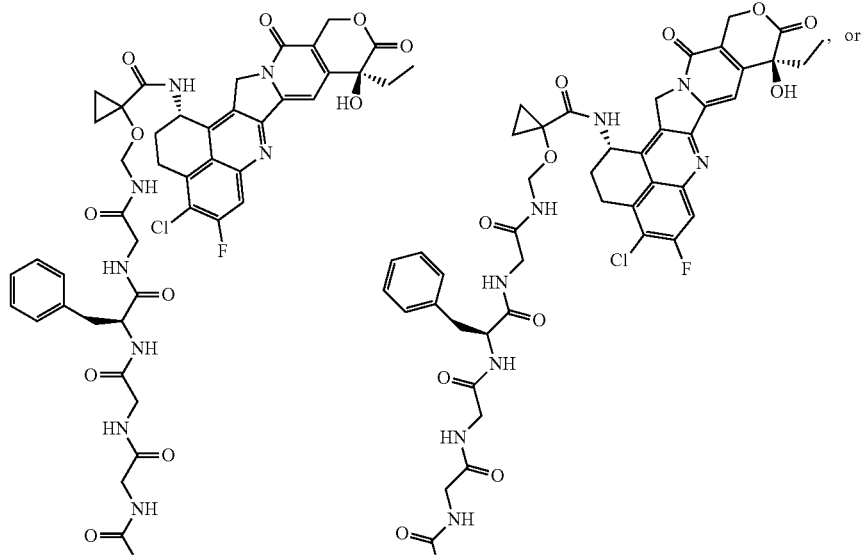
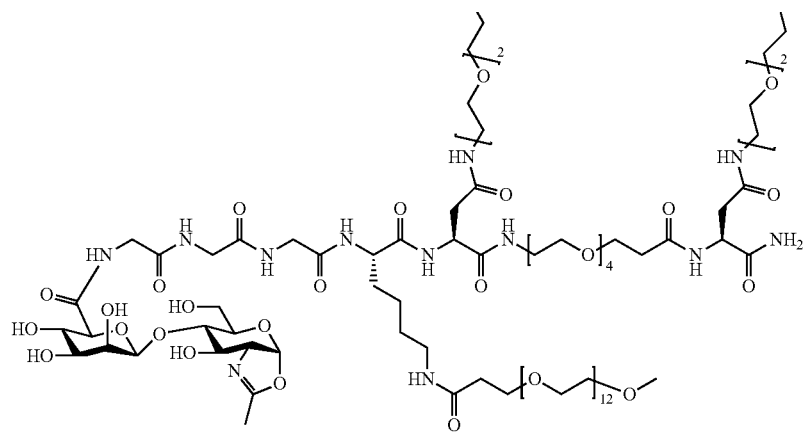
(I-9)
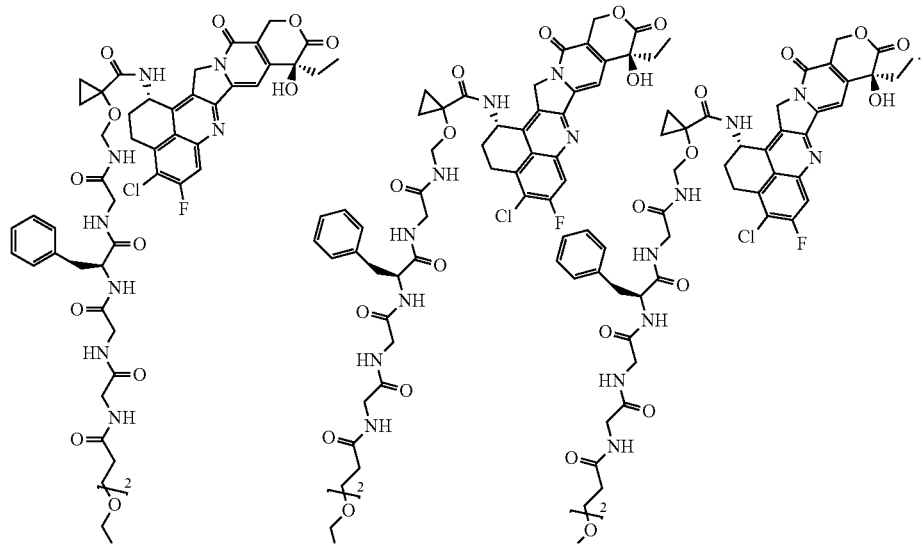

-continued

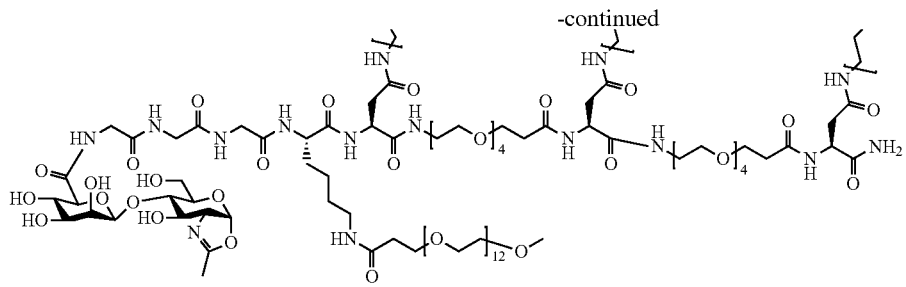

In some embodiments, the antibody is selected from the group consisting of: an anti-CD19 antibody, an anti-CD20 antibody, an anti-CD22 antibody, an anti-CD25 antibody, an anti-CD30/TNFRSF8 antibody, an anti-CD33 antibody, an anti-CD37 antibody, an anti-CD44v6 antibody, an anti-CD56 antibody, an anti-CD70 antibody, an anti-CD71 antibody, an anti-CD74 antibody, an anti-CD79b antibody, an anti-CD117/KITk antibody, an anti-CD123 antibody, an anti-CD138 antibody, an anti-CD142 antibody, an anti-CD174 antibody, an anti-CD227/MUC1 antibody, an anti-CD352 antibody, an anti-CLDN18.2 antibody, an anti-DLL3 antibody, an anti-ErbB2/HER2 antibody, an anti-CN33 antibody, an anti-GPNMB antibody, an anti-ENPP3 antibody, an anti-Nectin-4 antibody, an anti-EGFRvIII antibody, an anti-SLC44A4/AGS-5 antibody, an anti-CEACAM5 antibody, an anti-PSMA antibody, an anti-TIM1 antibody, an anti-LY6E antibody, an anti-LIV1 antibody, an anti-Nectin4 antibody, an anti-SLITRK6 antibody, an anti-HGFR/cMet antibody, an anti-SLAMF7/CS1 antibody, an anti-EGFR antibody, an anti-BCMA antibody, an anti-AXL antibody, an anti-NaPi2B antibody, an anti-GCC antibody, an anti-STEAP1 antibody, an anti-MUC16 antibody, an anti-mesothelin antibody, an anti-ETBR antibody, an anti-EphA2 antibody, an anti-5T4 antibody, an anti-FOLR1 antibody, an anti-LAMP1 antibody, an anti-Cadherin 6 antibody, an anti-FGFR2 antibody, an anti-FGFR3 antibody, an anti-CA6 antibody, an anti-CanAg antibody, an anti-integrin-αV antibody, an anti-TDGF1 antibody, an anti-ephrin A4 antibody, an anti-TROP2 antibody, an anti-PTK7 antibody, an anti-NOTCH3 antibody, an anti-C4.4A antibody, an anti-FLT3 antibody, an anti-B7H3/4 antibody, an anti-tissue factor (TF) antibody, and an anti-ROR1/2 antibody, preferably an anti-CD19 antibody, an anti-ErbB2/HER2 antibody, an anti-CLDN18.2 antibody, an anti-Nectin-4 antibody, an anti-FGFR3 antibody, and an anti-Trop2 antibody.

In some embodiments, the endoglycosidase with the glycosyltransferase activity is N-acetyl glucosamine endohydrolase. In some embodiments, the N-acetyl glucosamine endohydrolase includes at least one of Endo S (Streptococcus pyogenes endoglycosidase-S), Endo F3 (Elizabethkingia miricola endoglycosidase-F3), Endo S2 (Endoglycosidase-S2, S. pyogenes endoglycosidase-S2), Endo Sd (Endoglycosidase-Sd, S. pyogenes endoglycosidase-Sd) and Endo CC (Endoglycosidase-CC, S. pyogenes endonuclease-CC); or the N-acetyl glucosamine endohydrolase includes at least one of Endo H, Endo D, Endo F2, Endo F3, Endo M, Endo CC1, Endo CC2, Endo Om, Endo S and Endo S2.

In some embodiments, the endoglycosidase with the glycosyltransferase activity is covalently attached to a Halo tag, and an endoglycosidase fusion protein is immobilized on a support containing haloalkyl linker via the Halo tag; and the Halo tag refers to a dehalogenase or its variant or its truncated moiety with functional activity. In some embodiments, one end of the endoglycosidase is attached to a Halo tag, and the other end of the endoglycosidase is attached to a His tag (His tag is a histidine peptide, such as $His_4$, $His_5$, $His_6$, $His_8$, $His_{10}$, $His_{12}$, or $His_{14}$). In some embodiments, an amino end of the endoglycosidase is attached to a Halo tag, and a carboxyl end of the endoglycosidase is attached to a His tag, i.e., Halo-endoglycosidase-His (here His refers to the His tag, which is $His_4$, $His_5$, $His_6$, $His_8$, $His_{10}$, $His_{12}$, or $His_{14}$; similarly hereinafter). In some embodiments, an amino end of the endoglycosidase is attached to a Halo tag, and a carboxyl end of the endoglycosidase is attached to a His tag, the endoglycosidase being Endo-S2, i.e., Halo-Endo S2-His.

In some embodiments, the support includes a chloroalkyl linker, such that the endoglycosidase fusion protein is immobilized on the support under the covalent interaction between the chloroalkyl linker and a Halo tag. In some embodiments, the chloroalkyl linker is generated by a chloroalkyl substrate with a structure of formula (III):

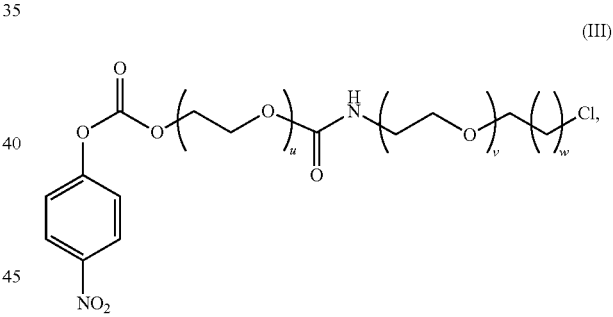

where u is an integer from 1 to 20, v is an integer from 0 to 20, and w is an integer from 1 to 19.

In some embodiments, the support has a structure of formula (IV):

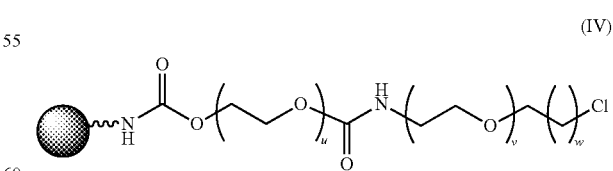

wherein u is an integer from 1 to 20, v is an integer from 0 to 20, and w is an integer from 1 to 19;
● is resin, a bead, a membrane, gel, a matrix, a film, a plate, a well, a tube, a glass slide or a surface. In some embodiments, ● is resin. In some embodiments, ● is agarose resin, silicone resin, polymethyl methacrylate resin, or cellulose resin. In some embodiments,  is highly cross-linked agarose resin or polymethyl methacrylate resin.

In one aspect, the present disclosure provides an endoglycosidase fusion protein, including an endoglycosidase and a Halo tag that are covalently attached together; and the Halo tag refers to a dehalogenase or its variant or its truncated moiety functional activity. In some embodiments, the endoglycosidase fusion protein consists of the endoglycosidase and Halo covalently attached together.

In some embodiments, one end of the endoglycosidase of the fusion protein is covalently attached to a Halo tag, and the other end of the endoglycosidase is covalently attached to a His tag. In some embodiments, an amino end of the endoglycosidase is covalently attached to a Halo tag, and a carboxyl end of the endoglycosidase is attached to a His tag.

In some embodiments, the endoglycosidase is selected from at least one of Endo S (*S. pyogenes* endoglycosidase-S), Endo F3 (*E. miricola* endoglycosidase-F3), Endo S2 (Endoglycosidase-S2, *S. pyogenes* endoglycosidase-S2), Endo Sd (Endoglycosidase-Sd, *S. pyogenes* endoglycosidase-Sd) and Endo CC (Endoglycosidase-CC, *S. pyogenes* endonuclease-CC); or the endoglycosidase is selected from at least one of Endo H, Endo D, Endo F2, Endo F3, Endo M, Endo CC1, Endo CC2, Endo Om, Endo S and Endo S2.

In an embodiment, the endoglycosidase is an endo-β-N-acetylglucosaminidase. In an embodiment, the endoglycosidase is selected from the group consisting of: Endo H, Endo D, Endo F2, Endo F3, Endo M, Endo CC1, Endo CC2, Endo Om, Endo S and Endo S2.

In some embodiments, the His tag is multiple continuous histidine residues. In some embodiments, the His tag is three histidines, four histidines, five histidines, six histidines, seven histidines, eight histidines, nine histidines or ten histidines. In some embodiments, the His tag is $His_6$. In an embodiment, the His tag is $His_8$. In an embodiment, the His tag is His10.

In an embodiment, the endoglycosidase fusion protein includes an amino acid sequence as set forth in SEQ ID NO: 1, or has at least 80% identity, at least 85% identity, and at least 90% identity with SEQ ID NO: 1, or has one or more conserved amino acid substitutions compared to SEQ ID NO: 1.

In some embodiments, the endoglycosidase fusion protein includes or consists of an amino acid sequence as set forth in SEQ ID NO: 1.

In some embodiments, the endoglycosidase fusion protein includes or consists of an amino acid sequence as set forth in positions 1 to 1150 in SEQ ID NO: 1, or has at least 90% identity with amino acids shown in positions 1 to 1150 in SEQ ID NO: 1, or has one or more conserved amino acid substitutions compared to the amino acids shown in positions 1 to 1150 in SEQ ID NO: 1. In some embodiments, the endoglycosidase fusion protein includes or consists of an amino acid sequence as set forth in positions 1 to 1150 in SEQ ID NO: 1.

In some embodiments, the endoglycosidase fusion protein has a PI of about 4 to 7. In some embodiments, the endoglycosidase fusion protein has a PI of about 4, 4.1, 4.3, 4.5, 4.7, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, or an interval value (or endpoint value) between any two values.

In one aspect, the present disclosure provides a method for preparing an endoglycosidase fusion protein of the present disclosure, including: (a) providing a nucleic acid sequence of an endoglycosidase; and (b) attaching one end of the nucleic acid sequence of the endoglycosidase to a nucleic acid sequence of a Halo tag;

cloning the obtained nucleic acid sequence into a suitable vector, then transforming the vector into a suitable host cell, and expressing the endoglycosidase fusion protein of the present disclosure in the host cell.

In some embodiments, the method for preparing the endoglycosidase fusion protein of the present disclosure includes: (a) providing a nucleic acid sequence of an endoglycosidase; (b) attaching one end of the nucleic acid sequence of the endoglycosidase to a nucleic acid sequence of a Halo tag; and (c) attaching the other end of the nucleic acid sequence of the endoglycosidase to a nucleic acid sequence of a His tag.

In some embodiments, the nucleic acid sequence of the Halo tag is attached to an amino end of the sequence of the endoglycosidase. In some embodiments, the nucleic acid sequence of the Halo tag is attached to an amino end of the nucleic acid sequence of the endoglycosidase, and the nucleic acid sequence of the His tag is attached to a carboxyl end of the nucleic acid sequence of the endoglycosidase.

In one aspect, the present disclosure provides an immobilized endoglycosidase fusion protein, including the endoglycosidase fusion protein of the present disclosure immobilized on a support.

In some embodiments, the support includes a haloalkyl linker, such that the endoglycosidase fusion protein is immobilized on the support under the covalent interaction between the haloalkyl linker and the Halo tag.

In some embodiments, the support includes a chloroalkyl linker, such that the endoglycosidase fusion protein is immobilized on the support under the covalent interaction between the chloroalkyl linker and a Halo tag. In some embodiments, the chloroalkyl linker is generated by a chloroalkyl substrate with a structure of formula (III):

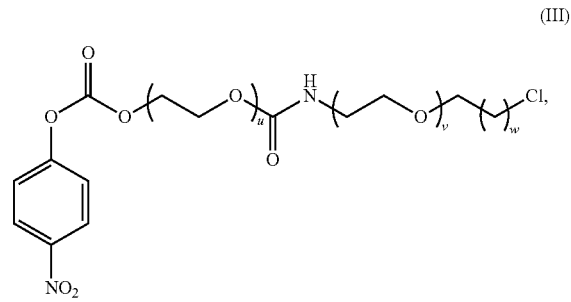

wherein u is an integer from 1 to 20, v is an integer from 0 to 20, and w is an integer from 1 to 19.

In some embodiments, the support has a structure of formula (IV):

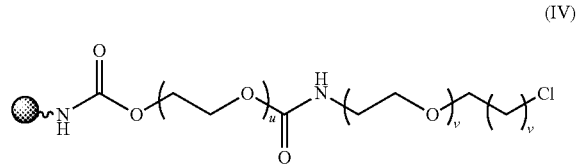

wherein u is an integer from 1 to 20, v is an integer from 0 to 20, and w is an integer from 1 to 19;

is resin, a bead, a membrane, gel, a matrix, a film, a plate, a well, a tube, a glass slide or a surface. In some embodiments, ◎ is resin. In some embodiments, ◎ is agarose resin, silicone resin, polymethyl methacrylate resin, or cellulose resin. In some embodiments, ◎ is highly cross-linked agarose resin or polymethyl methacrylate resin.

In another aspect, the present disclosure further provides a prepacked column, wherein the prepacked column is filled with an immobilized endoglycosidase fusion protein.

In another aspect, the present disclosure further provides applications of the immobilized endoglycosidase fusion protein, and/or the prepacked column in preparation and/or purification of drug conjugates or antibody conjugates. In some embodiments, the immobilized endoglycosidase fusion protein, and/or the prepacked column are/is easy in industrial scaled-up production in the preparation (such as purification) of the drug conjugates or the antibody conjugates.

A one-step conjugation system catalyzed by the immobilized endoglycosidase in this application has the following advantages:

1) liquid-phase enzyme catalysis requires a large amount of endoglycosidase, and meanwhile, a large number of enzyme-related impurities (such as the host proteins and the nucleic acids) are introduced into the reaction system, which has high requirements for enzyme purity (complex process and high preparation cost), and brings great challenges to the subsequent downstream removal of the impurities from the drug conjugates; enzyme immobilization does not have high requirements for the purity of initiation endoglycosidases (simple enzyme preparation process and low cost), and there are very few impurities introduced into the reaction system, which greatly simplifies a process for downstream removal of the impurities from the drug conjugates; and the enzyme immobilization is conducive to isolation and purification, such that the tool enzymes are removed from products more easily, and the possibility of shedding of product sugar chains and small molecules due to residues of the tool enzymes is reduced, thereby reducing the toxicity caused by potential product decomposition;

2) the enzyme immobilization is conducive to repeated use of the enzymes;

3) by a continuous flow intelligent conjugation technology, flows of reaction and purification are greatly simplified, the efficiency of drug discovery is greatly improved, and process robustness in drug production is guaranteed;

4) one-step conjugation of the antibody and the linker-payload is achieved by utilizing the endoglycosidase immobilized on the column;

5) the endoglycosidase fusion protein of the present disclosure has the PI of around 5.5, while the ADC has the PI of 8 to 9; and the use of AEX and/or CEX facilitates the removal of the endoglycosidase fusion proteins from the ADC products at the later stage; and 6) by conjugation column catalysis of the endoglycosidase fusion protein of the present disclosure, excellent conjugation efficiency can be achieved, linear scale-up is facilitated, and residual enzymes are easy to remove, which makes the endoglycosidase fusion protein more suitable for the industrial production of the ADCs.

1. DEFINITION

Figure 1:
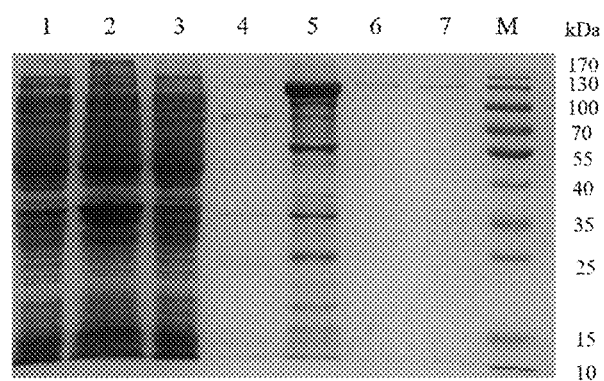
FIG. 1 shows an SDS-PAGE electropherogram of an purified endoglycosidase fusion protein (Halo-Endo S2-His) of the present disclosure, wherein 1 indicates that a sample is from a cell fluid, 2 indicates that a sample is from supernatant, 3 indicates that a sample is from a flow-through solution (components of an equilibration buffer used: 50 mM Tris, 150 mM NaCl, 20 mM imidazole, pH 7.4), 4 indicates that a sample is from a wash solution (components of the wash solution: 50 mM Tris, 150 mM NaCl, 80 mM imidazole, pH 7.4), 5 indicates that a sample is from an eluent (components of the eluent: 50 mM Tris, 150 mM NaCl, 500 mM imidazole, pH 7.4), 6 indicates that a sample is from an eluent (components of the eluent: 50 mM Tris, 150 mM NaCl, 500 mM imidazole, pH 7.4), and 7 indicates that a sample is from magnetic beads; and the molecular weight of the endoglycosidase fusion protein (Halo-Endo S2-His) is about 130 kDa.

Unless defined otherwise, all technical and scientific terms used in the present disclosure have the same meaning as is commonly understood by one of skill in the art. In addition, the terms and experimental procedures relating to protein and nucleic acid chemistry, molecular biology, cell and tissue culture, microbiology and immunology are those terms and common procedures widely used in the art. When a trade name is present herein, it refers to the corresponding commodity or the active ingredient thereof. All patents, published patents applications and publications cited herein are incorporated herein by reference. Meanwhile, for better understanding of the present disclosure, definitions and explanations of relevant terms are provided below.

As used herein, the expression "at least one" or "one or more" refers to one, two, three, four, five, six, seven, eight, nine or more, one hundred, two hundred, three hundred, four hundred, five hundred, six hundred, seven hundred, eight hundred, nine hundred or more, etc. As used herein, "a" and "an" unless clearly indicated to the contrary, should be understood to mean "at least one".

When a certain amount, concentration, or other value or parameter is set forth in the form of a range, a preferred range, or a preferred upper limit or a preferred lower limit, it should be understood that it is equivalent to specifically revealing any range formed by combining any upper limit or preferred value with any lower limit or preferred value, regardless of whether the range is explicitly recited. Unless otherwise stated, the numerical ranges listed herein are intended to include the endpoints of the range and all integers and fractions (decimals) within the range, and an interval value between any two numerical values. For example, the expression "u" is an integer from 1 to 20" should be understood as that u is any integer from 1 to 20, for example, u may be 1, 2, 3, 4, 5, 6, 7, 8, 9, 10, 11, 12, 13, 14, 15, 16, 17, 18, 19 or 20. Other similar expressions should also be understood in a similar manner.

The terms "about" and "approximately", when used in connection with a numerical variable, such as a concentration, an isoelectric point (pI), a pH, a temperature or a certain range, generally refers to that the value of the variable and all values of the variable are within experimental error (for example, within a 95% confidence interval for the mean) or within ±10% of a specified value, or a wider range.

The term "optional" or "optionally" refers to that the event described subsequent thereto may, but not necessarily happen, and the description includes the cases where the event or circumstance happens or does not happen.

The term "comprising", "including", "containing" and "having" are open-ended, and do not exclude additional unlisted elements, steps, or ingredients. The term "consisting of" excludes any element, step, or ingredient not designated. The term "consisting essentially of" refers to that the scope is limited to the designated elements, steps or ingredients, plus elements, steps or ingredients that are optionally present that do not substantially affect the essential and novel features of the claimed subject matter. It should be understood that the term "comprising" encompasses the terms "consisting essentially of" and "consisting of".

As used here, the definition of "biomolecule" encompasses proteins, nucleic acids, lipids, carbohydrates, small nucleotides, amino acids and derivatives thereof.

As used herein, a "nucleic acid" or a "polynucleotide" refers to a polymer of at least two nucleotides or nucleotide derivatives attached together by phosphodiester bonds, including deoxyribonucleic acid (DNA) and ribonucleic acid (RNA).

As used herein, a "vector" is a vehicle used to transfer an exogenous nucleic acid into a host cell, where the exogenous nucleic acid is amplified or expressed in the host cell. As used herein, the definition of "vector" encompasses plasmids (such as linearized plasmids), viral vectors, cosmids, phage vectors, phagemids, artificial chromosomes (e.g., yeast artificial chromosomes and mammalian artificial chromosomes), etc. As used herein, a vector is expressible and/or replicable within a host cell, meaning that the vector is capable of expressing RNA polynucleotides or polypeptides and/or producing multiple copies of the vector in the host cell. To be "expressible" or "replicable", the vector may include nucleic acid sequences or elements operably attached to a promoter or a replicon. As used herein, "operably attached" related to the nucleic acid sequences or elements refers to that these nucleic acid sequences are functionally correlated. For example, the promoter can be operably attached to a nucleic acid sequence coding a polypeptide, whereby the promoter regulates or mediates transcription of the nucleic acid. Those skilled in the art can select and use appropriate vectors for a particular purpose.

An Fc fusion protein refers to a recombinant protein obtained by performing fusion expression on bioactive proteins or peptides as well as a hinge region of IgG, and an Fc fragment, wherein the bioactive proteins or peptides include, for example, ligands, cytokines, receptors, antigens, and cyclic peptides that bind to cell surface antigens. The Fc fusion protein endows a fused protein with more antibody properties, including prolonging its plasma half-life, exerting unique functional effects of the Fc fragments, and the like.

A GlcNAc motif refers to a glycan chain with two conserved N-glycosylation sites on asparagine (Asn) at position 297 in an Fc region of an antibody, and the glycan chain includes N-acetylglucose-β-(1,4)-N-acetylglucose covalently attached to Asn. Fc region glycosylation is a complex post-translational modification process, in which various glycan chains with different lengths, composition, and structures are generated under the participation of various different enzymes. Different glycan chains have different effects on protein biological activity, conformation, stability, solubility, pharmacokinetics and the like. In some embodiments, an Fc glycosylated glycan molecule has a complex double-antenna core structure, which consists of two pentose molecules: mannose and N-acetylglucosamine; and different glycoforms contain different numbers of glycan molecules in addition to the core structure, such as fucose, mannose, N-acetylglucosamine, galactose, bisected N-acetylglucosamine and sialic acid. Heterogeneity is mainly caused by galactosylation and sialylation of terminal saccharides. According to the amount of terminal galactose, it is divided into three different subtypes (G0, G1, and G2). Each subtype includes different forms of core fucose, bisected N-acetylglucosamine or no core fucose, no bisected N-acetylglucosamine, i.e., a total of 16 neutral complex structures.

As used herein, "peptide", "polypeptide" or "protein" refers to two or more amino acids covalently attached. Unless otherwise specified, these terms are interchangeable.

The "amino acid" is an organic compound that contains both amino and carboxyl, such as α-amino acid, which can be coded by nucleic acid either directly or in the form of precursors. Single amino acid is coded by nucleic acid consisting of three nucleotides (so-called codons or base triads). Each amino acid is coded by at least one codon. The same amino acid is coded by different codons, which is called "degeneracy of genetic codes". Amino acids include natural amino acids and unnatural amino acids. The natural amino acids include alanine (three-letter code: Ala, one-letter code: A), arginine (Arg, R), asparagine (Asn, N), aspartate (Asp, D), cysteine (Cys, C), glutamine (Gln, Q), glutamate (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

As used herein, "sequence identity" has a meaning recognized in the art and the percent of sequence identity between two polypeptides can be calculated by aligning the two sequences using publicly available algorithms, such as the Basic Local Alignment Search Tool (BLAST) and the Fast Adaptive Shrinkage/Thresholding Algorithm (FASTA) (see, e.g., Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994). While there are a number of methods to measure identity between two polypeptides, the term "identity" is well known to those skilled in the art (Carrillo, H. & Lipman, D., SIAM J Applied Math 48:1073 (1988)).

As used herein, the term "variant" refers to a protein (nucleic acid) having substitutions, deletions, insertions of one or more residues (nucleotides) as compared to a reference protein. The reference protein may be a naturally occurring protein that can be isolated from natural sources (i.e., a wild-type protein) or an engineered protein. As used herein, the function or activity of a variant, such as an EndoS variant, an EndoS2 variant or a Halo tag variant, is substantially similar with or comparable to or higher than that of reference EndoS, EndoS2 or Halo tag, respectively.

As used herein, the term "endoglycosidase" refers to an enzyme that catalyzes hydrolysis of internal glycosidic bonds of oligosaccharide chains and polysaccharides, which can be used to cleave polysaccharides from glycoproteins. In some embodiments, the "endoglycosidase" of the present application can be used for hydrolyzing a β-(1→4) glycosidic bond between two N-acetylglucoses at the N-glycosylation site in the Fc region of the antibody. "Glycosyltransferase activity" refers to that catalytically activated saccharides are attached to different receptor molecules, such as proteins, nucleic acids, oligosaccharides, lipids, and small molecules. In this application, a donor containing oxazoline oligosaccharide can be attached to GlcNAc in the Fc region of the antibody.

As used herein, the term "Halo tag" refers to a haloalkane dehalogenase or its variants, which removes a halogen from a haloalkyl substrate (e.g., a reagent including a haloalkyl moiety $—(CH_2)_{2-30}—X$, where X is a halogen such as F, Cl, Br, I, particularly Cl or Br), and forms a covalent bond with a remainder of the substrate. Mutated haloalkane dehalogenase has been described in, for example, WO2006/093529 and WO2008/054821, the relevant content of which is incorporated herein by reference. The mutated haloalkane dehalogenase that can be used in the present disclosure may include, but is not limited to, mutants of *Xanthobacter* dehalogenase (such as *Xanthobacter autotrophicus* dehalogenase (DhlA)) or *Rhodococcus* dehalogenase (such as *Rhodococcus rhodochrous* dehalogenase (DhaA)). For example, one or more substitutions are included at a residue of a catalytic triad, and for example, His272 is substituted with Phe/Ala/Gly/Gln/Asn or Asp106 is substituted with Cys or other substitutions, as described in WO2008/054821. The premise is that the mutated haloalkane dehalogenase is capable of forming a covalent bond with the haloalkyl substrate.

"His tag" is a peptide consisting of histidine, such as His-His ($His_2$), His-His-His ($His_3$), His-His-His-His ($His_4$), His-His-His-His-His ($His_5$), His-His-His-His-His-His ($His_6$), His-His-His-His-His-His-His-His-His-His ($His_{10}$).

As used herein, the term "fusion protein" refers to a protein product co-expressed by two or more genes obtained by a recombinant DNA technology. For example, a termination codon of a coding gene of a first protein is deleted, and then a second protein gene with a termination codon is attached, which can achieve co-expression of two genes. The endoglycosidase fusion protein may further include one or more additional elements, such as additional peptides or tags, e.g., Halo tags and/or His tags. In some embodiments, the endoglycosidase fusion protein substantially retains desired properties.

As used herein, the term "resin" refers to an organic polymer that has a softening or melting range after being heated, and has a tendency to flow under external force when softened, and is solid, semi-solid or liquid at room temperature. "Halogenated resin" refers to a new compound formed by substituting at least one functional group in the resin with halo.

As used herein, the term "conjugation" refers to the covalent attachment of at least two moieties (e.g., at least two molecules or at least two ends of the same molecule).

As used herein, a "conjugate" can be prepared from at least two moieties (e.g., at least two molecules or at least two ends/side chains of the same molecule) via covalent attachment.

As used herein, the term "antibody-drug conjugate" refers to a conjugate, which includes an antibody or antibody fragment covalently conjugated to a payload, and the payload is a small molecule compound, an agonist, nucleic acid, a nucleic acid analog, or a fluorescent molecule.

As used herein, the term "drug conjugate" refers to a conjugate, which includes a protein containing an Fc region, covalently conjugated to a payload, and the payload is a small molecule compound, an agonist, nucleic acid, a nucleic acid analog, or a fluorescent molecule.

The term "antibody" includes a wide variety of peptides that can be distinguished biochemically. Those skilled in the art will understand that categories of heavy chains include gamma, mu, alpha, delta, or epsilon (γ, μ, α, δ, ε), and some other subunits (e.g., γ1-γ4). The nature of this chain determines the type of antibody, which is IgG, IgM, IgA, IgG, or IgE. Immunoglobulin subunits (isotypes), e.g., IgG1, IgG2, IgG3, IgG4, IgG5 and the like, have been fully characterized and the functional specificity conferred is also known. All types of immunoglobulins are within the scope of protection disclosed in the present disclosure. In some embodiments, an immunoglobulin molecule is of an IgG type. IgG typically includes two same light chain peptides with a molecular weight of about 23,000 Daltons and two same heavy chain peptides with a molecular weight of about 53,000 to 70,000. These four chains are attached in a "Y" configuration by disulfide bonds, with the light chain starting from the "Y" port and extending through a variable region to surround the heavy chain.

The light chains can be divided into kappa (κ) or lambda (λ). Each heavy chain can bind to a κ or λ light chain. Generally, when the immunoglobulin is produced by hybridomas, B cells, or genetically engineered host cells, its light chains and heavy chains are bound via covalent bonds, and the "tail" moieties of two heavy chains are bound via covalent disulfide bonds or non-covalent bonds. In the heavy chain, an amino acid sequence extends from an N-terminus of a forked end of the configuration to a C-terminus at the bottom of each chain. A variable region of the κ light chain of the immunoglobulin is Vκ; and a variable region of the λ light chain of the immunoglobulin is Vλ.

Both the light chain and the heavy chain are divided into regions of structural and functional homology. The terms "constant" and "variable" are used based on functions. Variable regions of the light chain (VL) and heavy chain (VH) determine antigen recognition and specificity. Constant regions of the light chain and the heavy chain endow important biological properties such as secretion, transplacental movement, Fc receptor binding, complement binding and the like. Conventionally, the numbering of the constant regions increases as they become further away from an antigen-binding site or amino terminal of an antibody. An N-terminus moiety is a variable region, and a C-terminus moiety is a constant region; CH3 and CL domains each include carboxyl termini of the heavy chain and light chain.

In naturally occurring antibodies, assuming that the antibody is in its three-dimensional configuration in a water-containing environment, six "complementary determining regions" or "CDRs" present in each antigen-binding domain are short discontinuous amino acid sequences that form antigen-binding domains and bind specifically to an antigen. The remaining other amino acids in the antigen-binding domain, known as a "framework" region, exhibit small intermolecular variability. Most of framework regions mostly employ a β-sheet conformation, and the CDRs form a ring structure attached thereto, or in some cases form a part of a β-sheet structure. Therefore, the framework region forms a scaffold to make the CDRs localized in a correct orientation under the interchain non-covalent interaction. The antigen-binding domain with CDRs at particular positions forms a surface complementary to an epitope on an antigen. The complementary surface promotes non-covalent binding of an antibody to its antigen epitope. For a given heavy chain or light chain variable region, amino acids including both CDR and a framework region can be identified by a known method by those of ordinary skill in the art (see Kabat, E. et al., U.S. Department of Health and Human Services, Sequences of Proteins of Immunological Interest, (1983) as well as Chothia and Lesk, J.Mol.Biol., 196:901-917 (1987)).

CDRs defined according to Kabat and Chothia include an overlap or subset of amino acid residues when compared with each other. Nevertheless, the application of any specific definition to refer to CDRs of antibodies or their variants falls within the scope of the present disclosure. The numbering of an exact residue including a particular CDR will vary with the sequence and size of the CDR. Those skilled in the art can usually determine which particular residues the CDR includes according to an amino acid sequence of a variable region of the antibody. Kabat et al. also defines a numbering system applicable to a variable region sequence of any antibody. Those of ordinary skill in the art can apply the "Kabat numbering" system to any variable region sequence without relying on other experimental data other than the sequence itself. "Kabat numbering" refers to a numbering system proposed by Kabat et al., U.S. Dept. of Health and Human Services in "Sequence of Proteins of Immunological Interest" (1983). An EU numbering system may also be employed for antibodies.

A light chain constant region includes part of an amino acid sequence from a light chain of an antibody. Preferably, the light chain constant region (CL) includes at least one of a constant κ domain or a constant λ domain. A "light chain-heavy chain pair" refers to a collection of light chains and heavy chains that can form a dimer by disulfide bonds between a CL domain of the light chain and a CH1 domain of the heavy chain.

The "Fc region" is a tail region of an antibody, which interacts with some proteins of a cell surface receptor and complement system. This property allows the antibody to activate an immune system. In IgG, IgA, and IgD antibody isotypes, the Fc region consists of two same protein fragments derived from second and third constant regions of two heavy chains of the antibody. In IgM and IgE antibody isotypes, the Fc region contains three heavy chain constant domains (CH2-4). The Fc region of IgG has highly conserved N-glycosylation sites. Glycosylation of an Fc fragment is necessary for Fc receptor-mediated activity, and different glycoforms have different influences on pharmacological properties of therapeutic antibodies.

Antibodies can be prepared by using a conventional recombinant DNA technology. Cell lines for antibody production can be selected, constructed, and cultured using techniques known to those skilled in the art. These technologies are described in various laboratory manuals and major publications. In this regard, the technical references suitable for use in the present disclosure are described below, such as Current Protocols in Immunology, Coligan et al., ed., Green Publishing Associates and Wiley-Interscience, John Wiley and Sons, New York (1991), Recombinant DNA Technology for Production of Protein Therapeutics in Cultured Mammalian Cells, D. L. Hacker, F. M. Wurm, in Reference Module in Life Sciences, 2017, the entire content of which, including supplementary content, is incorporated herein by reference.

In some embodiments, DNA coding an antibody can be designed and synthesized according to an amino acid sequence of the antibody described herein by a conventional method. The DNA is placed in an expression vector, then a host cell is transfected, and the transfected host cell is cultured in a medium to produce a monoclonal antibody. In some embodiments, the antibody expression vector includes at least one promoter element, an antibody coding sequence, a transcription termination signal, and a polyA tail. Other elements include an enhancer, a Kozak sequence, donor and receptor sites for RNA splicing on both sides of an insertion sequence. Efficient transcription can be achieved by early and late promoters of SV40, long terminal repeat sequences from retroviruses, such as RSV, HTLV1, HIVI, and early promoters of cytomegaloviruses. Some other cell promoters such as an actin promoter can also be applied. Suitable expression vectors may include pIRES1neo, pRetro-Off, pRetro-On, PLXSN, or Plncx, pcDNA3.1 (+/−), pcDNA/Zeo (+/−), pcDNA3.1/Hygro (+/−), PSVL, PMSG, pRSV-cat, pSV2dhfr, pBC12MI, pCS2 and the like. Commonly used mammalian cells include a 293 cell, a Cos1 cell, a Cos7 cell, a CV1 cell, a murine L cell, a CHO cell and the like.

In some embodiments, an insertion gene fragment needs to contain a screening marker. Common screening markers include a dihydrofolate reductase screening gene, a glutamine synthetase screening gene, a neomycin resistance screening gene, a hygromycin resistance screening gene and the like to screen and isolate a successfully transfected cell. A constructed plasmid is transfected into a host cell without the above-mentioned genes. The transfected host cell is cultured in a selective medium. The successfully transfected cell grows in mass, producing a desired protein of interest.

As used herein, the term "isoelectric point (pI)" is the pH (concentration index of hydrogen) value of an aqueous solution at which a molecule (such as a protein) carries no net surface charge and is expressed as pH units. The pI of a protein can be experimentally measured using methods well-known in the art, such as, imaged capillary isoelectric focusing (iCIEF) and capillary isoelectric focusing (CIEF). Different biomolecules (proteins, nucleic acids, polysaccharides, etc.) with different pIs may carry different charges at a given pH, allowing them to be isolated by methods such as ion exchange chromatography or isoelectric focusing.

As used herein, a molecule having an "alkaline pI" refers to that the molecule has a pI above 7.0. As used herein, a molecule having an "acidic pI" refers to that the molecule has a pI below 7.0.

As used herein, "ion exchange chromatography (IEX)" refers to a technology of isolating biomolecules based on differences in net surface charges of biomolecules and differences in their affinity to an ion exchanger (also referred to as a medium, resin or stationary phase). For example, in the anion exchange chromatography, a protein with a pI below the pH of a buffer will carry negative net surface charges and bind to a positively charged anion exchanger. However, another protein with a pI above the pH of the buffer will carry positive net surface charges and do not bind to the positively charged anion exchanger, and will thereby pass through the medium together with the buffer.

As used herein, the term "support" refers to a water-insoluble substance that can be isolated from a reaction mixture in a solid or semi-solid form, such as a surface, gel, a polymer, a matrix, a particle, resin, a bead or a membrane.

A "spacer" is a structure that is located between different structural modules and can spatially isolate the structural modules. The definition of spacer is not limited by whether it has a certain function or whether it can be cleaved or degraded in vivo. Examples of the spacer include, but are not limited to, amino acid and non-amino acid structures, wherein the non-amino acid structure may include but is not limited to amino acid derivatives or analogs. A "spacer sequence" refers to an amino acid sequence that serves as the spacer, and examples of the spacer sequence include, but are not limited to, a single amino acid, a sequence containing multiple amino acids, for example a sequence containing two amino acids, such as GA, or for example GGGGS, GGGGSGGGGS, GGGGSGGGGSGGGGS, etc. A self-immolative spacer (e.g., a self-immolative spacer Sp1) is a covalent component. The covalent component causes a protective moiety of a precursor to be activated followed by successive cleavage of two chemical bonds: the protective moiety (e.g., a cleavable sequence) is removed after activated, which initiates a cascade of decomposition reactions, resulting in the sequential release of smaller molecules. Examples of the self-immolative spacers include, but are not limited to, p-aminobenzyloxycarbonyl (PABC), acetal, heteroacetal, and a combination thereof.

The term "alkyl" refers to a straight or branched-chain saturated aliphatic hydrocarbon group consisting of carbon and hydrogen atoms. The saturated aliphatic hydrocarbon group is attached to the remainder of the molecule by a single bond. The alkyl may have 1 to 20 carbon atoms, referring to "$C_1$-$C_{20}$ alkyl", for example, $C_1$-$C_4$ alkyl, $C_1$-$C_3$ alkyl, $C_1$-$C_2$ alkyl, $C_3$ alkyl, $C_4$ alkyl, and $C_3$-$C_6$ alkyl. Non-limiting examples of the alkyl include, but are not limited to, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl, or isomers thereof. Divalent free radical refers to a group obtained by removing a hydrogen atom from a carbon atom having free valence electrons of a corresponding monovalent free radical. The divalent free radical has two attachment sites attached to the remainder of the molecule. For example, "alkylene" or "alkylidene" refers to a saturated straight or branched-chain divalent bivalent hydrocanbon radical. Examples of "alkylene" include, but are not limited to, methylene (—$CH_2$—), ethylidene (—$C_2H_4$—), propylidene (—$C_3H_6$—), butylene (—$C_4H_8$—), pentylene (—$C_5H_{10}$—), hexylene (—$C_6H_{12}$—), 1-methylethylidene (—$CH(CH_3)CH_2$—), 2-methylethylidene (—$CH_2CH(CH_3)$—), methylpropylidene or ethylpropylidene.

The term "cycloalkyl" refers to a cyclic saturated aliphatic group consisting of carbon and hydrogen atoms. The cyclic saturated aliphatic group is attached to the remainder of the molecule by a single bond. The cycloalkyl may have 3 to 10 carbon atoms, namely "$C_3$-$C_{10}$ cycloalkyl", for example cyclopropyl, cyclobutyl, cyclopentyl, cyclohexyl, cycloheptyl, cyclooctyl, cyclononyl, or cyclodecyl. "Cycloalkylene" refers to divalent cycloalkyl.

The term "heterocyclyl" refers to that one or more carbon atoms in the above-mentioned cycloalkyl are replaced by heteroatoms selected from nitrogen, oxygen and sulfur, for example, aze, oxa, or thiocyclic propyl, aze, oxa, or thiocyclic butyl, pyrrolidinyl, pyrazolidinyl, imidazolidinyl, tetrahydrofuryl, tetrahydrothienyl, piperidinyl, piperazinyl, tetrahydropyranyl, or tetrahydrothiapyranyl. "Heterocyclylene" refers to divalent cycloalkyl.

When referring to "substitution" herein, unless otherwise referring to, relevant substituents are selected from alkyl, halogen, amino, monoalkyl amino, dialkyl amino, nitro, cyano, formyl, alkyl carbonyl, carboxy, alkyl oxycarbonyl, alkyl carbonyloxy, aminocarbonyl, monoalkylaminocarbonyl, dialkylaminocarbonyl, formylamino, alkyl carbonylamino, formyl (monoalkyl) amino or alkyl carbonyl (monoalkyl) amino.

As used herein, when a group is combined with another group, the attachment between the groups may be linear or branched, provided that a chemically stable structure is formed. The structure formed by such combination may be attached to other moieties of the molecule by any suitable atom in the structure, preferably by a specified chemical bond. For example, when two or more divalent groups selected from —$CR^1R^2$—, $C_{1-10}$ alkylene, $C_{4-10}$ cycloalkylene, $C_{4-10}$ heterocyclylene, and —(CO)— are bonded together to form a combination, two or more divalent groups can be linearly attached to each other, for example, —CR$^1$R$^2$—C$_{1-10}$ alkylene-(CO)—, —CR$^1$R$^2$—C$_{4-10}$cycloalkylene-(CO)—, —CR$^1$R$^2$—C$_{4-10}$cycloalkylene-C$_{1-10}$ alkylene-(CO)—, —CR$^1$R$^{2'}$—CR$^1$R$^{2'}$—(CO)—, —CR$^1$R$^2$-CR$^1$R$^{2'}$—CR$^{1''}$R$^{2''}$—(CO)—, etc. The resulting bivalent structure may be further attached to other moieties of the molecule.

2. LINKER-PAYLOAD COMPOUND

In one aspect, the present disclosure provides a linker-payload compound having formula (I):

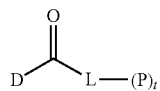

Wherein
P is a payload;
D-C(O)-L- is a linker;
D-C(O)— is a disaccharide structure or;
L is a linker end (for example, it can be cleaved from P chemically (e.g., via hydrolysis) or biologically (e.g., via enzymatic catalysis) to release P), and L is directly attached to carbonyl in D-C(O)— via —NH— therein, wherein when L is a branched linker end, L is attached to one P, and t is 1; while when L is a branch linker end, each branch can be attached to one P, and t is an integer greater than 1 (e.g., 2, 3, 4, 5, 6, 7, 8, 9, or 10).
In some embodiments, -L-(P)$_t$ is

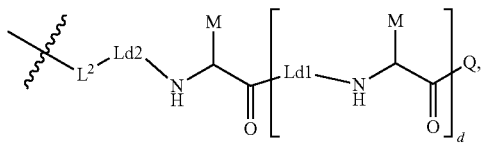

that is, formula (I) is:

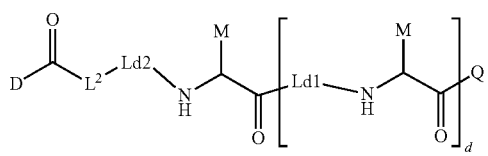

wherein
Ld2 and each Ld1 are independently bonds, or are selected from —NH—C$_{1-20}$ alkylene-(CO)— and —NH-(PEG)$_i$-(CO)—, or are natural amino acids independently unsubstituted or substituted with —CO-(PEG)$_j$-R$^{11}$ on a side chain or oligomeric natural amino acids with a polymerization degree of 2 to 10 (i.e., 2, 3, 4, 5, 6, 7, 8, 9 or 10);
-(PEG)$_i$- and -(PEG)$_j$- are each a PEG fragment, including a specified number of continuous —(O—C$_2$H$_4$)— structural units or continuous —(C$_2$H$_4$—O)— structural units, optionally with C$_{1-10}$ alkylene attached at one end;

M is hydrogen or LKa-L$^2$-L$^1$-B-P:
Q is NH$_2$ or L$^2$-L$^1$-B-P;
provided that the following cases are excluded: M is hydrogen and Q is NH$_2$;
Each LKa is independently selected from

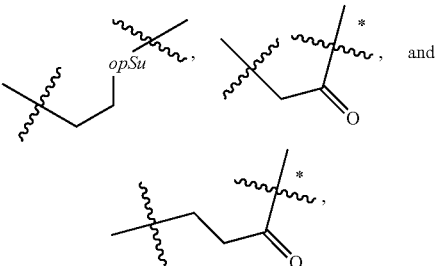

opSu is

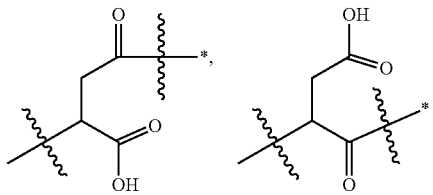

or a mixture thereof; wherein * represents a moiety attached to L$^2$;
Each L$^2$ is independently absent; or is 1) below; or 2) below; or a combination of 1) and 2) below:
1) —NH—C$_{2-20}$ alkylene, wherein one or more —CH$_2$— structures in the alkylene are optionally replaced by the following groups: —CR$^3$R$^4$—, —O—, —(CO)—, —S—, —S(=O)$_2$—, —NR$_5$—, —N$^⊕$R$^6$R$^7$—, C$_{4-10}$ cycloalkylene, C$_{4-10}$ heterocyclylene and phenylene, wherein the cycloalkylene, the heterocyclylene and the phenylene are each independently unsubstituted or substituted with at least one substituent selected from halogen, —C$_{1-10}$ alkyl, —C$_{1-10}$ haloalkyl, —C$_{1-10}$ alkylene —NH—R$^8$ and —C$_{1-10}$ alkylene —O—R$^9$;
2) an amino acid residue sequence, i.e., -*(AA)n**-, wherein n is an integer of 1, 2, 3, 4, 5, 6, 7, 8, 9 or 10, AA, at each occurrence, is independently an amino acid residue, * represents an N-terminus of a corresponding amino acid and ** represents a C-terminus of the corresponding amino acid, and —(C$_2$H$_4$—O)$_m$—(CH$_2$)$_p$— is optionally present between amino and α-carbon of an amino acid, wherein m is 1, 2, 3, 4, 5, 6, 7, 8, 9 or 10; p is 0, 1, 2 or 3, and the * terminus forms an amide bond with the carbonyl in the disaccharide structure;
L$^1$ is independently absent, or is an uncleavable sequence; or is a cleavable sequence including an amino acid sequence that is enzymatically cleavable, and the amino acid sequence that is enzymatically cleavable includes 1, 2, 3, 4, 5, 6, 7, 8, 9 or 10 amino acids;
Each B is independently absent, or is 1) below, or 2) below, or a combination of 1) and 2) below: 1) a self-immolative spacer Sp1; 2) a divalent group, or a combination of two or more divalent groups, wherein the divalent group is selected from: —CR$^1$R$^2$, C$_{1-10}$ alkylene, C$_{4-10}$ cycloalkylene, C$_{4-10}$ heterocyclylene and —(CO)—;

P is a payload attached to moiety B, or moiety L¹, or moiety L²;

R¹, R², R³, R⁴, R⁵, R⁶, R⁷, R⁸ and R⁹ are each independently selected from hydrogen, halogen, substituted or unsubstituted —C$_{1-10}$ alkyl, and C$_{4-10}$ cycloalkylene; or R¹ and R² and carbon atoms attached thereto together form a 3 to 6-membered cycloalkylene, and/or R³ and R⁴ and carbon atoms attached thereto together form a 3 to 6-membered cycloalkylene;

R¹¹ is C$_{1-10}$ alkyl;

d is 0, 1, 2, 3, 4, 5 or 6;

each i is independently an integer from 1 to 100. In some embodiments, i is about 1, 2, 3, 4, 5, 6, 7, 8, 9, 10, 14, 20, 30, 34, 40, 50, 60, 70, 90, 100, or an interval value (including endpoint values) between any two values;

each j is independently an integer from 1 to 100. In some embodiments, j is about 1, 2, 3, 4, 5, 6, 7, 8, 9, 10, 14, 20, 30, 34, 40, 50, 60, 70, 90, 100, or an interval value (including endpoint values) between any two values. In some embodiments, j is about 1 to 20. In some embodiments, j is about 8 to 12. In some embodiments, j is about 8, 9, 12 or 13.

In an embodiment, at least one of B, L¹ and L² is not "absent".

In an embodiment, L² is selected from: —NH—(CH$_2$)$_a$—(CH$_2$)$_2$(CO)—, wherein a is an integer of 0, 1, 2, 3, 4 or 5;

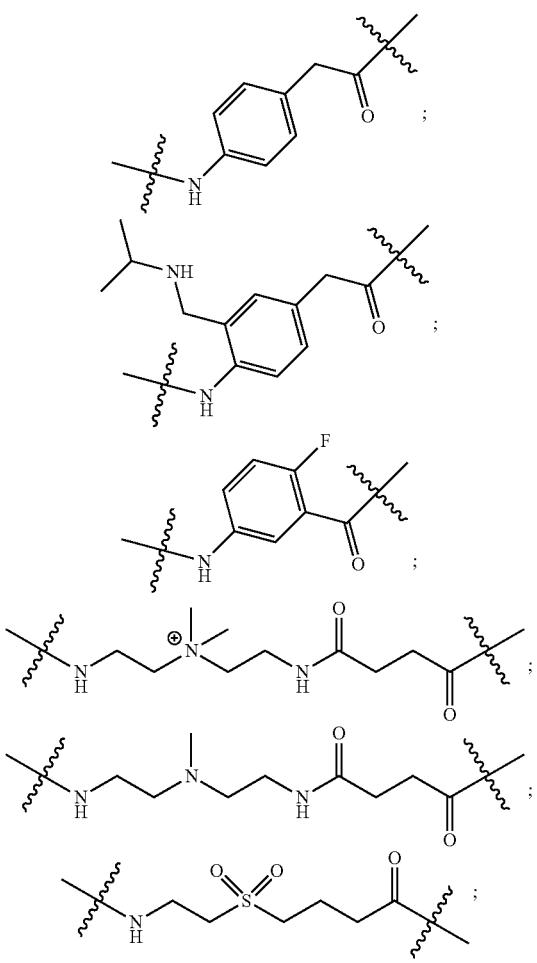

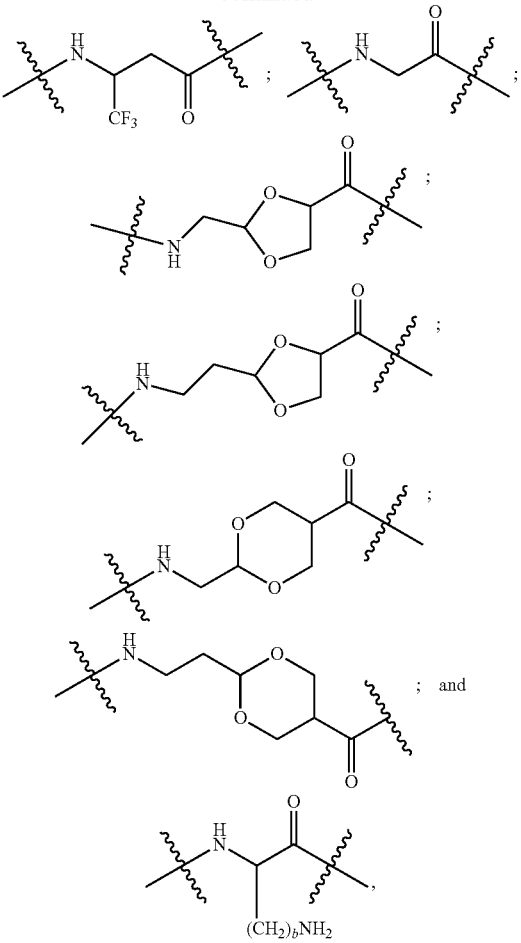

wherein b is 1, 2, 3, 4, 5, 6, 7, 8, 9 or 10. In an embodiment, the carbonyl in the above-mentioned L² structure is attached to L¹. In an embodiment, a is 0, 1, 2 or 3, preferably 3.

In an embodiment, L² is an amino acid residue sequence, i.e., -*(AA)$_n$**-, wherein n is an integer of 1, 2, 3, 4, 5, 6, 7, 8, 9 or 10, AA, at each occurrence, is independently an amino acid residue, * represents an N-terminus of a corresponding amino acid and ** represents a C-terminus of the corresponding amino acid, and —(C$_2$H$_4$—O)$_m$—(CH$_2$)$_p$— is optionally present between amino and α-carbon of an amino acid, wherein m is 1, 2, 3, 4, 5, 6, 7, 8, 9 or 10; p is 0, 1, 2 or 3, and the * terminus forms an amide bond with the carbonyl in the disaccharide structure. In an embodiment, AA, at each occurrence, is independently any one of Phe, Lys, Gly, Ala, Leu, Asn, Val, Ile, Pro, Trp, Ser, Tyr, Cys, Met, Asp, Gln, Glu, Thr, Arg, His, or any combination thereof. In an embodiment, n is an integer from 2 to 100, preferably an integer from 2 to 50, preferably an integer from 2 to 30, preferably an integer from 2 to 20, preferably an integer from 2 to 10, preferably 2, 3, 4, 5, 6, 7, 8 and 9.

In an embodiment, L¹ includes a cleavable sequence of an amino acid sequence that is enzymatically cleavable, wherein the amino acid sequence that is enzymatically cleavable includes 1, 2, 3, 4, 5, 6, 7, 8, 9 or 10 amino acids. In an embodiment, the amino acid sequence that is enzymatically cleavable is selected from -Gly-Gly-Phe-Gly-, -Phe-Lys-, -Val-Cit-, -Val-Lys-, -Gly-Phe-Leu-Gly-, -Ala-Leu-Ala-Leu-, -Ala-Ala-Ala- and a combination thereof; a preferred amino acid sequence that is enzymatically cleavable is -Gly-Gly-Phe-Gly-. In an embodiment, $L^1$ is any one of Val, Cit, Phe, Lys, Gly, Ala, Leu, Asn or any combination thereof, preferably -Gly-Gly-Phe-Gly-, -Phe-Lys-, -Val-Cit-, -Val-Lys-, -Gly-Phe-Leu-Gly-, -Ala-Leu-Ala-Leu-, -Ala-Ala-Ala- and a combination thereof. In an embodiment, $L^1$ represents -Val-Cit-.

In an embodiment, Sp1 is selected from PABC (p-aminobenzyloxycarbonyl), acetal, heteroacetal and a combination thereof. Preferably, Sp1 is acetal, heteroacetal or PABC. Further preferably, the heteroacetal is selected from N,O-heteroacetal. More preferably, Sp1 is —O—CH$_2$-U- or —NH—CH$_2$-U-, wherein —O— or —NH— is attached to an amino acid sequence that is enzymatically cleavable, U is absent, or is CH$_2$, O, S or NH, preferably O or S.

In an embodiment, B is absent, or is —NH—CH$_2$-U-, or —NH—CH$_2$-U-(CH$_2$)$_g$—(CO)—, wherein g is 1, 2, 3, 4, 5 or 6, U is absent, CH$_2$, O, S or NH, preferably O or S. In an embodiment, B is absent. In an embodiment, B is 1) below, 2) below, or a combination of 1) and 2) below: 1) a self-immolative spacer Sp1; 2) a divalent group, or a combination of two or more divalent groups, wherein the divalent group is selected from: —CR$^1$R$^2$—, C$_{1-10}$ alkylene and —(CO)—. In an embodiment, B is —NH—CH$_2$-U-, —NH—CH$_2$-U-(CH$_2$)$_g$—(CO)—, U is absent, CH$_2$, O, S or NH, preferably O or S. In an embodiment, B is attached to a payload by an amide bond or ester bond or ether bond. In an embodiment, B is selected from: (-PABC-), —NH—CH$_2$-U-, or —NH—CH$_2$U-(CH$_2$)$_g$—(CO)—; wherein g is 1, 2, 3, 4, 5 or 6; U is absent, CH$_2$, O, S or NH, preferably O or S.

In an embodiment, -$L^1$-B- represents -Val-Cit-PABC-.

In an embodiment, -$L^2$-$L^1$-B- represents -Gly-Gly-Gly-Val-Cit-PABC-.

In an embodiment, Ld2 and each Ld1 are independently selected from bonds, or

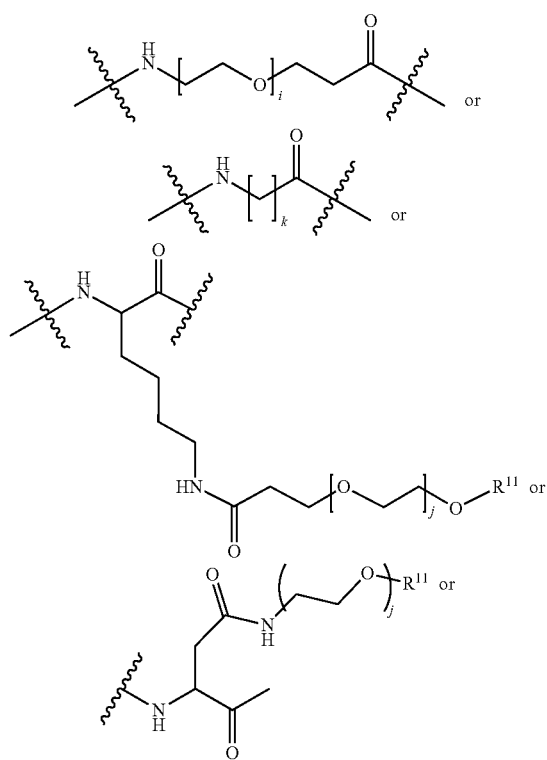

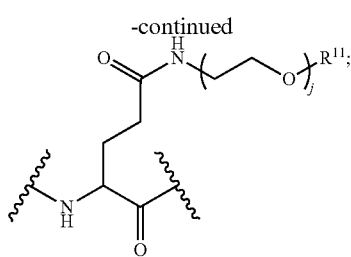

Each i, j and k are independently selected from integers from 1 to 100.

In an embodiment, each i, j and k are independently selected from integers from 1 to 20. In an embodiment, each i, j and k are independently selected from integers from 1 to 12.

In an embodiment, each i is independently selected from an integer from 2 to 8. In an embodiment, i is about 4.

In an embodiment, each j is independently selected from an integer from 8 to 12. In an embodiment, j is about 8 or 12.

In an embodiment, each k is independently selected from an integer from 1 to 7. In an embodiment, k is about 1 or 3, or 5.

In an embodiment, Ld2 and each Ld1 are independently selected from bonds; or C$_{1-20}$ alkylene with amino and carbonyl at both ends, respectively, or a certain length of PEG fragment (denoted as -(PEG)$_i$-) with amino and carbonyl at both ends, respectively, or one or more natural amino acids, wherein the natural amino acids are each independently unsubstituted or substituted with a certain length of PEG fragment (denoted as —CO-(PEG)$_j$-) on a side chain.

In an embodiment, -(PEG)$_i$- includes —(O—C$_2$H$_4$)$_i$— or —(C$_2$H$_4$—O)$_i$—, and optionally, C$_{1-10}$ alkylene is attached at one end; -(PEG)$_j$- includes (O—C$_2$H$_4$)$_j$—or —(C$_2$H$_4$—O)$_j$—, and optionally, C$_{1-10}$ alkylene is attached at one end. In an embodiment, -(PEG)$_i$- includes —C$_2$H$_4$—(O—C$_2$H$_4$)$_i$— or —(C$_2$H$_4$—O)$_i$—C$_2$H$_4$—.

3. IMMOBILIZATION OF ENDOGLYCOSIDASE

The support is in a solid or semi-solid form made of any material. Non-limiting examples of the support may include, but are not limited to, resin (e.g., an agarose resin, silicone resin, polymethyl methacrylate resin, epoxy resin or cellulose resin), gel (such as alginate hydrogel), a bead/microsphere/particle (e.g., a polystyrene bead, a magnetic particle), a plate, a well, a tube, a film, a membrane, a matrix and glass (e.g., a glass slide).

In some embodiments, the support is resin. In some embodiments, the support is selected from the group consisting of: agarose resin, silicone resin, polymethyl methacrylate resin, and cellulose resin. In some embodiments, the support is highly cross-linked agarose resin.

Methods for enzyme immobilization include adsorption, covalent or non-covalent binding, entrapment, encapsulation, and crosslinking. It is desirable that maximum enzymatic activity of the endoglycosidase can be retained after immobilization and a minimum amount of free endoglycosidase is present in a conjugate product after the conjugation reaction. In some embodiments, the support is modified on the surface to include one or more functional groups such that the endoglycosidase fusion protein can be covalently immobilized on the support.

In some embodiments, the support includes one or more chemically active functional groups that can form a covalent bond with reactive groups (such as amine, thiol and carboxylate) of the endoglycosidase fusion protein or with reactive groups in a haloalkyl substrate, or the support includes one or more binding partners of a corresponding binding tag/affinity label, wherein the binding tag/affinity label is included in the endoglycosidase fusion protein. Correspondence relationship between the chemically active functional groups and the reactive groups or between the binding tags/affinity labels and the binding partners is well-known in the art.

In some embodiments, the support includes a chemically active functional group that can form a covalent bond with reactive groups (such as amine, thiol and carboxylate) on the endoglycosidase fusion protein or with reactive groups in a haloalkyl substrate. In some embodiments, the functional groups included in the support are selected from the group consisting of: cyanate ester, isothiocyanate, isocyanate, carbodiimide, N-hydroxysuccinimide (NHS) ester, amine, carbonate, epoxide, maleimide, haloacetyl, aziridine, ethyl chloroformate and aliphatic aldehyde.

In some embodiments, the support is epoxy-activated resin, CNBr (cyanogen bromide)-activated resin, or NHS-activated resin. In some embodiments, the support is epoxy-activated resin. In some embodiments, the support is epoxy-activated agarose resin. In some embodiments, the support is epoxy-activated highly cross-linked agarose resin. In some embodiments, before reacting with the haloalkyl substrate, the epoxy activated resin is pretreated to introduce amino. In some embodiments, the pretreatment of the epoxy-activated resin is performed using ammonia. In some embodiments, the pretreatment of the epoxy-activated resin results in introduction of amino on an oxirane ring and ring-opening of the oxirane ring provides hydroxyl. Such hydroxyl is optionally end-capped in subsequent procedures of preparation of the support. In some embodiments, the pretreatment of the epoxy-activated resin results in introduction of amino on an oxirane ring and ring-opening of the oxirane ring provides hydroxyl, which is optionally esterified by an esterifying reagent (e.g., an acetylation reagent such as Ac$_2$O) in subsequent procedures of preparation of the support. Such pretreated epoxy-activated resin is within the scope of "epoxy-activated resin" as defined above. In some embodiments, the resin is agarose resin (such as highly cross-linked agarose resin) or polymethyl methacrylate resin.

In some embodiments, the support includes one or more binding partners of a corresponding binding tag/affinity label that is included in the endoglycosidase fusion protein, such as an additional tag or affinity label. Correspondence relationship between reactive groups or between the binding tags/affinity labels and the binding partners is well-known in the art. Examples of the binding tags/affinity labels and corresponding binding partners may include, but are not limited to, His tag and Ni$^{2+}$, biotin/SPB tag/Strep tag/Strep tag II and streptavidin/avidin/neutravidin, GST tag and glutathione, Fc tag and protein A, calmodulin tag and Ca$^{2+}$, MBP and amylose, S tag and ribonuclease S-protein, SNAP tag and benzylguanine (BG) derivatives, and CLIP tag and benzylcytosine (BC) derivatives.

In some embodiments, the support is functionalized by including a haloalkyl linker to form covalent interaction with a Halo tag. The haloalkyl linker can be introduced to the support by covalently attaching one or more functional groups included in the support to one or more reactive groups in a haloalkyl substrate, and the support obtained thereby is also referred to as a haloalkyl linker-modified support. The haloalkyl linker-modified support falls within the scope of the "support" defined above. Examples of the haloalkyl substrate include, but are not limited to, those described in e.g., US20060024808A1 and WO2006093529. The haloalkyl substrate and methods for preparing such supports are found in, for example, U.S. Pat. Nos. 7,429,472, 7,888,086 and 8,202,700, Japanese Pat. No. 4748685, the relevant content of which are incorporated herein by reference.

The haloalkyl substrate may include a haloalkyl moiety including primary or secondary halo. In some embodiments, the haloalkyl substrate includes primary halo. The halo in the haloalkyl moiety is selected from F, Cl, Br, and I. In some embodiments, the halo in the haloalkyl moiety is selected from Cl and Br. In some embodiments, the haloalkyl substrate has a structure of formula (V) below:

$$(F1_o\text{-}H1_e)_r\text{-}Lh\text{-}(F2_eH2_o)_s \quad (V)$$

wherein
F1 and F2 are independently a moiety including a reactive group, which can form a covalent bond with a chemically active functional group included in the support;
H1 and H2 are independently selected from C$_{2-30}$ haloalkyl;
Lh is a chemical bond or is C$_{3-200}$ alkylene, and wherein one or more (—CH$_2$—) structures in the alkylene are optionally replaced by —O—, —NH—, —(CO)—, —NH(CO)— and —(CO)NH—;
Lh is optionally substituted with 1, 2 or 3 substituents selected from —O—C$_{1-10}$ alkyl, —NH—C$_{1-10}$ alkyl, —(CO)—C$_{1-10}$ alkyl, —NH(CO)—C$_{1-10}$ alkyl and —(CO)NH—C$_{1-10}$ alkyl;
o is 0 or 1, e is 0 or 1, provided that o and e are different;
r is an integer from 1 to 100; and
s is an integer from 1 to 100.

In some embodiments, r is an integer from 1 to 10, e.g., 1, 2, 3, 4, 5, 6, 7, 8, 9, or 10. In some embodiments, s is an integer from 1 to 10, e.g., 1, 2, 3, 4, 5, 6, 7, 8, 9, or 10. In some embodiments, reactive groups in F1 or F2 are selected from amino, amine, thiol, and active ester. In some embodiments, the active ester contains one or more carboxylic acid radicals (such as in carbonic acid monoester of suitable alcohol or phenol, e.g., electron-deficient phenol like 4-nitrophenol; or such as in NHS ester or sulfo-NHS ester) or one or more sulfonic acid radicals (such as in methane sulfonic acid active ester, e.g., MsO—). In a specific embodiment, F1 or F2 is

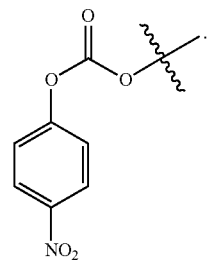 [SMILES: *OC(=O)Oc1ccc([N+](=O)[O-])cc1]

In some embodiments, H1 and H2 are independently selected from C$_{2-20}$ haloalkyl. In some embodiments, H1 and H2 are independently selected from C$_{2-10}$ haloalkyl, particularly C$_6$ haloalkyl. In some specific embodiments, the alkyl in H1 or H2 is linear alkyl. In some embodiments, H1 or H2 is (CH2)$_{2-30}$—X. In some embodiments, H1 or H2 is $(CH_2)_{2-20}$—X. In some embodiments, H1 or H2 is $(CH_2)_{2-10}$—X, particularly $(CH_2)_6$—X, where X is a halogen selected from F, Cl, Br, and I.

In some embodiments, the support is HaloLink™ resin (Promega).

In some embodiments, the support is resin that may include a haloalkyl linker. The haloalkyl linker includes a structure of —$(CH_2)_{2-30}$—X, wherein X is a halogen selected from F, Cl, Br, and I. In a specific embodiment, the support is haloaryl linker-modified resin. In some embodiments, the support is agarose resin or polymethyl methacrylate resin. In some embodiments, the support is highly cross-linked agarose resin.

In some embodiments, o is 1, e is 0, r is 1, s is 1, F1 is

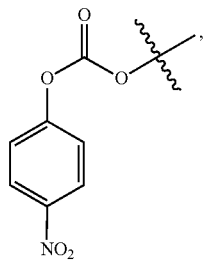 [SMILES: *OC(=O)Oc1ccc([N+](=O)[O-])cc1]

Lh is

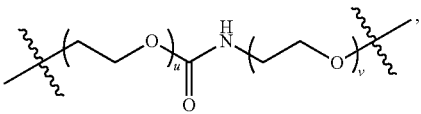

H2 is $(CH_2)_{2-20}$—Cl, and the haloalkyl substrate is a chloroalkyl substrate, which has a structure of formula (III):

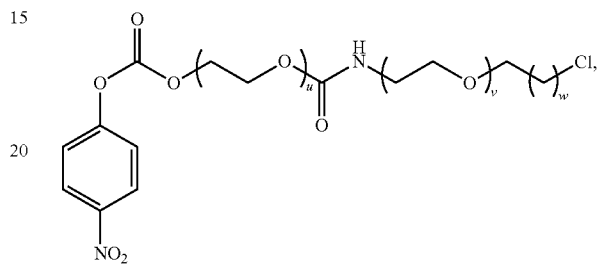

(III)

wherein u is an integer from 1 to 20, v is an integer from 0 to 20, and w is an integer from 1 to 19.

In a specific embodiment, u is 3, v is 2, and w is 5, and the chloroalkyl substrate has a structure of formula (III-1) below:

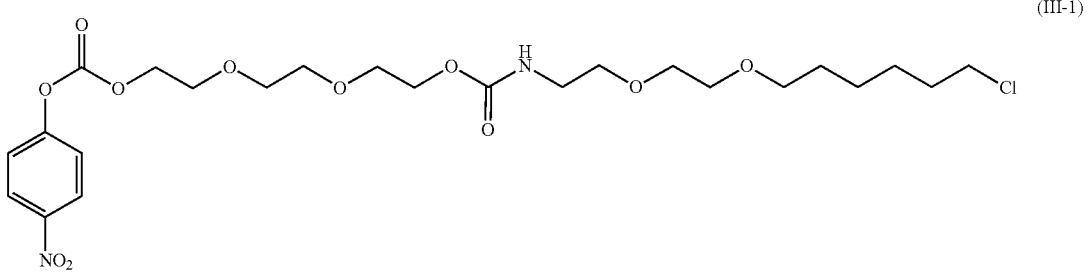 [SMILES: O=C(NCCOCCOCCCCCCCl)OCCOCCOCCOC(=O)Oc1ccc([N+](=O)[O-])cc1]

(III-1)

In some embodiments, the support is a chloroalkyl linker-modified support and has a structure of formula (IV):

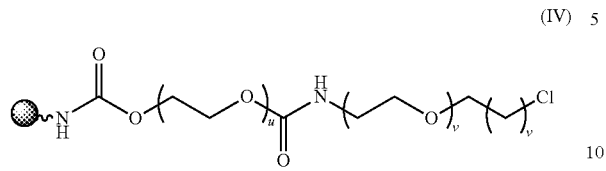

(IV)

wherein u is an integer from 1 to 20, v is an integer from 0 to 20, and w is an integer from 1 to 19; ⬤ represents the support, which is resin, a bead, a membrane, gel, a matrix, a film, a plate, a well, a tube, a glass slide or a surface. In some embodiments, the support is resin. In some embodiments, the support is agarose resin, silicone resin, polymethyl methacrylate resin, or cellulose resin. In some embodiments, the support is highly cross-linked agarose resin. Note that for sake of clarity, only a single chloroalkyl-linker moiety attached to the support is described, but it should be understood that there would be many such chloroalkyl-linker moieties attached onto the support.

In some embodiments, the chloroalkyl linker-modified support as shown in formula (IV) is prepared using resin, a bead, a membrane, gel, a matrix, a film, a plate, a well, a tube, a glass slide or a surface as denoted by ⬤, and the chloroalkyl substrate of formula (III).

In some embodiments, the chloroalkyl linker-modified support as shown in formula (IV) is prepared from pretreated epoxy-activated resin. The epoxy-activated resin is prepared by introduction of amino on an oxirane ring of the epoxy-activated resin, and ring-opening of the oxirane ring during the pretreatment provides hydroxy, which is optionally esterified using $Ac_2O$ in subsequent procedures of the preparation of the support, and the support as shown in formula (IV) has a structure of formula (IV-1):

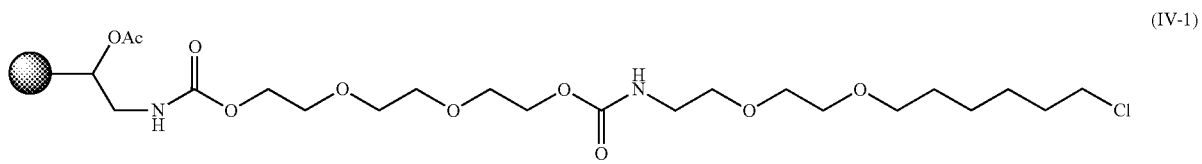 [SMILES: CC(=O)OC(C)CNC(=O)OCCOCCOCCOC(=O)NCCOCCOCCCCCCCl]

(IV-1)

wherein
the substructure

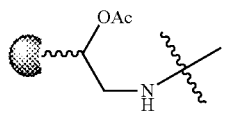 [SMILES: *NCC(C)OC(C)=O]

represents the pretreated epoxy-activated resin, wherein the moiety

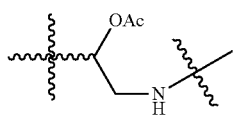

represents the oxirane ring which reacts with the amino and opens to give hydroxyl, and the hydroxyl is esterified subsequently to form AcO—, and the moiety ⬤ represents the other moiety of the pretreated epoxy-activated resin.

In some embodiments, the immobilized endoglycosidase fusion protein has the following structure:

Support-Linker-Halo Tag-EndoS/EndoS2-HisTag wherein

Support is a support (such as a solid support), e.g. selected from resin, a bead, a membrane, gel, a matrix, a film, a plate, a pore, a tube, a slide or a surface. In some embodiments, the support is resin. In some embodiments, the support is agarose resin, silicone resin, polymethyl methacrylate resin, or cellulose resin. In some embodiments, the support is highly cross-linked agarose resin or polymethyl methacrylate resin. In some embodiments, the support is selected from the group consisting of: NHS-activated resin, CNBr-activated resin and epoxy-activated resin.

Linker is a linker moiety covalently binding to the support, e.g., including a chain of 10 to 60 carbon atoms, optionally including one or more ether, ester, carbamate, and/or amide bonds; e.g., a linker moiety of formula (VI) or (VI-1)

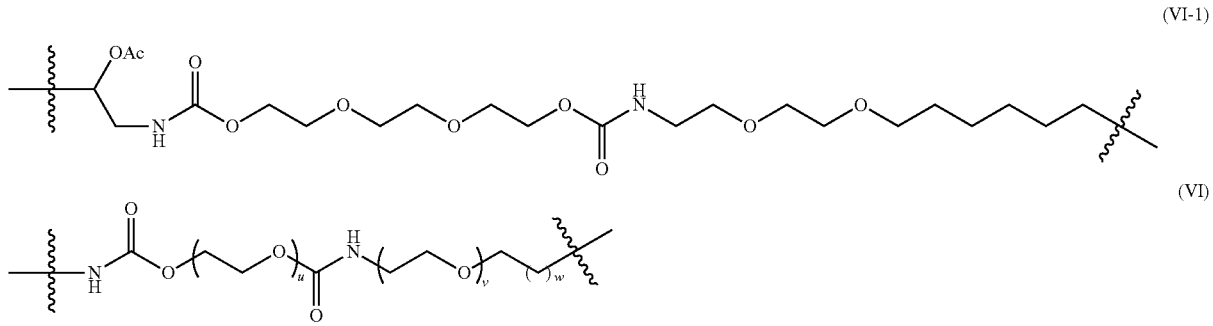

wherein u is an integer from 1 to 20, v is an integer from 0 to 20, and w is an integer from 1 to 19;

HaloTag is a Halo tag (haloalkane dehalogenase), covalently binding to the linker;

EndoS/EndoS2 is an endoglycosidase;

HisTag is a histidine tag;

wherein one or more "-Linker-HaloTag-EndoS-HisTag" moieties bind to the same support.

4. CONJUGATION DEVICE

A conjugation device disclosed in the patent application WO2022170676A or CN114480115A can be used for site-specific conjugation of N-glycosylation sites in an Fc region of an antibody and a payload, and is specifically used for the method for preparing the conjugate or the antibody-drug conjugate of the present disclosure. The conjugation device includes a flow reactor and a fluid delivery unit. An immobilized endoglycosidase is filled in the flow reactor. The fluid delivery unit is in fluid communication with an inlet of the flow reactor, and a donor containing oxazoline oligosaccharide and an antibody containing a GlcNAc motif (or a protein containing the Fc region) are transported to the flow reactor by the fluid delivery unit.

In some embodiments, the conjugation device includes: at least one flow reactor having an inlet and an outlet, the flow reactor being completely filled with a medium (such as a chromatography bead, fiber, a film or other matrices), and an endoglycosidase being immobilized on the medium;

a fluid delivery unit, being in fluid communication with the inlet of the flow reactor, and configured to continuously provide at least one reaction fluid to the flow reactor according to different stages of the conjugation process; wherein the at least one reaction fluid include a donor containing oxazoline oligosaccharide and an antibody containing a GlcNAc motif (or a protein containing an Fc region);

and a fluid collection unit, being in fluid communication with the outlet of the flow reactor, and configured to control collection of fluid flowing out of the outlet of the flow reactor according to the different stages of the conjugation process;

During the continuous flow of the at least one reaction fluid through the flow reactor, the donor containing the oxazoline oligosaccharide and the antibody containing the GlcNAc motif (or protein containing the Fc region) are subjected to a conjugation reaction under the catalysis of the endoglycosidase to generate the antibody conjugate or the conjugate.

In some embodiments, the endoglycosidase is directionally immobilized onto the medium and packed in the flow reactor, such that when the reaction fluid flows through the flow reactor, two reaction components of a conjugate to be generated included in the reaction fluid are continuously and stably conjugated.

Compared with chemical conjugation, the conjugation device of the present disclosure greatly reduces process steps, significantly reduces process complexity, and is very suitable for saving high manufacturing costs. Moreover, by using the flow reactor, linear scale-up and continuous flow production of a conjugation process can be achieved to meet industrial demands for higher yields, shorten unit conjugation time, and reduce occupied space in a manufacturing region. Bioconjugates are produced using the conjugation device, which enables site-specific conjugation between a payload-linker and an antibody (or a protein containing an Fc region), improving homogeneity and thus expanding a therapeutic window. Furthermore, the conjugation process can be integrated with a production process flow of biomolecules such as monoclonal antibodies. For example, conjugation can be done in the production stage of both a monoclonal antibody intermediate and a monoclonal antibody stock solution. Therefore, this process has high flexibility and good coherence.

In some embodiments, the at least one reaction fluid includes a first reaction fluid and a second reaction fluid, wherein the first reaction fluid includes a donor containing oxazoline oligosaccharide or an antibody containing a GlcNAc motif (or a protein containing an Fc region), and the second reaction fluid includes the antibody containing the GlcNAc motif (or the protein containing the Fc region) or the donor containing the oxazoline oligosaccharide.

In some embodiments, the conjugation process sequentially includes the following stages: pre-reaction equilibration, conjugation reaction, post-reaction recovery, and post-recovery flushing, and the fluid delivery unit is further configured to: continuously provide a buffer to the flow reactor during the pre-reaction equilibration, the post-reaction recovery, and the post-recovery flushing; and continuously and simultaneously provide the donor containing the oxazoline oligosaccharide and the antibody containing the GlcNAc motif (or the protein containing the Fc region) to the flow reactor during the conjugation reaction.

In some embodiments, the buffer, the first reaction fluid, and the second reaction fluid are stored in a first container, a second container, and a third container, respectively. The fluid delivery unit includes a first delivery pump and a second delivery pump. The first container and the second container are connected to the first delivery pump respectively via a first container outlet tube and a second container outlet tube. The third container is connected to the second delivery pump via a third container outlet tube. The first delivery pump and the second delivery pump are connected to an inlet main tube respectively via a first inlet branch tube and a second inlet branch tube. The inlet main tube is connected to the inlet of the flow reactor. Moreover, during pre-reaction equilibration, the post-reaction recovery, and the post-recovery flushing, the first delivery pump pumps the buffer in the first container into the inlet main tube. During the conjugation reaction, the first delivery pump pumps the first reaction fluid in the second container into the inlet main tube, and the second delivery pump pumps the second reaction fluid in the third container into the inlet main tube.

In some embodiments, the fluid delivery unit further includes a first valve, a second valve, a third valve, and a fourth valve. The first valve, the second valve, and the third valve are provided on the first container outlet tube, the second container outlet tube, and the third container outlet tube, respectively, and are configured to control fluid flow in the first container outlet tube, in the second container outlet tube, and in the third container outlet tube, respectively, and the fourth valve is provided on the first inlet branch tube, and is configured to control fluid flow in the first inlet branch.

In some embodiments, during the pre-reaction equilibration, the post-reaction recovery, and the post-recovery flushing, the first valve and the fourth valve are opened, the second valve and the third valve are closed; during the conjugation reaction, the first valve is closed, and the second valve, the third valve, and the fourth valve are opened.

In some embodiments, the first container outlet tube, the second container outlet tube, the third container outlet tube, the first inlet branch tube, the second inlet branch tube and the inlet main tube are disposable or non-disposable, and are each made of one of stainless steel, titanium, and silica gel. The first container, the second container, and the third container are selected from one of: a disposable liquid storage bag, a disposable liquid storage bottle, a stainless-steel container, as well as disposable and non-disposable glass or plastic containers.

In some embodiments, the fluid collection unit is further configured to: collect the fluid flowing out of the outlet of the flow reactor into the fourth container during the pre-reaction equilibration and the post-recovery flushing;
and collect the fluid flowing out of the outlet of the flow reactor into the fifth container during the conjugation reaction and the post-reaction recovery.

In some embodiments, the fourth container and the fifth container are connected to the outlet main tube respectively via a fourth container inlet tube and a fifth container inlet tube, and the outlet main tube is connected to the outlet of the flow reactor. Moreover, the fluid collection unit includes a fifth valve and a sixth valve, and the fifth valve and the sixth valve are provided on the fourth container inlet tube and the fifth container inlet tube, respectively, and are configured to control fluid flow in the fourth container inlet tube and in the fifth container inlet tube, respectively.

In some embodiments, during the pre-reaction equilibration and the post-recovery flushing, the fifth valve is opened and the sixth valve is closed; during the conjugation reaction and the post-reaction recovery, the fifth valve is closed and the sixth valve is opened.

In some embodiments, the fourth container outlet tube and the fifth container outlet tube are disposable or non-disposable, and are each made of one of stainless steel, titanium, and silica gel. The fourth container and the fifth container are selected from one of: a disposable liquid storage bag, a disposable liquid storage bottle, a stainless-steel container, as well as disposable and non-disposable glass or plastic containers.

In some embodiments, the conjugation device further includes: a temperature control unit, which is configured to: control the temperature of fluid flowing into the inlet of the flow reactor and fluid flowing out of the outlet of the flow reactor in the conjugating process.

In some embodiments, the temperature control unit includes: a heating module, which is provided at the inlet of the flow reactor to heat the fluid flowing into the inlet; and a cooling module, provided at the outlet of the flow reactor to cool the fluid flowing out of the outlet.

In some embodiments, the conjugation device further includes: a sampling detection unit, which is in fluid communication with the outlet of the flow reactor, and is configured to: collect a sample fluid from the fluid flowing out of the outlet of the flow reactor according to a predetermined sampling time; and detect a conjugate in the sample fluid to obtain a detection result, wherein the detection result indicates whether the conjugate meets a pre-defined standard or not.

In some embodiments, the sampling detection unit includes a sampling pump, a first switching valve, an elution pump, at least one analytical column, and a detector. The sampling pump is connected to the outlet of the flow reactor via the sampling tube. The first switching valve is provided with a sample loop, and the first switching valve is switched between a first state and a second state according to preset sampling time. When the first switching valve is in the first state, the sampling pump is in fluid communication with the sample loop, and collects a sample fluid from the fluid flowing out of the flow reactor via the sampling tube and pumps the same into the sample loop; when the first switching valve is in the second state, the elution pump, the sample loop, the at least one analytical column, and the detector are in fluid communication via a detection tube. The elution pump pumps an eluent into the detection tube, and the eluent is allowed to flow through the sample loop, thereby driving the sample fluid in the sample loop to flow through one of the at least one analytical column before entering the detector.

In some embodiments, there are two analytical columns, and the sampling detection unit further includes a second switching valve and a cleaning pump. The second switching valve is switched between the two states. When the second switching valve is in any of the two states, the sample loop and the detector are in fluid communication with one of the two analytical columns. The eluent drives the sample fluid in the sample loop to flow into the analytical column, and the cleaning pump is in fluid communication with the other of the two analytical columns, and a buffer is pumped to the other analytical column to equilibrate the analytical column.

In some embodiments, the first switching valve is a six-way valve, the second switching valve is a ten-way valve, and the elution pump is a quaternary pump.

In some embodiments, the conjugation device further includes: a recycling unit, which is provided between the inlet and outlet of the flow reactor. When the detection result indicates that the conjugate does not meet the predefined standard, the fluid collection unit is configured to stop collecting the fluid flowing out of the outlet of the flow reactor, and the recycling unit is configured to control the fluid flowing out of the outlet of the flow reactor to re-enter the inlet to carry out the conjugation reaction again in the flow reactor.

In some embodiments, the recycling unit includes a seventh valve, which is provided on a recovery tube. The recovery tube is connected between the inlet and the outlet of the flow reactor, and a recovery container is provided on the recovery tube. When the detection result indicates that the conjugate does not meet the predefined standard, the seventh valve is opened, and the fluid flowing out of the outlet of the flow reactor flows through the recovery tube and recovery container before entering the inlet.

In some embodiments, the flow reactor is a conjugation column (i.e. a prepacked column).

In some embodiments, the conjugation device further includes at least one module selected from the group consisting of: a pressure sensing module, a flow detection module, a pH metering module, a conductivity metering module and a UV detection module, pressure sensing module, a flow detection module, a pH metering module, a conductivity metering module and a UV detection module. In some embodiments, the modules can be provided at the inlet and/or the outlet.

Patent application WO2022170676A or CN114480115A is incorporated in its entirety in this application by reference.

DETAILED DESCRIPTION

The present disclosure will be further described below with embodiments, but does not limit the present disclosure to the scope of the embodiments described. Experimental methods for which specific conditions are not specified in the following embodiments are selected according to conventional methods and conditions, or according to descriptive literature.

Instruments, Materials, and Reagents

Unless otherwise specified, instruments and reagents used in the embodiments are commercially available. The reagent can be used directly without further purification.

Ni Sepharose 6 FF: a metal chelate affinity chromatography medium, also referred to as immobilized metal ion affinity chromatography, the principle of which is that some amino acids, such as histidine, tryptophan and cysteine, on a protein surface, can have special interaction with metal ions ($Cu^{2+}$, $Zn^{2+}$, $Ni^{2+}$, $Co^{2+}$, and $Fe^{3+}$), thereby isolating proteins. These actions include coordinate bond binding, electrostatic adsorption, and covalent bond binding, with covalent bond bonding being the main one, and of these, a 6-histidine tag (His Tag) is most widely used.

Q Sepharose FF/Capto S impact: isolation of molecules by ion exchange is based on differences in surface electrostatic charges. The protein consists of many different amino acids containing weak acid and weak base groups. The surface static charges will gradually change with the pH of the surrounding environment. That is, a protein molecule is an amphoteric molecule. In the process of ion exchange chromatography isolation, binding and elution of particular molecules are achieved by controlling reversible interaction between charged molecules and ion exchange packing with opposite charges, thereby achieving the effect of isolation. A protein in an environment with the same pH value as an isoelectric point has zero surface static charge, and thus, will not interact with charged packing. When the pH value of the environment is higher than its isoelectric point, the protein will bind to positively charged packing, namely an anion exchanger. While when the pH value of the environment is lower than its isoelectric point, the protein will bind to negatively charged packing, namely a cation exchanger.

SDS-PGAE: sodium dodecyl sulfate-polyacrylamide gel electrophoresis (SDS-PAGE), wherein SDS is an anionic detergent. As a denaturant and cosolvent, SDS can break the intramolecular and intermolecular hydrogen bonds, and removes intramolecular hydrophobic interaction to unfold molecules, and destroy secondary and tertiary structures of the protein molecules. SDS binds to a denatured protein to make the denatured protein negatively charged. The amount of SDS bound to the denatured protein is proportional to molecular weight. In a case of saturation, each gram of protein can bind to 1.4 g of SDS. The negative charges carried greatly exceed the amount of original charge of the protein, eliminating charge differences and structural differences between different molecules. Therefore, the mobility of an SDS-protein complex in acrylamide gel electrophoresis is only related to the size of the protein. Strong reducing agents (such as β-mercaptoethanol and dithiothreitol) can open intramolecular and intermolecular disulfide bonds, making protein isolation more effective.

Example 1: Preparation of Endoglycosidase Fusion Protein 1.1 Amino Acid Sequence of Halo-EndoS2-His (Halo is Marked With a Single Underline, His Tag is Italicized, and GGGGSGGGGS is a Linker Sequence)

(SEQ ID NO: 1)
MAEIGTGFPFDPHYVEVLGERMHYVDVGPRDGTPVLFLHGNPTSSYVWR

NIIPHVAPTHRCIAPDLIGMGKSDKPDLGYFFDDHVRFMDAFIEALGLE

EVVLVIHDWGSALGFHWAKRNPERVKGIAFMEFIRPIPTWDEWPEFARE

TFQAFRTTDVGRKLIIDQNVFIEGTLPMGVVRPLTEVEMDHYREPFLNP

VDREPLWRFPNELPIAGEPANIVALVEEYMDWLHQSPVPKLLFWGTPGV

LIPPAEAARLAKSLPNCKAVDIGPGLNLLQEDNPDLIGSEIARWLSTLE

ISGGGGGSGGGGSMDKHLLVKRTLGCVCAATLMGAALATHHDSLNTVKA

EEKTVQTGKTDQQVGAKLVQEIREGKRGPLYAGYFRTWHDRASTGIDGK

QQHPENTMAEVPKEVDILFVFHDHTASDSPFWSELKDSYVHKLHQQGTA

LVQTIGVNELNGRTGLSKDYPDTPEGNKALAAAIVKAFVTDRGVDGLDI

DIEHEFTNKRTPEEDARALNVFKEIAQLIGKNGSDKSKLLIMDTTLSVE

NNPIFKGIAEDLDYLLRQYYGSQGGEAEVDTINSDWNQYQNYIDASQFM

IGFSFFEESASKGNLWFDVNEYDPNNPEKGKDIEGTRAKKYAEWQPSTG

GLKAGIFSYAIDRDGVAHVPSTYKNRTSTNLQRHEVDNISHTDYTVSRK

LKTLMTEDKRYDVIDQKDIPDPALREQIIQQVGQYKGDLERYNKTLVLT

GDKIQNLKGLEKLSKLQKLELRQLSNVKEITPELLPESMKKDAELVMVG

MTGLEKLNLSGLNRQTLDGIDVNSITHLTSFDISHNSLDLSEKSEDRKL

LMTLMEQVSNHQKITVKNTAFENQKPKGYYPQTYDTKEGHYDVDNAEHD

ILTDFVFGTVTKRNTFIGDEEAFAIYKEGAVDGRQYVSKDYTYEAFRKD

YKGYKVHLTASNLGETVTSKVTATTDETYLVDVSDGEKVVHHMKLNIGS

-continued

```
GAIMMENLAKGAKVIGTSGDFEQAKKIFDGEKSDRFFTWGQTNWIAFDL

GEINLAKEWRLFNAETNTEIKTDSSLNVAKGRLQILKDTTIDLEKMDIK

NRKEYLSNDENWTDVAQMDDAKAIFNSKLSNVLSRYWRFCVDGGASSYY

PQYTELQILGQRLSNDVANTLKDHHHHHHHHHH
```

1.2 Halo-Endo S2-His Clone

A nucleic acid sequence coding Halo-Endo S2-His was synthesized using a standard gene synthesis method, and was inserted into a pET expression vector. A Halo-Endo S2-His expression plasmid was transformed into *Escherichia coli* BL21 (DE3). A corresponding antibiotic was added into a Luria-Bertani (LB) medium, culture was performed at 37° C. until OD600=0.5-1.0, and bacteria was preserved.

1.3. Halo-Endo S2-His Tag Purification (Reactor)

A glycerol stock was taken out, inoculated into an LB liquid medium containing a corresponding antibiotic and subjected to shaking culture at 100 to 300 rpm and 37° C. for 2 to 8 h. When OD600 reached 0.5 to 1.0, the cultured glycerol stock was inoculated into a 10 L reactor and cultured for 5 to 10 h. Then IPTG was added to final concentration of 0.2 mM, and induced expression was performed overnight at 16 degrees Celsius. Centrifuging was performed at 2° C. to 8° C. at 3000 to 5000 rpm for 10 to 30 min, and bacterial precipitates were collected. An equilibration buffer was added to resuspend cells, and the resuspended cells were disrupted under high pressure. Centrifuging was performed at 2° C. to 8° C. at 5000 to 10,000 rpm for 10 to 60 min to isolate supernatant and the precipitates; and Ni column affinity purification was performed. An Ni chromatography column was connected to a protein purification system, and was first thoroughly washed with purified water and the equilibration buffer. The supernatant was loaded at a low flow rate. Washing was performed with the equilibration buffer and 80 mM imidazole buffer, and elution was performed with 500 mM imidazole buffer. Performed SDS-PAGE Detection Analysis.

As shown in FIG. 1, Halo-Endo S2-His was attached by Ni magnetic beads, and there was no sample of interest in flow-through. The Halo-Endo S2-His was eluted under the condition of 500 mM imidazole. This result indicates that the Halo-Endo S2-His can be subjected to scaled-up culture by a reactor, and linear production scale-up can be achieved by an Ni chromatography column.

Example 2. Preparation of Immobilized Halo-Endo S2-His

Preparation Flow 2.1. Preparation of Chloroalkyl-Linker Modified Resin (Chloro Resin)

For methods for preparing chloro resin see, for example, U.S. Pat. Nos. 7,429,472, 7,888,086 and 8,202,700, all of which are incorporated herein by reference. Resin used in the preparation of the chloro resin is shown in Table 1.

TABLE 1

| Resin | | |
|---|---|---|
| | Resin | Numbering |
| 1 | NHS-activated Bestaresin 4FF (Highly cross-linked agarose, Bestchrom) | HX17091 |
| 2 | CNBr-activated Bestaresin (Highly cross-linked agarose, Bestchrom) | HX17092 |
| 3 | Epoxy-activated resin (Polymethyl methacrylate, Nano-Micro) | HX17093 |
| 4 | Epoxy-activated Bestaresin 4FF (Highly cross-linked agarose, Bestchrom) | HX17094 |

Method:

(1) Pretreatment

For NHS-activated resin (Bestchrom) and CNBr-activated resin (Bestchrom):
the resin was filtered with isopropanol, and a filter cake was washed with DMF (N, N-dimethylformamide) once, followed by draining. The filter cake was transferred into a flask with DMF and stirred. Next, ethylenediamine was added into the mixture and stirred for 10 to 15 h. Filtration was performed and the filter cake was washed with DMF. Then liquid was drained off.

For epoxy-activated resin:
the resin was filtered with isopropanol, and a filter cake was washed with $H_2O$ once, followed by draining. The filter cake was transferred into a flask and stirred. Next, 25% to 28% concentrated ammonia water was added into the mixture, the system was slowly heated to 40° C. to 50° C., and a reaction was carried out with stirring at 40° C. to 50° C. The temperature of the system was lowered to 20° C. to 30° C., and the mixture was filtered. The filter cake was washed with $H_2O$ until the pH of a filtrate reached about 7 to 8. Next, the filter cake was washed with DMF, and liquid was drained off.

(2) The filter cake from step (1) was transferred into a flask and stirred. Next, DMF containing the chloroalkyl substrate with the structure of formula (III-1) and triethylamine were added into the system in sequence. A reaction was carried out with stirring. Next, the system was filtered and the filter cake was washed with DMF. Finally, liquid was drained off:

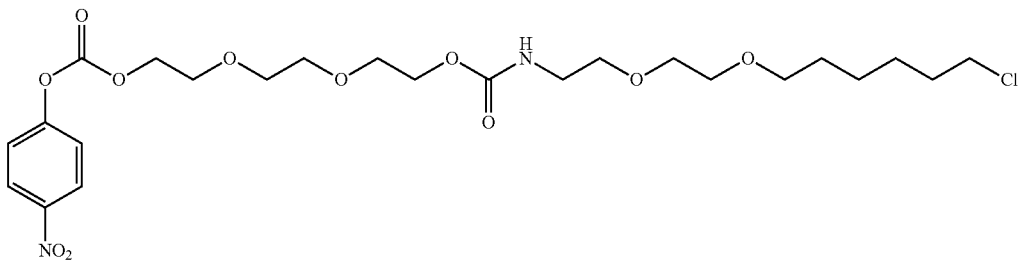

(III-1)

(3) The filter cake from step (2) was transferred into a flask. The flask was opened, and stirring was performed. Next, Ac₂O and triethylamine were added into the mixture in sequence. A reaction was carried out with stirring. Then, the mixture was filtered, and the filter cake was washed with DMF. Then, the filter cake was washed with H₂O, and liquid was drained off. Finally, the mixture was transferred with 20% ethanol into a container for storage.

Result: chloro resin with a structure of formula (IV-1) was obtained:

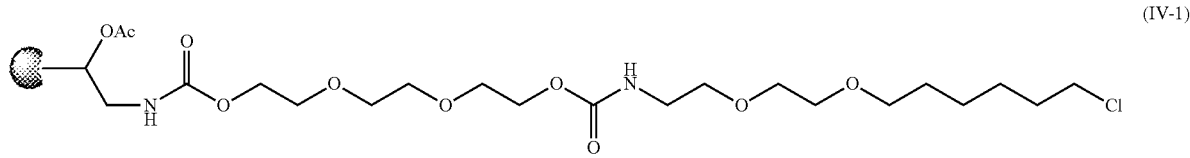 [SMILES: CC(=O)OC(C)CNC(=O)OCCOCCOCCOC(=O)NCCOCCOCCCCCCCl]

(IV-1)

wherein ⬤ is highly cross-linked agarose resin or polymethyl methacrylate resin.

Halo-Endo S2-His was mixed with the chloro resin at room temperature, and the mixture was incubated for 10 min to 24 h. A step of washing was performed with 20 mM Tris HCl, 150 mM NaCl, and a buffer with a pH of 6.0 to 10.0, and was repeated three times. The immobilized endoglycosidase fusion protein (Halo-Endo S2-His was covalently attached to the chloro resin) was detected for activity. After passing detection, the immobilized endoglycosidase fusion protein was washed with 20 mM Tris HCl and 150 mM NaCl, and finally stored at 2° C. to 8° C.

2.2. Immobilized Enzyme Load

1) Various types of chloro resin (250 μl) were taken; excess glycosidase was added; the mixture was placed on a rotary mixer; immobilization was performed at room temperature for 2 h;

2) in the immobilization process of Halo-Endo S2-His, supernatant of the immobilized enzyme was taken at 15 min, 30 min, 1 h, and 2 h. Centrifuging was performed at 3000 g at room temperature for 3 min each time. The supernatant was taken by suction, and the concentration of the enzyme in the supernatant was detected using a Nanodrop ultraviolet spectrophotometer; and 3) the concentration of the endoglycosidase at each time point was calculated, the immobilization amount of the enzyme at each timed moment was calculated by subtracting the concentration at each time point from the initial concentration of the enzyme, and a load change curve of the immobilization process of a Halo-Endo S2-His medium was plotted.

Figure 2:
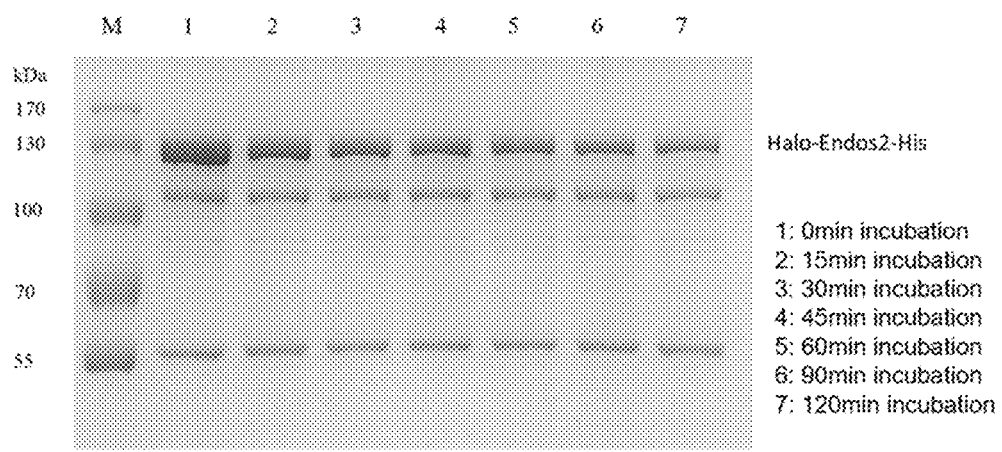
FIG. 2 is an SDS-PAGE electropherogram showing supernatant of the immobilized endoglycosidase fusion protein (Halo-Endo S2-His) of the present disclosure at different incubation times.

Protein trend changes in the supernatant were detected by SDS-PAGE. As shown in FIG. 2, the results show that the Halo-Endo S2-His in the supernatant become less and less over time, and is specifically immobilized to the chloro resin.

Example 3. Preparation of Liner-Payload 3.1. Preparation of Disaccharide Substrate Preparation of Disaccharide Substrate Compound 1

Compound 1 was prepared by employing the following steps, with a structure as follows:

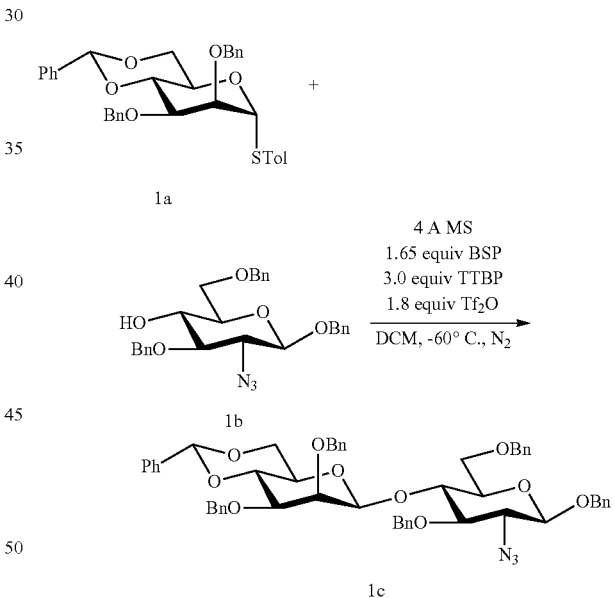

(1) Preparation of Compound 1c

Under the condition of vacuumizing with an oil pump, a 100 mL Schlenk reaction flask was baked with a heat gun for 5 min, a pre-activated molecular sieve was added after cooling, and baking was performed for another 5 min. The system was vacuumized for nitrogen displacement three times; compound 1a (4.41 g, 7.96 mmol) was added into the system under nitrogen protection, and stirred for 3 min, and then anhydrous dichloromethane (30 mL) was added and stirred for 0.5 h. In addition, following the same operations, compound 1b (1.89 g, 3.98 mmol, dissolved in 20 mL of anhydrous dichloromethane) was added into another 50 mL Schlenk reaction flask into which the activated molecular sieve had been added, and stirred for 1 h, and pre-drying was performed to remove residual water from the system.

Under nitrogen protection, 1-(phenylsulfinyl) piperidine (BSP, 1.37 g, 6.56 mmol) and 2,4,6-tri-tert-butylpyrimidine (TTBP, 2.94 g, 11.94 mmol) were added to a solution of the above-mentioned dried compound 1a at room temperature and stirred for another 20 min. The reaction flask was placed in a dry ice/ethyl acetate bath, and cooled to −65° C., and trifluoromethanesulfonic anhydride (1.2 mL, 7.16 mmol) was added into the system. After 2 min, a dichloromethane solution of the previously pre-dried compound 1b was added into the system, and the resulting reaction mixture was stirred at −65° C. until the reaction ended as detected by TLC (developing solvent: EtOAc/PE=1/8) (about 3 h). A saturated sodium bicarbonate solution was added to the system for a quenching reaction. Extraction and liquid separation were performed with dichloromethane (150 mL×3), merged organic phases were washed in sequence with water and a saturated salt solution, dried over anhydrous sodium sulfate, filtered, concentrated under reduced pressure, wet loaded and isolated by column chromatography (eluent: EtOAc/PE=1/12-1/10), to afford compound 1c (2.72 g, yield 75.4%, colorless viscous oily liquid). $^1$H NMR (400 MHz, chloroform-d) δ 7.55 (dd, J=7.6, 2.1 Hz, 2H), 7.51-7.28 (m, 28H), 5.60 (s, 1H), 5.14 (d, J=10.4 Hz, 1H), 5.00 (d, J=12.0 Hz, 1H), 4.94 (d, J=11.8 Hz, 1H), 4.90-4.80 (m, 2H), 4.76 (d, J=12.0 Hz, 1H), 4.74-4.63 (m, 3H), 4.57 (s, 1H, H$^1$), 4.48 (d, J=12.1 Hz, 1H), 4.37 (d, J=8.1 Hz, 1H, H$^1$), 4.22-4.10 (m, 2H), 4.05 (t, J=9.3 Hz, 1H), 3.80 (d, J=3.1 Hz, 1H), 3.72 (dd, J=11.2, 2.2 Hz, 1H), 3.67-3.52 (m, 3H), 3.49 (dd, J=9.8, 3.1 Hz, 1H), 3.41 (t, J=9.3 Hz, 1H), 3.35 (dt, J=9.8, 2.9 Hz, 1H), 3.16 (td, J=9.7, 4.8 Hz, 1H). MS (ESI) m/z of $C_{54}H_{56}N_3O_{10}^+$[M+H]$^+$: calc 906.4, found 906.7.

(2) Preparation of Compound 1d

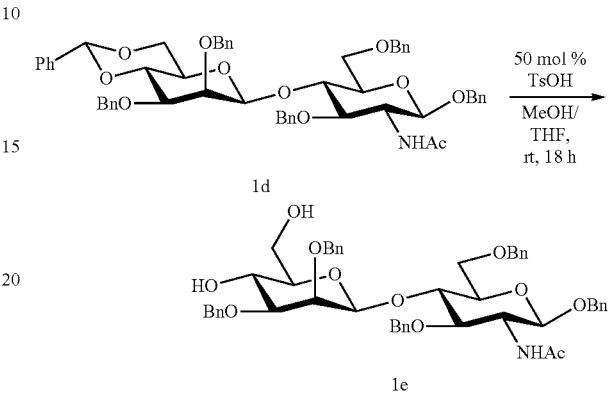

To a 25 mL Schlenk reaction flask were added the compound 1c (228 mg, 0.252 mmol), chloroform (1.2 mL), pyridine (1 mL) and AcSH (1.2 mL) in sequence at room temperature for dissolution. The reaction flask was sealed with a sleeve stopper septum, and the system was stirred at 60° C. until the reaction basically ended as detected by HPLC, which took about 18 h. Most of the solvents were removed after concentration under reduced pressure, then ethyl acetate (50 mL) was added into the system, the resulting mixture was washed with a saturated sodium bicarbonate solution (30 mL), 1 M hydrochloric acid (10 mL×4) and a saturated sodium bicarbonate solution (30 mL) in sequence, organic phases were dried over anhydrous sodium sulfate, and purified by column chromatography (eluent: EtOAc/PE=1/10-1/1) after concentration under reduced pressure to afford compound 1d (200 mg, yield 86%, white solid). $^1$H NMR (400 MHz, chloroform-d) δ 7.57-7.49 (m, 2H), 7.48-7.39 (m, 5H), 7.39-7.24 (m, 23H), 5.80 (d, J=8.1 Hz, 1H), 5.59 (s, 1H), 5.00 (d, J=6.7 Hz, 1H), 4.97-4.87 (m, 3H), 4.87-4.75 (m, 2H), 4.69-4.59 (m, 4H), 4.57 (s, 1H), 4.45 (d, J=12.0 Hz, 1H), 4.19-4.05 (m, 3H), 3.96 (t, J=7.3 Hz, 1H), 3.85-3.76 (m, 2H), 3.73-3.59 (m, 4H), 3.49 (dd, J=9.8, 3.1 Hz, 1H), 3.18 (td, J=9.7, 4.8 Hz, 1H), 1.77 (d, J=1.2 Hz, 3H). MS (ESI) m/z of $C_{56}H_{60}NO_{11}^+$ [M+H]$^+$: calc 922.4, found 922.4.

(3) Preparation of Compound 1e

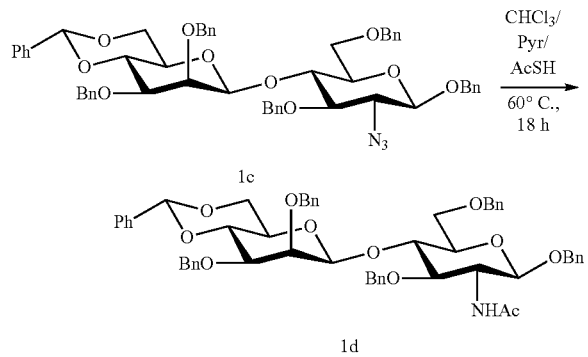

To a 100 mL single-neck flask were added the compound 1d (168 mg, 0.168 mmol), p-toluenesulfonic acid monohydrate (35 mg, 0.168 mmol), methanol (5 mL), and tetrahydrofuran (5 mL) in sequence at room temperature. Nitrogen replacement was performed three times, and the reaction was stirred overnight at room temperature until the reaction ended as detected by HPLC. The reaction system was quenched with saturated sodium bicarbonate solution (20 mL). Extraction and liquid separation were performed with dichloromethane (20 mL×3), merged organic phases were dried over anhydrous sodium sulfate, filtered, concentrated under reduced pressure, and purified by column chromatography (eluent: MeOH/DCM=1/20) to afford compound 1e (136 mg, yield 89%, white solid). $^1$H NMR (400 MHz, chloroform-d) δ 7.43-7.24 (m, 29H), 5.76 (d, J=7.9 Hz, 1H), 5.01 (d, J=6.9 Hz, 1H), 4.94 (dd, J=11.8, 2.3 Hz, 2H), 4.85 (d, J=11.7 Hz, 1H), 4.77 (d, J=11.8 Hz, 1H), 4.70-4.59 (m, 3H), 4.58-4.47 (m, 3H), 4.36 (d, J=11.7 Hz, 1H), 4.20 (t, J=7.9 Hz, 1H), 3.94 (t, J=7.5 Hz, 1H), 3.91-3.80 (m, 3H), 3.80-3.71 (m, 3H), 3.63-3.50 (m, 2H), 3.22-3.14 (m, 2H), 1.78 (s, 3). MS (ESI) m/z of $C_{49}H_{56}NO_{11}^+$ [M+H]$^+$: calc 834.4, found 834.5.

(4) Preparation of Compound 1f

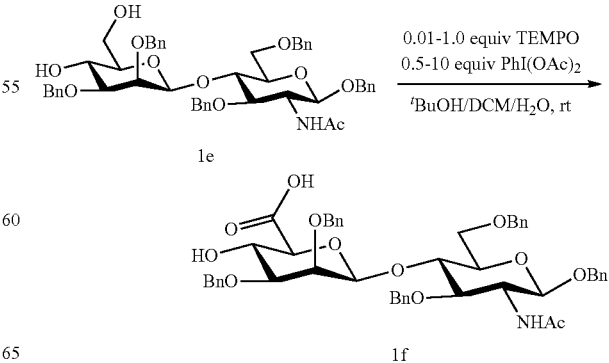

To a 100 mL single-neck flask were added the compound 1e (130 mg, 0.156 mmol), dichloromethane, tert-butanol and water in sequence at room temperature. Iodobenzene diacetate (0.5 to 10 equiv.) and 2,2,6,6-tetramethyl-1-piperidine oxide (0.01 to 1 equiv.) were added into the system, and the reaction was stirred overnight at room temperature until the reaction ended as detected by TLC. Extraction and liquid separation were performed with dichloromethane, merged organic phases were dried over anhydrous sodium sulfate, filtered, concentrated, and purified by column chromatography to afford compound 1f (100 mg, yield 75.1%, white solid). $^1$H NMR (400 MHz, chloroform-d) δ 7.42-7.31 (m, 18H), 7.30-7.27 (m, 2H), 7.25-7.20 (m, 3H), 7.15 (dd, J=6.7, 2.9 Hz, 2H), 6.06 (d, J=8.3 Hz, 1H), 4.96 (d, J=6.6 Hz, 1H), 4.93 (d, J=11.9 Hz, 1H), 4.86 (d, J=11.1 Hz, 1H), 4.81 (d, J=12.1 Hz, 1H), 4.73 (d, J=11.1 Hz, 1H), 4.71-4.65 (m, 3H), 4.65-4.57 (m, 3H), 4.49 (s, 1H), 4.46 (d, J=12.0 Hz, 1H), 4.23 (t, J=7.1 Hz, 1H), 4.15 (t, J=9.5 Hz, 1H), 3.89 (t, J=6.5 Hz, 1H), 3.86-3.65 (m, 6H), 3.54 (d, J=9.7 Hz, 1H), 3.30 (dd, J=9.3, 2.8 Hz, 1H), 1.65 (s, 3H). MS (ESI) m/z of $C_{49}H_{52}NO_{12}^-$ [M−H$^+$]$^-$: calc 846.3, found 846.3.

(5) Preparation of Compound 1

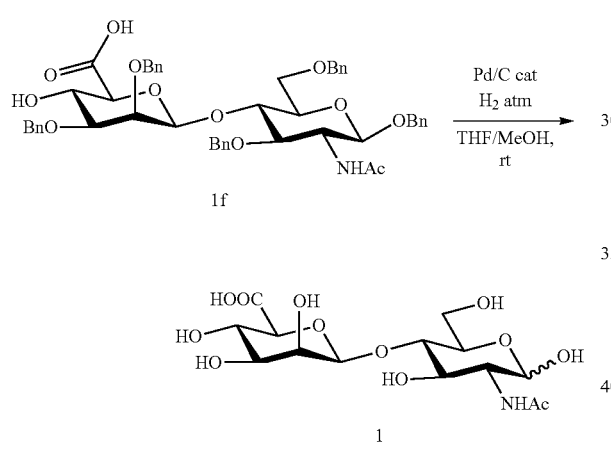

To a 50 mL single-neck flask were added the compound 1f (160 mg, 0.189 mmol), tetrahydrofuran, methanol, and palladium-carbon catalyst in sequence at room temperature, and the reaction system was stirred under a hydrogen atmosphere until all raw materials disappeared as detected by TLC. Filtration, concentration under reduced pressure, draining with oil pump were performed to afford compound 1 (75 mg, yield 100%, white solid). MS (ESI) m/z of $C_{14}H_{22}NO_{12}^-$ [M−H$^+$]$^-$: calc 396.1, found 396.1.

Preparation of Disaccharide Substrate Compound 2

Compound 2 was prepared by employing the following steps, with a structure as follows:

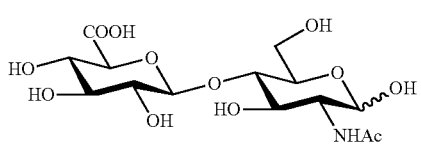

(1) Synthesis of Compound 2-1

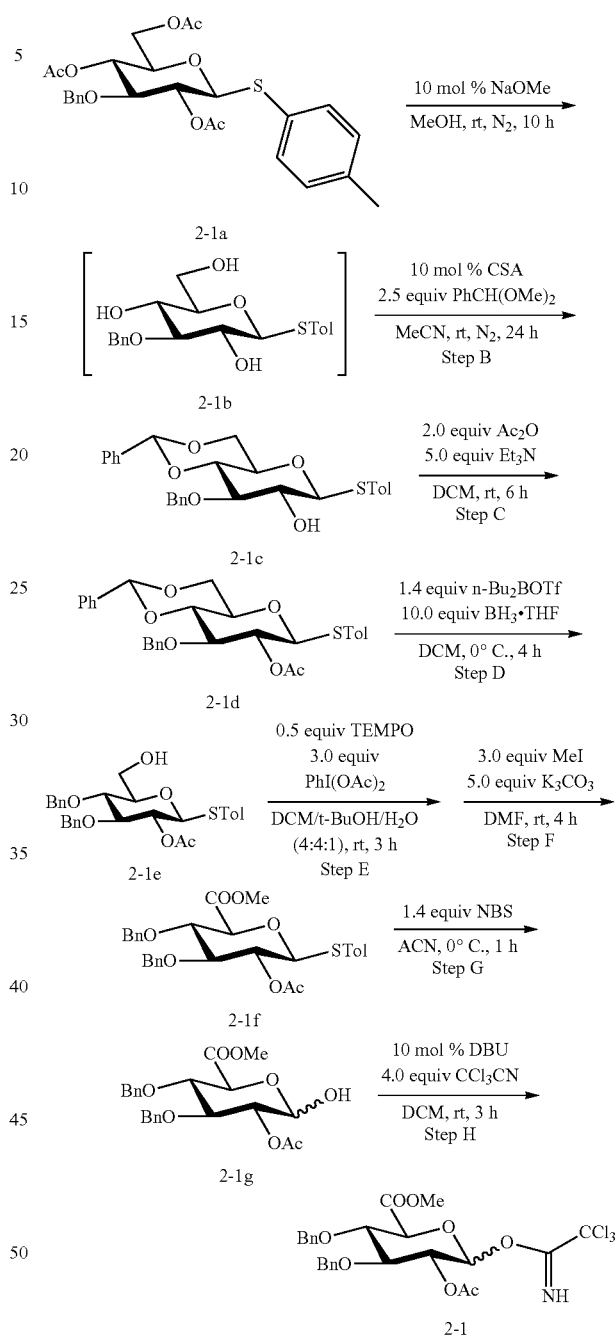

Step A: Synthesis of Compound 2-1b

Compound 2-1a (1.0 equiv., commercially available, CAS: 959153-39-0), MeOH and sodium methoxide (0.1 equiv., 5 mol/L in MeOH) were added into a single-neck flask and stirred at room temperature under a nitrogen atmosphere. The extent of reaction was monitored by TLC. After the reaction was completed, 1 M hydrochloric acid was added to quench the reaction and the reaction was regulated to neutral. The solvent was removed under reduced pressure, and a little toluene was added. Water was removed using azeotropic effect under the condition of rotary evaporation under reduced pressure to afford crude product 2-1b as light yellow viscous oily liquid, and the crude product was directly used for a next reaction without further purification.

Step B: Synthesis of Compound 2-1c

To a single-neck flask were added crude product 2-1b (1 equiv.), acetonitrile, camphorsulfonic acid (0.1 equiv.) and benzaldehyde dimethyl acetal (4 equiv.) in sequence, and the reaction system was stirred overnight at room temperature. The extent of reaction was monitored by TLC. After the reaction was completed (about 24 h), a saturated sodium bicarbonate solution was added into the system to quench the reaction; extraction and liquid separation were performed with ethyl acetate, and merged organic phases were washed with water and a saturated salt solution, dried over anhydrous sodium sulfate, filtered, concentrated, wet loaded, and purified by column chromatography on silica gel (eluent: PE/EtOAc=5:1) to afford 2-1c (white solid, yield 83%). $^1$H NMR (400 MHz, chloroform-d) δ 7.51-7.49 (m, 2H, Ar—H), 7.45 (d, J=8.0 Hz, 2H, Ar—H), 7.42-7.37 (m, 5H, Ar—H), 7.36-7.31 (m, 3H, Ar—H), 7.15 (d, J=8.0 Hz, 2H, Ar—H), 5.56 (s, 1H, PhCH), 4.97 (d, J=11.6 Hz, 1H, PhCH$_2$), 4.81 (d, J=11.6 Hz, 1H, PhCH$_2$), 4.58 (d, J=9.6 Hz, 1H), 4.40 (dd, J=10.2, 4.8 Hz, 1H), 3.80 (dd, J=10.0, 10.4 Hz, 1H), 3.70 (dd, J=9.2, 9.2 Hz, 1H), 3.65 (dd, J=9.2, 9.2 Hz, 1H), 3.53-3.48 (m, 2H), 2.64 (br s, 1H, —OH), 2.36 (s, 3H). MS (ESI) m/z of $C_{27}H_{29}O_5S^+$ [M+H]$^+$: calc 465.2, found 465.3. $^1$H NMR data was consistent with that reported in the literature, see compound 2b1 in Nature 2007, 446, 896.

Step C: Synthesis of Compound 2-1d

To a single-neck flask were added 2-1c (1 equiv.), dichloromethane, and triethylamine (5 equiv.) in sequence. The system was cooled to 0° C., followed by acetic anhydride (2 equiv.), and the reaction was stirred for 10 min, and then the reaction system rose to room temperature and was stirred. The extent of reaction was monitored by TLC. After the reaction was completed (about 6 h), a saturated sodium bicarbonate solution was added into the system to quench the reaction. Extraction and liquid separation were performed with dichloromethane, and merged organic phases were washed with water and a saturated salt solution, dried over anhydrous sodium sulfate, filtered, concentrated, wet loaded, and purified by column chromatography (eluent: PE/EtOAc=5:1) to afford 2-1d (white solid, yield 89%). $^1$H NMR (400 MHz, chloroform-d) δ 7.51-7.48 (m, 2H, Ar—H), 7.43-7.36 (m, 5H, Ar—H), 7.34-7.25 (m, 5H, Ar—H), 7.13 (d, J=8.0 Hz, 2H, Ar—H), 5.58 (s, 1H, PhCH), 5.00 (dd, J=8.0, 8.0 Hz, 1H, H-2), 4.87 (d, J=12.0 Hz, 1H, PhCH$_2$), 4.67 (d, J=12.0 Hz, 1H, PhCH$_2$), 4.64 (d, J=10.4 Hz, 1H, H-1), 4.39 (dd, J=10.8 Hz, J=5.2 Hz, 1H), 3.81 (t, J=10.4 Hz, 1H), 3.78-3.70 (m, 2H), 3.48 (ddd, J=9.6, 5.4, 10.0 Hz, 1H), 2.35 (s, 3H, Ar—CH$_3$), 2.05 (s, 3H, OAc). MS (ESI) m/z of $C_{29}H_{31}O_6S^+$ [M+H]$^+$: calc 507.2, found 507.4. $^1$H NMR data was consistent with that reported in the literature, see compound 3b1 in Nature 2007, 446, 896.

Step D: Synthesis of Compound 2-1e

To a 100 mL two-neck flask, were added the compound 2-1d (1 equiv.), dichloromethane, and borane tetrahydrofuran (10 equiv., 1 M in THF) in sequence under a nitrogen atmosphere. The system was cooled to 0° C., followed by the addition of dibutylboron trifluoromethanesulfonate (1.4 equiv., 1.0 M in DCM). The system was maintained at 0° C. until TLC showed that the reaction was completed (about 5 h). Subsequently, a triethylamine solution was added into the system at 0° C. to quench the t dibutylboron trifluoromethanesulfonate in the system. Then methanol was slowly added dropwise to quench the borane tetrahydrofuran. After the system no longer produces a large number of bubbles, water was added to fully quench the reaction mixture. Then, extraction and liquid separation were performed with ethyl acetate, and merged organic phases were washed with water and a saturated salt solution, dried over anhydrous sodium sulfate, filtered, concentrated, and wet loaded, and purified by rapid column chromatography (eluent: eluent: PE/EtOAc=4:1) to afford crude product 2-1e (white solid). It was confirmed by LCMS that the product was structurally correct. MS (ESI) m/z of $C_{29}H_{33}O_6S^+$ [M+H]$^+$: calc 509.2, found 509.3. The crude product was directly used for a next reaction without fine purification.

Step E/F: Synthesis of Compound 2-1f

Step E: To a single-neck flask were added 2-1e (1 equiv.), iodosobenzene diacetate (3 equiv.), TEMPO (0.5 equiv.) and tert-butanol/dichloromethane/water (volume ratio: 4:4:1) in sequence, and the resulting mixed system was stirred at room temperature. The extent of reaction was monitored by TLC (developing solvent: PE/EtOAc=2/1, containing 1 v/v % acetic acid). After the reaction was complete, saturated sodium thiosulfate was added into the system to quench the reaction. Extraction and liquid separation were performed with dichloromethane, and merged organic phases were washed with water and a saturated salt solution, dried over anhydrous sodium sulfate, filtered, and concentrated, and the resulting carboxylic acid intermediate was directly used for a next reaction without further purification.

Step F: The resulting carboxylic acid intermediate in the previous step was dissolved in DMF. Iodomethane (3 equiv.) and potassium carbonate (5 equiv.) were added, and the mixture was stirred at room temperature. The extent of reaction was monitored by TLC (developing solvent: PE/EtOAc=5/1). After the reaction was completed (about 2 h), water was added into the system. Extraction and liquid separation were performed with ethyl acetate, and organic phases were washed with water and saturated salt, dried over anhydrous sodium sulfate, filtered, concentrated, and purified by column chromatography (eluent: PE/EtOAc=7:1) to afford compound2-1f (white solid, total yield of 59% in three steps). $^1$H NMR (400 MHz, chloroform-d) δ, 7.42-7.26 (m, 12H, Ar—H), 7.16 (d, J=7.6 Hz, 2H, Ar—H), 5.02 (dd, J=8.4, 8.0 Hz, 1H), 4.83 (d, J=11.6 Hz, 1H, PhCH$_2$), 4.79 (d, J=11.2 Hz, 1H, PhCH$_2$), 4.70 (d, J=11.6 Hz, 1H), 4.64 (d, J=11.2 Hz, 1H), 4.62 (d, J=10.0 Hz, 1H), 3.97 (d, J=10.0 Hz, 1H), 3.90 (dd, J=8.4, 8.0 Hz, 1H), 3.79 (s, 3H, OMe), 3.72 (dd, J=8.8, 8.8 Hz, 1H), 2.38 (s, 3H, Ar—CH$_3$), 2.04 (s, 3H, OAc). MS (ESI) m/z of $C_{30}H_{33}O_7S^+$ [M+H]$^+$: calc 537.2, found 537.4.

Step G: Synthesis of Compound 2-1g

To a 50 mL single-neck flask were added 2-1f (1.0 equiv.) and acetone in sequence. The system was cooled to 0° C. N-bromobutanimide (1.4 equiv.) was added. The mixture was stirred at 0° C. for about 1 h. TLC (developing solvent: PE/EtOAc=4/1) showed that the reaction was completed. A saturated sodium thiosulfate solution was added into the system to quench the reaction; acetone was removed by rotary evaporation under reduced pressure; water was added; and extraction and liquid separation were performed with ethyl acetate. Organic phases were merged, and washed with water and a saturated salt solution, dried over anhydrous sodium sulfate, filtered, wet loaded, and purified by column chromatography (eluent: PE/EtOAc=6:1) to afford compound 2-1g (white solid, yield 90%). MS (ESI) m/z of $C_{23}H_{27}O_8^+$ [M+H]$^+$: calc 431.2, found 431.5.

Step H: Synthesis of Compound 2-1

To a 50 mL single-neck flask were added 2-1g (1 equiv.), 1,8-diazabicyclo[5.4.0]undec-7-ene (DBU, 0.1 equiv.) and dichloromethane in sequence under a nitrogen atmosphere. The system was cooled to 0° C. and well stirred. Subsequently, trichloroacetonitrile (4equiv.) was added; the ice water bath was removed and the system naturally rose to room temperature and stirred; the reaction was monitored by TLC (developing solvent: PE/EtOAc=2/1); after the reaction was completed (about 2 h), the solvent was removed by rotary evaporation under reduced pressure, and wet loading and purification by column chromatography (eluent: PE/EtOAc=4:1) were performed to afford compound 2-1 (light yellow viscous oily liquid, yield 87%). MS (ESI) m/z of $C_{23}H_{25}O_7^+$ $[M–Cl_3CC(NH)O^-]^+$: calc 413.2, found 413.2.

(2) Synthesis of Compound 2-2

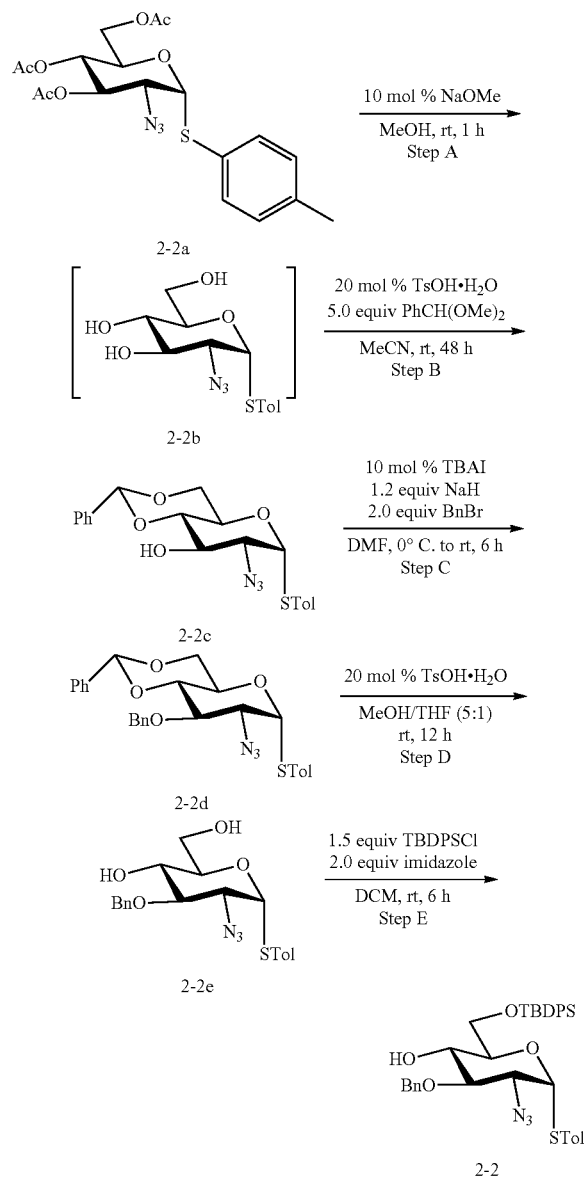

Step A: Synthesis of Compound 2-2a 2-2a (CAS: 1235137-45-7) commercially available, see the synthesis method of compound 2 in reference *Carbohydr Res* 2016, 426, 33 for preparation.

At room temperature, the compound 2-2a (1 equiv.), methanol and sodium methoxide (0.1 equiv., 5 M in MeOH) were added into a single-necked flask, and the mixture was stirred at room temperature. The reaction was monitored by TLC (developing solvent: PE/EtOAc=2/1); after the reaction was completed (about 1 h), dilute hydrochloric acid (1 M) was added to neutralize the solution to pH=7; toluene was added after the reaction solution was concentrated; and residual water in the system was removed by rotary evaporation under reduced pressure by using the azeotropic effect to afford a light brown oily crude product 2-2b, and the crude product was directly used for a next reaction without purification.

Step B: Synthesis of Compound 2-2c

At room temperature, p-toluenesulfonic acid monohydrate (0.2 equiv.) and anhydrous acetonitrile were added in sequence into the crude product 2-2b (1 equiv.) of the previous step, and fully stirred; a nitrogen atmosphere of the system was replaced, and benzaldehyde dimethyl acetal (5 equiv.) was added; the resulting reaction liquid was stirred at room temperature overnight until TLC (developing solvent: PE/EtOAc=5/1) showed that the reaction was complete; then a saturated sodium carbonate solution was added into the reaction system to quench the reaction; extraction and liquid separation were performed with dichloromethane; merged organic phases were washed with water and a saturated salt water, dried over anhydrous sodium sulfate, filtered, concentrated, wet loaded, and purified by column chromatography on silica gel (eluent: PE/EtOAc=5/1) to afford compound 2-2c (white solid, total yield of 85% in two steps). $^1$H NMR (400 MHz, chloroform-d) δ 7.63-7.54 (m, 2H), 7.52-7.39 (m, 5H), 7.25-7.14 (m, 2H), 5.60 (s, 1H), 5.53 (d, J=5.4 Hz, 1H), 4.52-4.39 (m, 1H), 4.28 (dd, J=10.4, 4.9 Hz, 1H), 4.07 (t, J=9.5 Hz, 1H), 3.92 (dd, J=10.0, 5.6 Hz, 1H), 3.79 (t, J=10.3 Hz, 1H), 3.60 (t, J=9.3 Hz, 1H), 3.08 (br s, 1H), 2.40 (s, 3H). MS (ESI) m/z of $C_{20}H_{22}N_3O_4S^+$ $[M+H]^+$: calc 400.1, found 399.9. $^1$H NMR data was consistent with that reported in the literature, see compound 47 in reference Angew. Chem. Int. Ed. 2021, 60, 12413.

Step C: Synthesis of Compound 2-2d

To a dry two-neck flask were added the compound 2-2c (1 equiv.) and anhydrous tetrahydrofuran (reaction concentration 0.2 M) in sequence under a nitrogen atmosphere. The two-neck flask was placed in an ice bath and cooled to 0° C. Sodium hydride (1.2 equiv., 60% content, dispersed in mineral oil) was added. Then the ice bath was removed and the system rose to room temperature and stirred for 1 h, then tetrabutylammonium iodide (0.1 equiv.) and benzyl bromide (1.5 equiv.) were added, and the resulting reaction system was stirred at room temperature until TLC (developing solvent: PE/EtOAc=8/1) showed the reaction was complete (about 6 h). After the reaction ended, water was added dropwise for quenching. Extraction and liquid separation were performed with ethyl acetate, and merged organic phases were washed with water and a saturated salt solution, dried over anhydrous sodium sulfate, filtered, concentrated, and purified by column chromatography on silica gel (eluent: PE/EtOAc=5/1) to afford compound 2-2d (white solid, yield 97%). $^1$H NMR (400 MHz, chloroform-d) δ 7.63-7.55 (m, 2H), 7.53-7.33 (m, 10H), 7.20 (d, J=8.4 Hz, 2H), 5.67 (s, 1H), 5.56 (d, J=4.6 Hz, 1H), 5.05 (d, J=10.9 Hz, 1H), 4.90 (d, J=10.9 Hz, 1H), 4.59-4.47 (m, 1H), 4.31 (dd, J=10.4, 4.9 Hz, 1H), 4.10-3.97 (m, 2H), 3.90-3.77 (m, 2H), 2.41 (s, 3H). MS (ESI) m/z of $C_{27}H_{28}N_3O_4^+$ $[M+H]^+$: calc 490.2, found 490.5. $^1$H NMR data was consistent with that reported in the literature, see compound 20 in reference Bioorg. Med. Chem. 2011, 19, 30.

Step D: Synthesis of Compound 2-2e

Compound 2-2d (1 equiv.), tetrahydrofuran/methanol (v/v=1:1, reaction concentration 0.5 M) and p-toluenesulfonic acid monohydrate (0.2 equiv.) were added in sequence into a single-neck flask, and the mixture was stirred overnight at room temperature. The extent of reaction was monitored by TLC (developing solvent: PE/EtOAc=8/1). After the reaction was complete (about 12 h), a saturated sodium bicarbonate solution was added into the system to quench the reaction. Extraction and liquid separation were performed with ethyl acetate, and merged organic phases were washed with water and a saturated salt solution, dried over anhydrous sodium sulfate, filtered, concentrated, wet loaded, and purified by column chromatography on silica gel (eluent: EtOAc/PE=1/1) to afford compound 2-2e. $^1$H NMR (400 MHz, chloroforms-d) δ 7.41-7.34 (m, 7H), 7.14 (d, J=8.0 Hz, 2H), 5.49 (d, J=5.2 Hz, 1H), 5.01 (d, J=11.2 Hz, 1H), 4.77 (d, J=11.2 Hz, 1H), 4.24-4.20 (m, 1H), 3.89-3.85 (m, 1H), 3.79-3.77 (m, 2H), 3.69-3.65 (m, 2H), 2.42 (br s, 1H), 2.34 (s, 3H). MS (ESI) m/z of $C_{20}H_{27}N_4O_4S^+$ [M+NH$_4$]$^+$: calc 419.2, found 419.2.

Step E: Synthesis of Compound 2-2

Compound 2-2e (1 equiv.), dichloromethane (reaction concentration 0.5 M), imidazole (2 equiv.) and tert-butylchlorodiphenylsilane (1.5 equiv.) were added in sequence into a single-neck flask, and the mixture was stirred at room temperature. The extent of reaction was monitored by TLC (developing solvent: EtOAc/PE=1/12). After the reaction ended (about 6 h), a saturated ammonium chloride solution was added into the system to quench the reaction. Then extraction and liquid separation were performed with dichloromethane, and merged organic phases were washed with water and a saturated salt solution, dried over anhydrous sodium sulfate, filtered, concentrated, wet loaded, and purified by column chromatography on silica gel (eluent: PE/EtOAc/DCM=15/1/1) to afford compound 2-2 (yellow viscous oily liquid, yield 66%). $^1$H NMR (400 MHz, chloroform-d) δ 7.73-7.68 (m, 4H), 7.48-7.35 (m, 13H), 7.06 (d, J=7.6 Hz, 1H), 5.49 (d, J=5.2 Hz, 1H), 4.94 (ABq, J=10.8 Hz, 2H), 4.32-4.27 (m, 1H), 3.96-3.90 (m, 2H), 3.87 (d, J=4.8, 5.2 Hz, 1H), 3.82 (dt, J=2.8, 8.8 Hz, 1H), 3.74-3.69 (m, 1H), 2.70 (d, J=2.8 Hz, OH), 2.33 (s, 3H), 1.09 (s, 9H). MS (ESI) m/z of $C_{36}H_{42}N_3O_4SSi^+$ [M+H]$^+$: calc 640.3, found 640.2.

(3) Synthesis of Compound 2

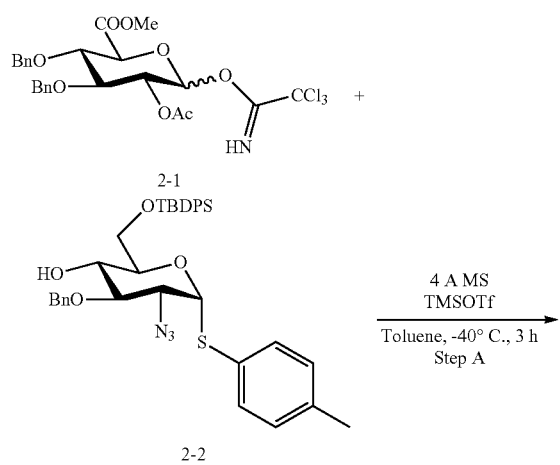

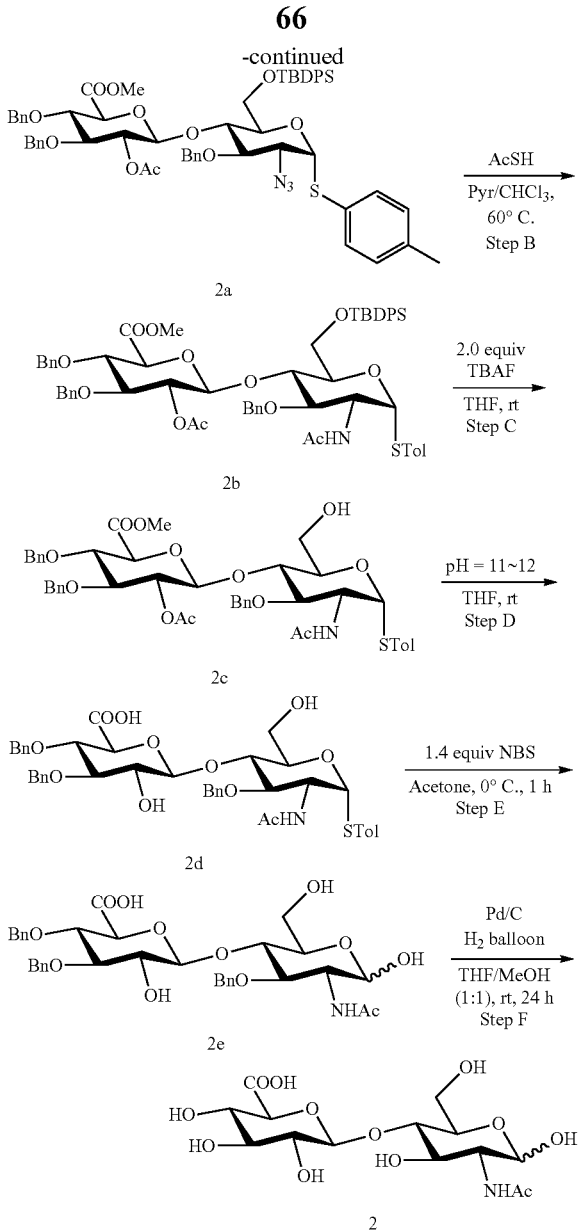

Step A: Synthesis of Compound 2a

A pre-activated molecular sieve was added into a dry two-neck flask, baked with a heat gun under the condition of vacuumizing with an oil pump, and was naturally cooled, then nitrogen replacement was performed. The above-mentioned vacuumizing-nitrogen replacement operations were repeated three times. Subsequently, compound 2-1 (2 equiv.), compound 2-2 (1 equiv.) and dry toluene were added into the system under nitrogen protection, and the resulting system was stirred at room temperature for 0.5 h to fully remove the residual water in the system. Subsequently, the reaction system was cooled to −40° C. and stirred. A certain amount of TMSOTf was added, the resulting reaction mixture was then stirred at this temperature until the reaction was complete as detected by TLC (about 3 h). Ttriethylamine was added into the system to quench the reaction, and filtration, concentration, wet loading, and isolation by column chromatography on silica gel were performed to afford compound 2a (white solid, yield 60%). $^1$H NMR (400 MHz, chloroform-d) δ 7.72 (d, J=6.4 Hz, 2H), 7.64 (d, J=6.4 Hz, 2H), 7.49-7.47 (m, 2H), 7.44-7.23 (m, 21H), 7.04 (d, J=7.8 Hz, 2H), 5.57 (d, J=7.2 Hz, 1H), 5.17 (d, J=7.2 Hz, 1H), 5.10 (dd, J=9.7, 8.1 Hz, 1H), 4.93 (d, J=8.0 Hz, 1H), 4.82 (d, J=11.4 Hz, 1H), 4.74 (d, J=10.9 Hz, 1H), 4.66-4.60 (m, 3H), 4.20 (dd, J=9.2, 9.2 Hz, 1H), 4.05-4.02 (m, 2H), 3.97 (dd, J=9.3, 9.2 Hz, 1H), 3.92-3.76 (m, 3H), 3.74-3.67 (m, 1H), 3.60 (s, 3H), 3.51 (dd, J=9.2, 9.2 Hz, 1H), 2.32 (s, 3H), 1.82 (s, 3H), 1.07 (s, 9H). MS (ESI) m/z of $C_{59}H_{66}N_3O_{11}SSi^+$ $[M+H]^+$: calc 1052.4, found 1052.7.

Step B: Synthesis of Compound 2b

To a reaction flask were added the compound 2a (1 equiv.), and mercaptoacetic acid (CAS: 68-11-1)/pyridine/trichloromethane (v/v/v=1:1:1). The system rose to 60° C. and was stirred. The extend of reaction was monitored by TLC. After the reaction was complete (about 12 h), concentration under reduced pressure was performed to remove most of the solvent. An appropriate amount of ethyl acetate was added and washed with a saturated sodium bicarbonate solution. After extraction and liquid separation, organic phases were washed with 1 M hydrochloric acid solution. After liquid separation, washing was performed with the saturated sodium bicarbonate solution after liquid separation, and the resulting organic phase was dried over anhydrous sodium sulfate and then filtered, concentrated and purified by column chromatography to afford compound 2b (white solid, yield 71%). $^1$H NMR (400 MHz, chloroform-d) δ 7.70 (d, J=6.8 Hz, 2H), 7.66 (d, J=7.2 Hz, 2H), 7.44-7.28 (m, 20H), 7.26-7.21 (m, 3H), 7.00 (d, J=7.9 Hz, 2H), 5.68 (d, J=4.8 Hz, 1H), 5.36-5.30 (m, 1H), 5.09 (dd, J=9.5, 8.1 Hz, 1H), 4.92 (d, J=12.4 Hz, 1H), 4.85 (d, J=11.5 Hz, 1H), 4.75-4.66 (m, 3H), 4.63-4.57 (m, 2H), 4.29 (ddd, J=9.3, 7.7, 4.8 Hz, 1H), 4.10 (t, J=7.8 Hz, 1H), 4.01 (dd, J=11.5, 3.2 Hz, 1H), 3.94-3.89 (m, 2H), 3.86-3.84 (m, 1H), 3.80 (dd, J=11.5, 2.5 Hz, 1H), 3.67 (s, 3H), 3.60-3.51 (m, 2H), 2.28 (s, 3H), 1.85 (s, 3H), 1.82 (s, 3H), 1.07 (s, 9H). MS (ESI) m/z of $C_{61}H_{70}NO_{12}SSi^+$ $[M+H]^+$: calc 1068.4, found 1068.4.

Step C: Synthesis of Compound 2c

To a reaction flask were added the compound 2b (1 equiv.) and tetrahydrofuran. Subsequently, TBAF (2 equiv., 1 M in THF) was added into the system, and stirred at room temperature. The extent of reaction was monitored by TLC. After the reaction was complete (about 10 h), a saturated ammonium chloride solution was added into the system to quench the reaction. Then extraction and liquid separation were performed with ethyl acetate, and merged organic phases were washed with water and a saturated salt solution, dried over anhydrous sodium sulfate, filtered, concentrated, and wet loaded, and preliminarily purified by column chromatography on silica gel to afford compound 2c (white solid, crude yield 56%). MS (ESI) m/z. of $C_{45}H_{52}NO_{12}S^+$ $[M+H]^+$: calc 830.3, found 830.6.

Step D: Synthesis of Compound 2d

The compound 2c was dissolved in THF/MeOH (v/v=3:1). 1 M sodium hydroxide aqueous solution was slowly added to adjust the system to pH=12. The resulting reaction solution was stirred at room temperature. The extent of reaction was monitored by HPLC. After the reaction was sufficient (about 12 h), 1 M hydrochloric acid was added into the system to adjust the system to pH=7 to 8. Concentration under reduced pressure was performed to remove most of the organic solvent, and the resulting crude product was purified by HPLC to afford compound 2d (white solid, yield 82%). $^1$H NMR (400 MHz, chloroform-d) δ 7.43-7.27 (m, 17H), 7.07 (d, J=7.9 Hz, 2H), 5.54 (d, J=5.0 Hz, 1H), 5.33 (d, J=8.0 Hz, 1H), 4.93 (d, J=12.1 Hz, 1H), 4.86 (d, J=11.3 Hz, 1H), 4.82-4.77 (m, 3H), 4.74 (d, J=6.8 Hz, 1H), 4.69 (d, J=12.2 Hz, 1H), 4.36 (ddd, J=10.6, 7.9, 5.0 Hz, 1H), 4.25-4.22 (m, 1H), 4.13-4.02 (m, 3H), 3.88 (t, J=8.6 Hz, 1H), 3.81 (dd, J=12.7, 2.2 Hz, 1H), 3.74 (dd, J=10.7, 8.5 Hz, 1H), 3.68-3.59 (m, 2H), 3.40 (br s, 1H), 2.30 (s, 3H), 1.77 (s, 3H). $^{13}$C NMR (100 MHz, chloroform-d) δ 170.73, 169.33, 138.20, 138.06, 137.81, 137.55, 132.37, 129.99, 129.44, 128.84, 128.76, 128.58, 128.42, 128.30, 127.90, 103.24, 88.40, 83.43, 78.89, 77.85, 77.35, 77.24, 77.03, 76.92, 76.72, 75.17, 74.93, 74.57, 74.02, 73.93, 72.95, 60.66, 52.95, 23.08, 21.06 (There were three carbon signals overlapped in the aromatic region without peak appearance). MS (ESI) m/z of $C_{42}H_{46}NO_{11}S^-$ $[M-H]^-$: calc 772.3, found 772.2.

Step E: Synthesis of Compound 2e

The compound 2d was weighed and dissolved in acetone, and stirred for 5 min in an ice water bath for cooling. NBS was weighed and added into the reaction solution and reacted in the ice water bath for about 1 h. A sample was taken and sent for detection by HPLC to confirm that the reaction ended. After quenching with a saturated sodium thiosulfate solution, concentration was performed to remove acetone, preparation by prep HPLC was performed, and freeze drying was performed to afford 2e (white solid, yield 45%). MS (ESI) m/z of $C_{35}H_{40}NO_{12}^-$ $[M-H]^-$: calc 666.3, found 666.4.

Step F: Synthesis of Compound 2

To a 50 mL single-neck flask were added the compound 2e, tetrahydrofuran, methanol, and palladium-carbon catalyst in sequence at room temperature, and the reaction system was stirred under a hydrogen atmosphere until all raw materials disappeared as detected by TLC. Filtration, concentration under reduced pressure, draining with oil pump were performed to afford compound 2 (white solid, yield 95%). MS (ESI) m/z of $C_{14}H_{22}NO_{12}^-$ $[M-H^+]^-$: calc 396.1, found 396.1.

Preparation of Disaccharide Substrate Compound 3

Compound 3 was prepared by employing the following steps, with a structure as follows:

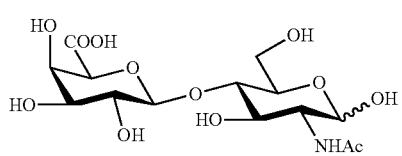

3

For the preparation process of the compound 3, refer to the similar synthesis method of the compound 2, and the specific route is as follows:

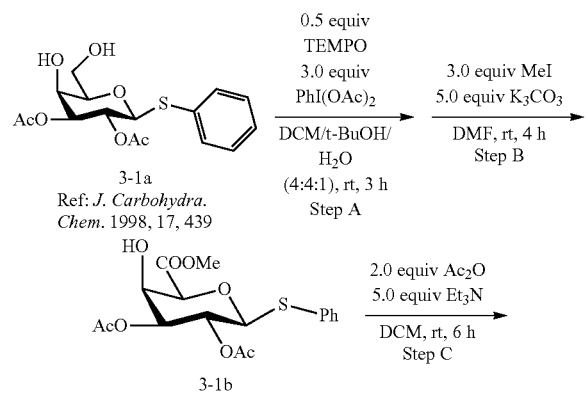

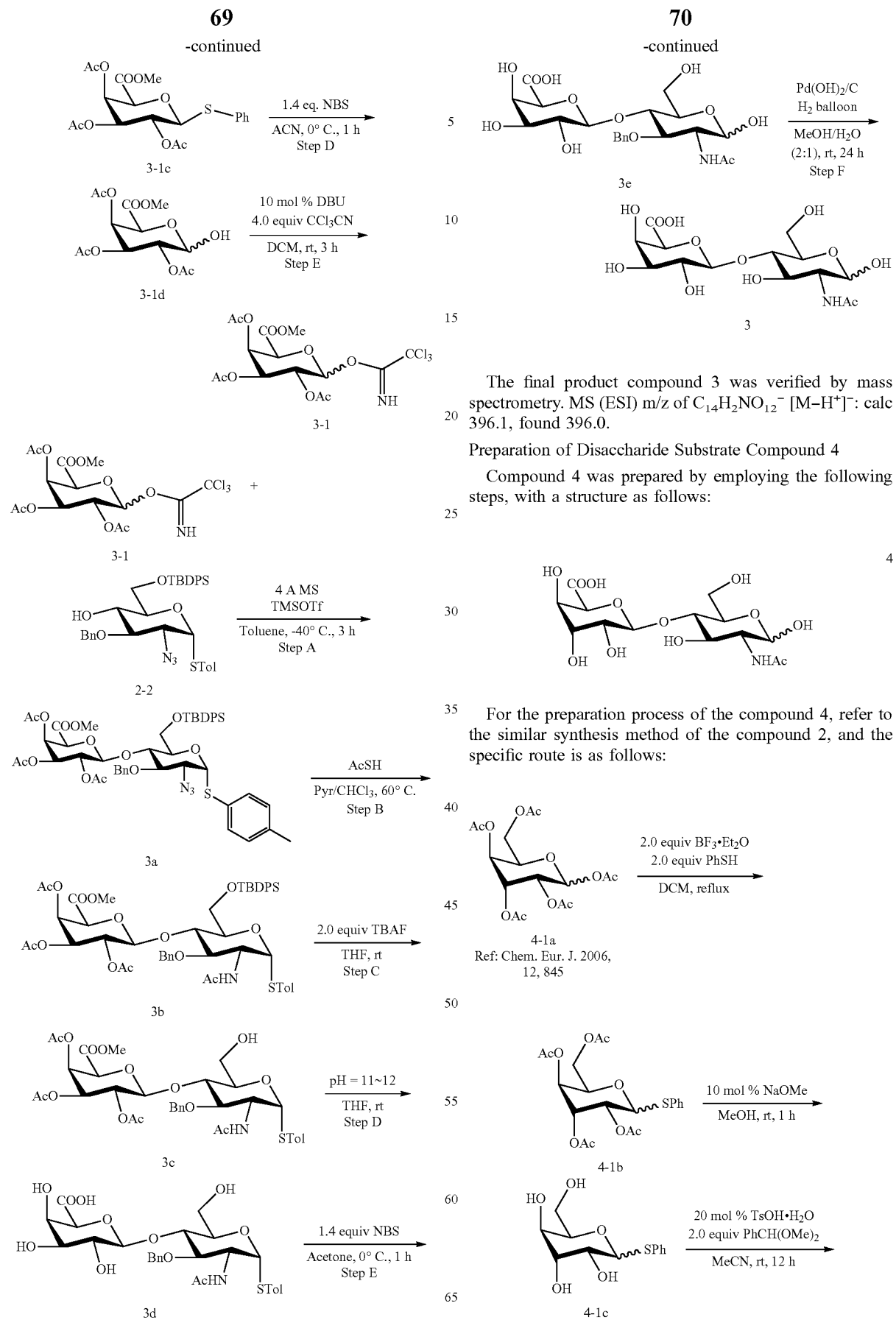

The final product compound 3 was verified by mass spectrometry. MS (ESI) m/z of $C_{14}H_2NO_{12}^-$ [M–H$^+$]$^-$: calc 396.1, found 396.0.

Preparation of Disaccharide Substrate Compound 4

Compound 4 was prepared by employing the following steps, with a structure as follows:

For the preparation process of the compound 4, refer to the similar synthesis method of the compound 2, and the specific route is as follows:

-continued
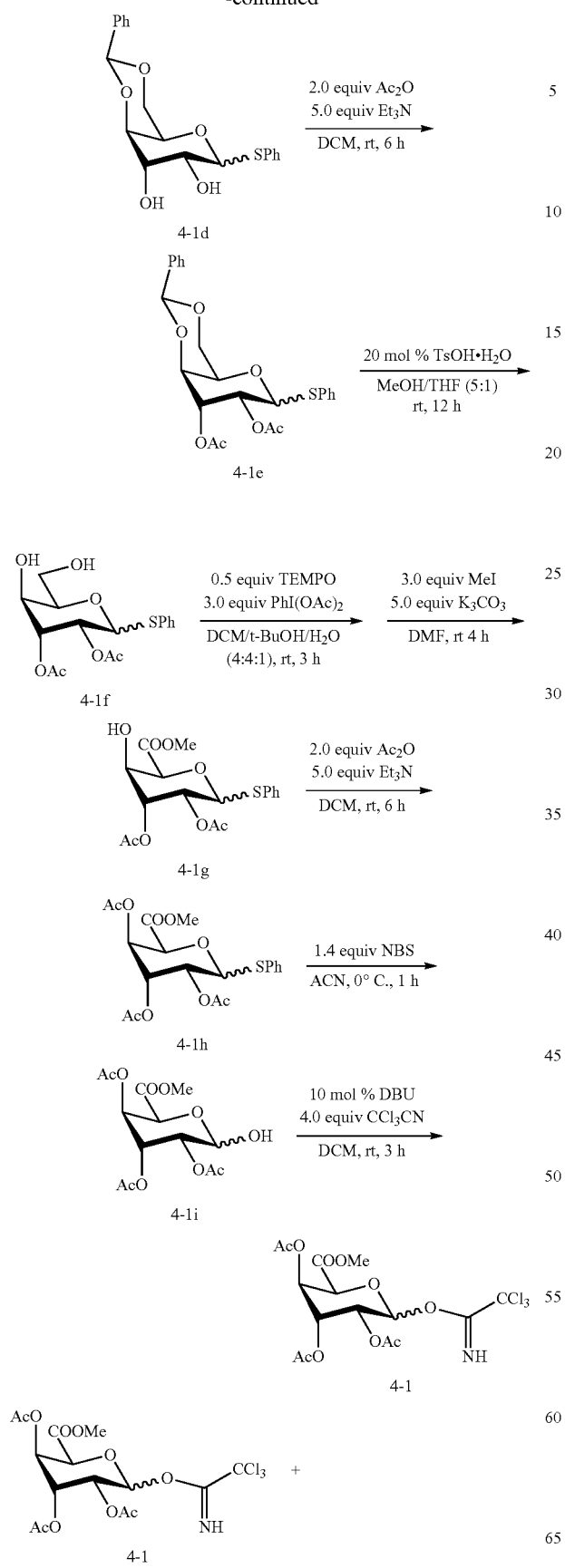
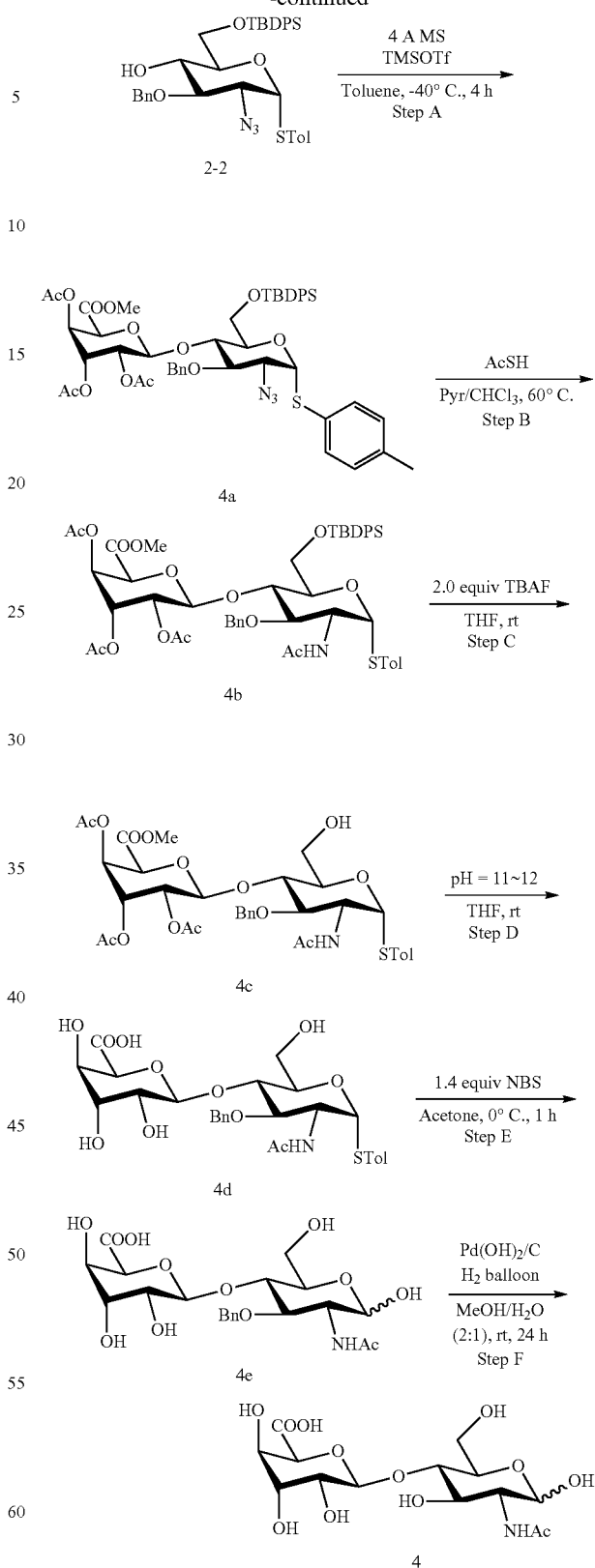
The final product compound 4 was verified by mass spectrometry. MS (ESI) m/z of $C_{14}H_2NO_{12}^-$ [M−H$^+$]$^-$: calc 396.1, found 396.1.

Preparation of Disaccharide Substrate Compound 5

Compound 5 was prepared by employing the following steps, with a structure as follows:

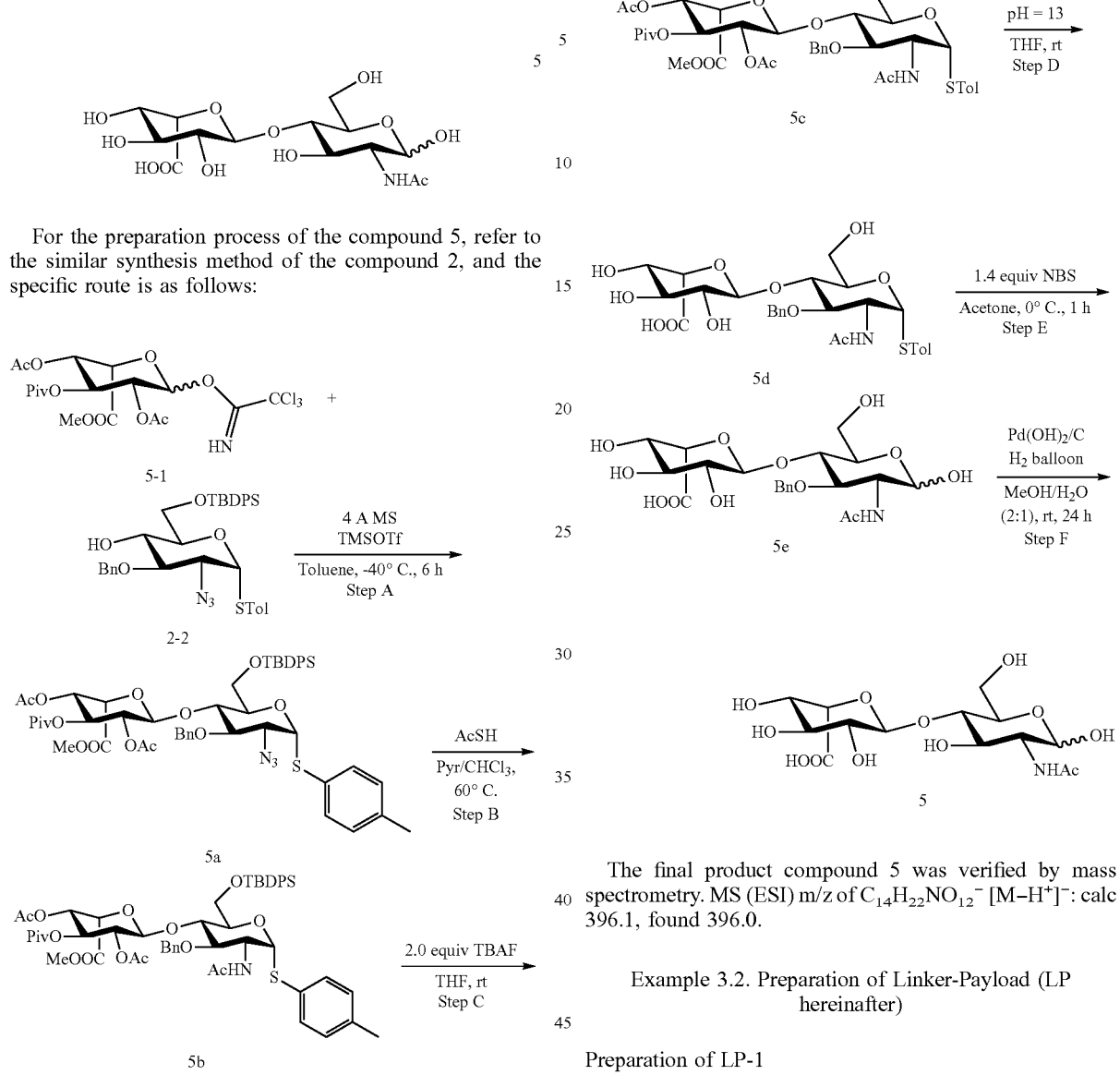

For the preparation process of the compound 5, refer to the similar synthesis method of the compound 2, and the specific route is as follows:

The final product compound 5 was verified by mass spectrometry. MS (ESI) m/z of $C_{14}H_{22}NO_{12}^{-}$ [M–H$^+$]$^-$: calc 396.1, found 396.0.

Example 3.2. Preparation of Linker-Payload (LP hereinafter)

Preparation of LP-1

The linker-payload 1 (LP-1) has a structure as follows:

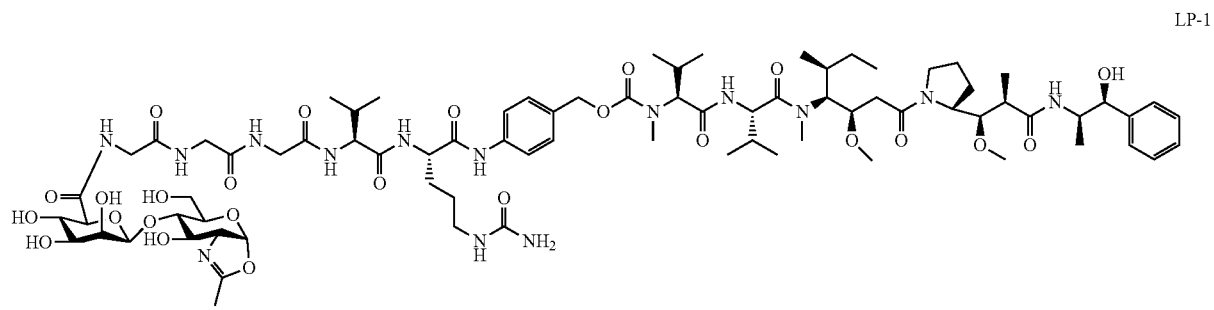

LP-1

(1) Preparation of Compound LP-1b

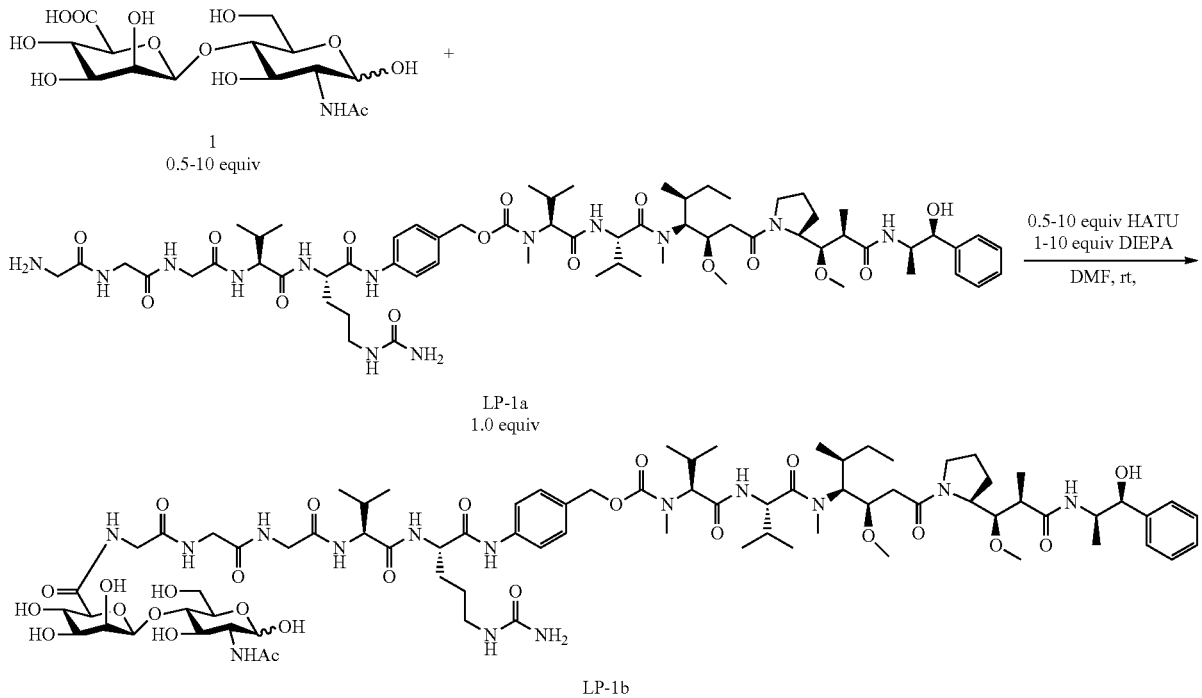

To a 10 mL single-neck flask were added compound 1 (0.5 to 5.0 equiv.), compound LP-1a (1.0 equiv., GGG-VC-PAB-MMAE, CAS number: 2684216-48-4, commercially available), DMF, DIPEA (1 to 10 equiv.), and HATU (0.5 to 10 equiv.) at room temperature in sequence, and the resulting reaction solution was stirred at room temperature until the reaction was complete as monitored by HPLC. The reaction solution was purified by semi-preparative HPLC to afford compound LP-1b (white solid, yield 81.2%). MS (ESI) m/z of $C_{78}H_{126}N_{14}O_{26}^{2+}$ $[M+2H]^{2+}$: calc 837.4, found 837.9.

(2) Preparation of Compound LP-1

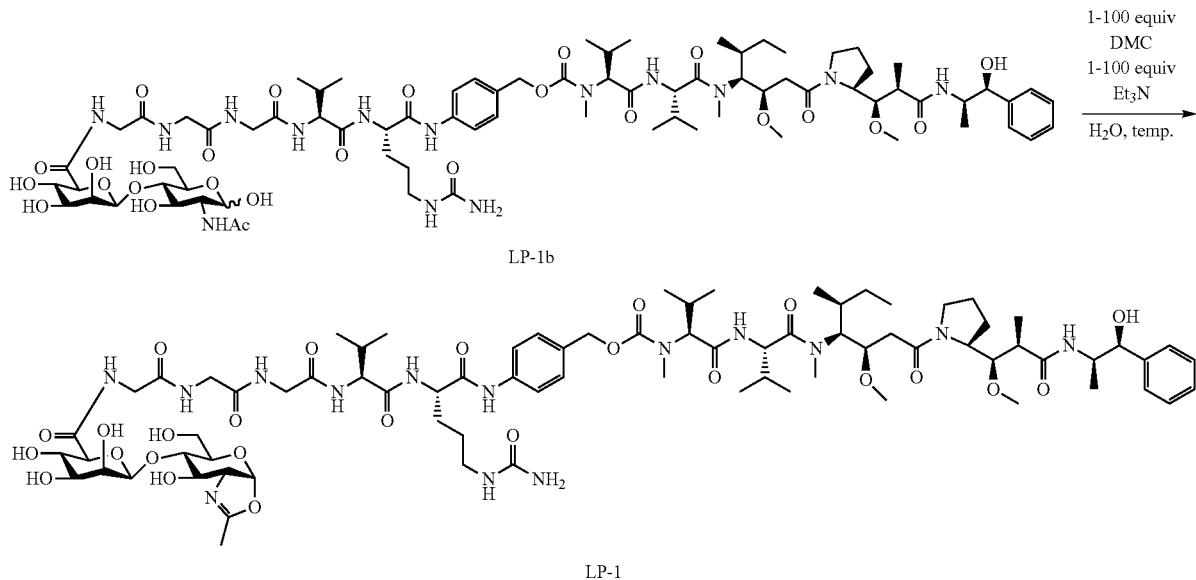

To a 10 mL single-neck flask were added the compound LP-1b (21.7 mg, 0.013 mmol, 1 equiv.), H₂O, Et₃N (1 to 100 equiv.) and DMC (2-chloro-1,3-dimethylimidazolidinium chloride, CAS: 37091-73-9, 1 to 100 equiv.) in sequence at room temperature. The resulting reaction solution was stirred at room temperature, and the reaction was monitored by HPLC until the reaction was complete. The reaction solution was purified by semi-preparative HPLC to afford compound LP-1 (15.3 mg, yield 71.3%, white solid). MS (ESI) m/z of $C_{78}H_{124}N_{14}O_{25}{}^{2+}$ [M+2H]$^{2+}$: calc 828.4, found 828.6.

Preparation of LP-2

The linker-payload 2 (LP-2) has a structure as follows:

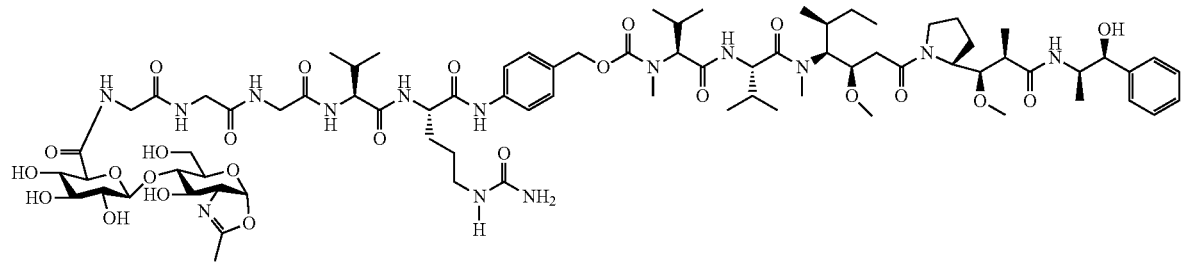

LP-2

The preparation process is as follows:

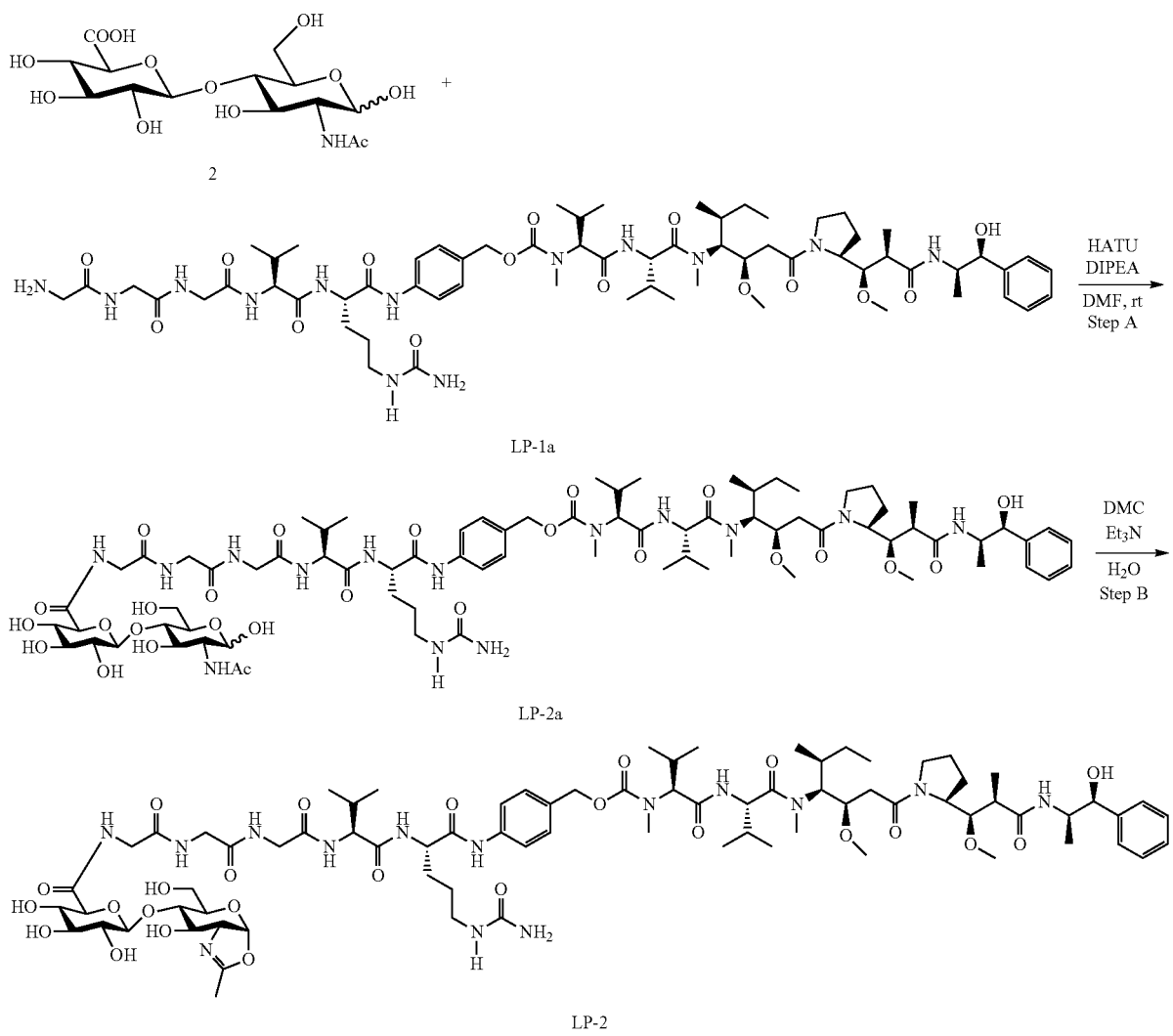

20.1 Step A: Preparation of Compound LP-2a

To a 10 mL single-neck flask were added the compound 2 (0.5 to 5.0 equiv.), compound LP-1a (1.0 equiv., GGG-VC-PAB-MMAE, CAS number: 2684216-48-4, commercially available), DMF, DIPEA (1 to 10 equiv.), and HATU (0.5 to 10 equiv.) in sequence at room temperature, and the resulting reaction solution was stirred at room temperature until the reaction was complete as monitored by HPLC. The reaction solution was purified by semi-preparative HPLC to afford compound LP-2a (white solid, yield 84%). MS (ESI) m/z of $C_{78}H_{126}N_{14}O_{26}^{2+}$ [M+2H]$^{2+}$: calc 837.4, found 837.8.

20.2 Step B: Preparation of Compound LP-2

To a 10 mL single-neck flask were added the compound LP-2a (1 equiv.), H$_2$O, Et$_3$N (1 to 100 equiv.) and DMC (2-chloro-1,3-dimethylimidazolidinium chloride, CAS: 37091-73-9, 1 to 100 equiv.) in sequence at room temperature. The resulting reaction solution was stirred at 0° C., and the reaction was monitored by HPLC until the reaction was complete. The reaction solution was purified by semi-preparative HPLC to afford compound LP-2 (yield 87%, white solid). MS (ESI) m/z of $C_{78}H_{124}N_{14}O_{25}^{2+}$ [M+2H]$^{2+}$: calc 828.4, found 828.7.

Preparation of LP-3, LP-4 and LP-5

Linker-payloads LP-3, LP-4 and LP-5 with the following structures were prepared by employing steps similar to those of LP-2 preparation.

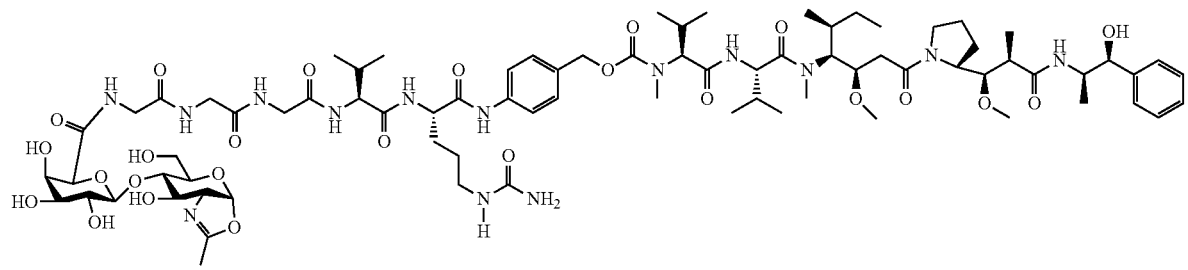

LP-3

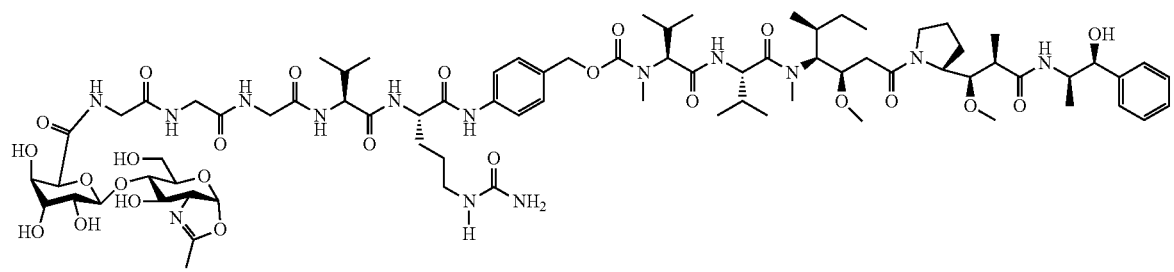

LP-4

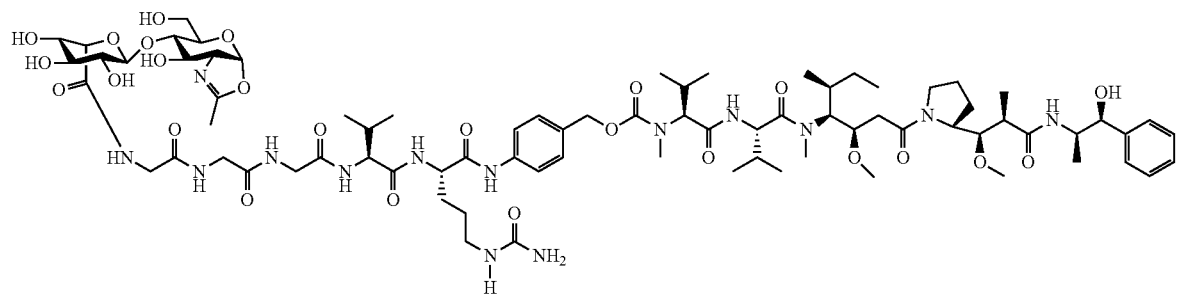

LP-5

Preparation of LP-6
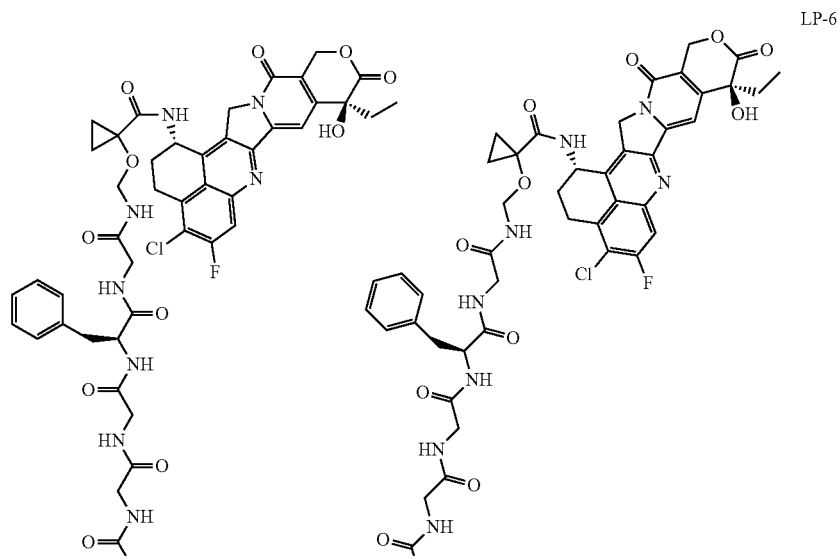
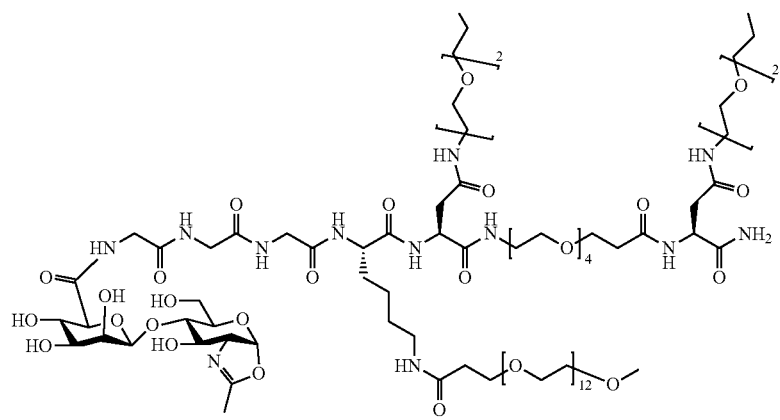
(1) Synthesis of LP-6-1
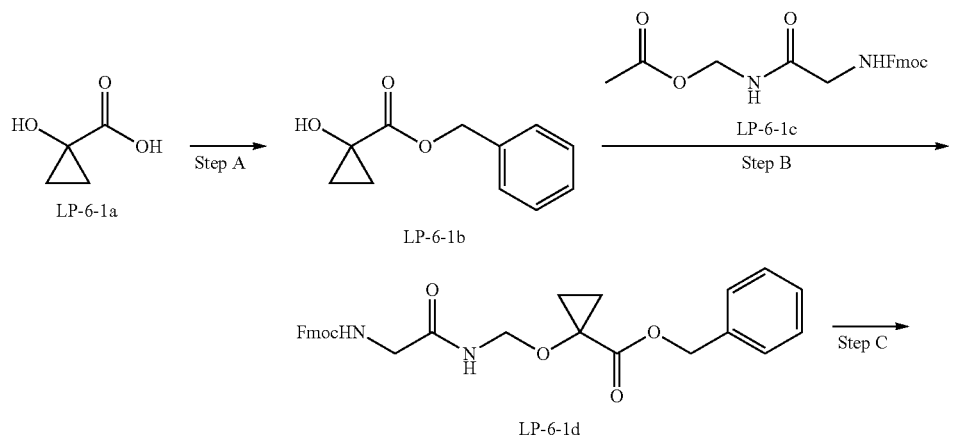

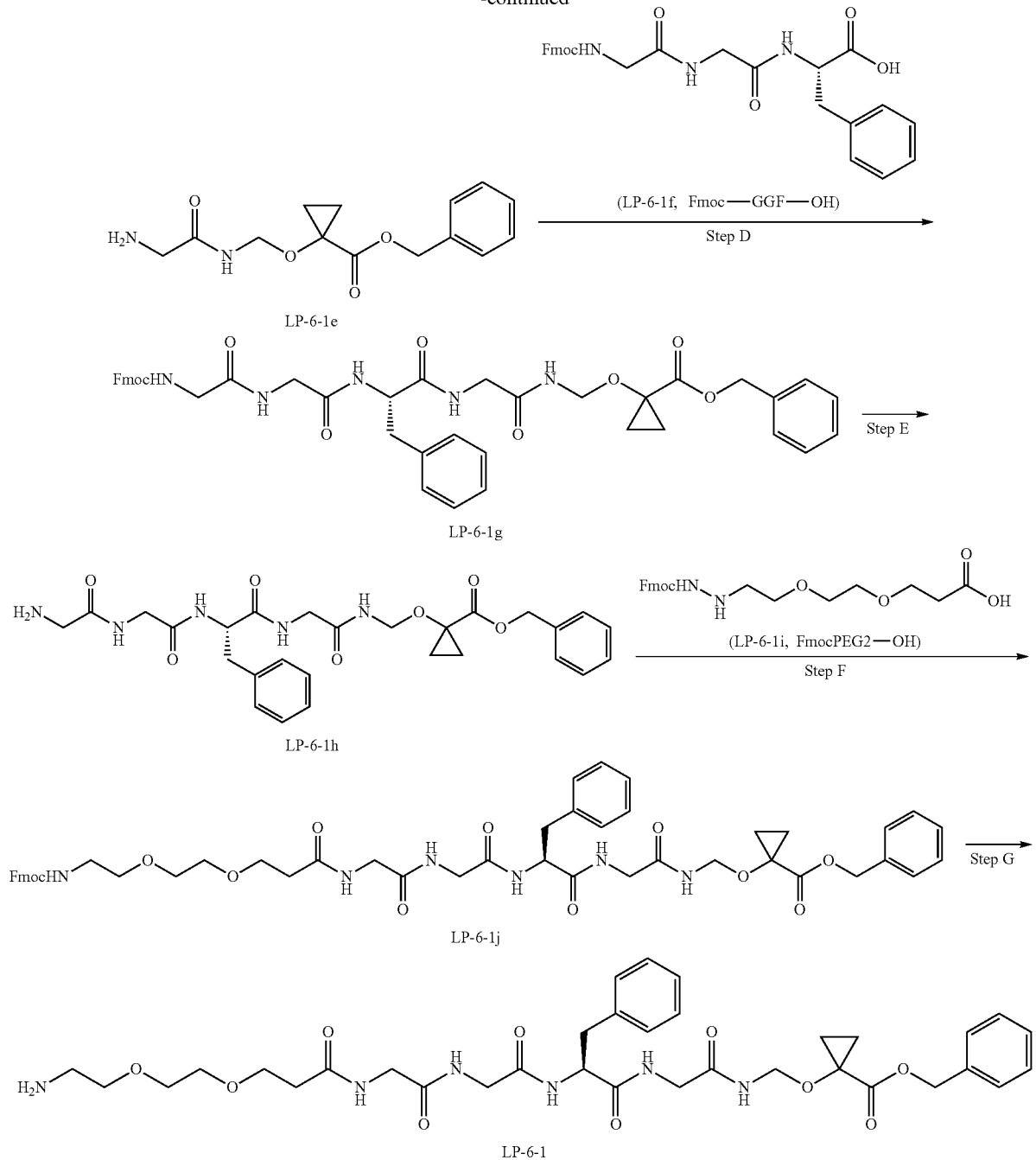

Step A: Synthesis of Intermediate LP-6-1b

Compound LP-6-1a (1.0 equiv.) and DMF (dissolution concentration: 1 g/mL) were added into a reaction flask, stirred for dissolution under a nitrogen atmosphere, and cooled to 0° C. to 5° C., and then, DIEA (3 equiv.) was dropwise added. Subsequently, the resulting system was stirred at 5° C. for 10 min, and then benzyl bromide (1.3 equiv.) was dropwise added. After dropwise adding, the reaction system was allowed to naturally rise to room temperature and stirred for 16 h. The reaction solution was slowly poured into ice water, and methyl tert-butyl ether was added and stirred, followed by standing and liquid separation. An aqueous phase was extracted four times with methyl tert-butyl ether. Organic phases were merged, and washed with a saturated salt solution, dried over anhydrous sodium sulfate, filtered, and concentrated to afford a yellow oily crude product, and the yellow oily crude product was wet loaded, and purified by column chromatography on silica gel (eluent: PE/EA=6:1) to afford the product LP-6-1b (light yellow oil, quantitative yield).

Step B: Synthesis of Intermediate LP-6-1d

Under nitrogen protection, intermediate LP-6-1b (2.0 equiv.), compound LP-6-1c (1.0 equiv.) and THF (dissolution concentration: 10 g/mL) were added into a reaction flask, and stirred for dissolution, TsOH (0.1 equiv.) was added to the reaction, and the system reacted at room temperature for 4 h. The reaction solution was slowly poured into ice water, and extracted with ethyl acetate three times. Merged organic phases were washed with a saturated sodium bicarbonate aqueous solution, water and a saturated salt solution, dried over anhydrous sodium sulfate, filtered and concentrated to afford a crude product, and the crude product was purified by column chromatography on silica gel (eluent: PE/EA=1:1) to afford product LP-6-1d (white solid, yield 40%).

Step C: Synthesis of Intermediate LP-6-1e

Under nitrogen protection, the compound LP-6-1d and N,N-dimethylacetamide (DMAc, dissolution concentration: 10 g/mL) were added into a reaction flask, and stirred for dissolution. The system was cooled to 14° C. to 18° C., DBU (0.5 equiv.) was dropwise added, and a reaction was carried out at this temperature, until TLC showed that the reaction was complete (about 1.5 h) to afford intermediate LP-6-1e, and the intermediate was directly used for a next reaction without purification.

Step D: synthesis of intermediate LP-6-1g

The reaction solution in the previous step was cooled to 0° C. to 5° C., and pyridinium 4-toluenesulfonate (PPTS, 0.5 equiv.), 1-(3-dimethylaminopropyl)-3-ethylcarbodiimide (EDCI, 1.0 equiv.), 1-hydroxybenzotriazole (HOBT, 1.0 equiv.) and LP-6-1f (0.85 equiv.) were added in sequence. The reaction system reacted at 0° C. to 10° C. until LCMS showed that the reaction was complete (about 4 h). The reaction solution was added into ice water, and 2-methyltetrahydrofuran was added for extraction once. An aqueous phase was extracted twice with the 2-methyltetrahydrofuran. Organic phases were merged, and washed in sequence with 0.5 M hydrochloric acid, a saturated NaHCO$_3$ aqueous solution, water and a saturated salt solution, dried over anhydrous sodium sulfate, filtered, concentrated, and purified by column chromatography on silica gel (eluent: DCM/MeOH) to afford product LP-6-1g (white solid, yield 78%).

Step E: Synthesis of Intermediate LP-6-1h

Under nitrogen protection, LP-6-1g and DMAc (dissolution concentration: 10 g/mL) were added into a reaction flask and stirred for dissolution. The temperature was lowered to 14° C. to 18° C.; DBU (0.5 equiv.) was dropwise added, and a reaction was carried out with stirring at this temperature for 1.5 h. The extent of reaction was monitored by TLC. After the reaction was completed, intermediate LP-6-1h was afforded, and was directly used for a next reaction without purification.

Step F: Synthesis of Intermediate LP-6-1j

The reaction solution of LP-6-1h in the previous step was cooled to 0° C. to 5° C., and PPTS (0.5 equiv.), EDCI (1 equiv.), HOBT (1 equiv.) and compound3i (0.85 equiv.) were added, and reacted at 0° C. to 10° C. for 3 to 4 h. The extent of reaction was monitored by LCMS. After the reaction was complete, the reaction solution was added into ice water, and 2-methyltetrahydrofuran was added for extraction once. An aqueous phase was extracted twice with the 2-methyltetrahydrofuran. Organic phases were merged, and washed in sequence with 0.5 M hydrochloric acid, a saturated NaHCO$_3$ aqueous solution, water and a saturated salt solution, dried over anhydrous sodium sulfate, filtered, concentrated, dry blended, and purified by column chromatography (eluent: DCM/MeOH) to afford LP-6-1j (white solid, yield 50%).

Step G: Synthesis of Compound LP-6-1

Under nitrogen protection, the intermediate LP-6-1j was dissolved in DCM (concentration: 15 g/mL), and DBU (0.5 equiv.) was dropwise added at 20° C. A reaction was carried out with stirring at this temperature until HPLC showed that the reaction was complete. Subsequently, DCM was added into the system to dilute the reaction solution, directly wet loaded and purified by column chromatography (eluent: DCM/MeOH) to afford compound LP-6-1 (white solid, yield 82%). MS (ESI) m/z of $C_{34}H_{47}N_6O_{10}^+$ [M+H]$^+$: calc 699.4, found 699.6.

(2) Synthesis of LP-6-2

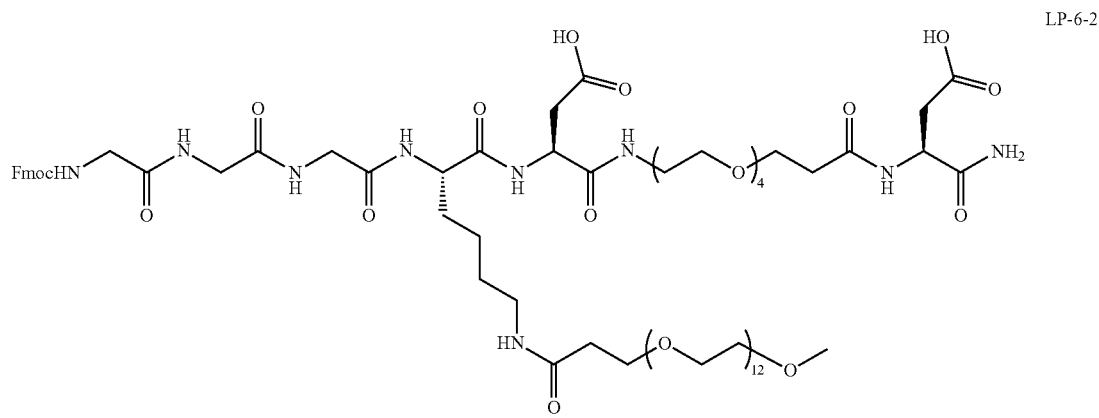

LP-6-2

LP-6-2 was synthesized by employing a peptide solid-phase synthesis, and the steps were shown as follows.

Step 1: Preparation of NH2-Asp(OtBu)-Rink Amide Resin 400 g of Rink amide resin was weighed and placed into a reactor, and soaked in 2400 mL of DCM for 0.5h to allow the resin to fully swell, followed by draining. 2400 mL of decapping reagent was added, and washing was performed, followed by draining. 2400 mL of decapping reagent was added, nitrogen was blown, and a reaction was carried out with stirring at 25° C.±1° C. for 0.5 h, followed by draining. Washing was performed twice in sequence with 2400 mL of DMF, 2400 mL of absolute ethanol, 2400 mL of DCM, and 2400 mL of DMF, followed by draining. Kaiser test showed blue.

88.87 g of Fmoc-Asp(OtBu)-OH and 29.19 g of HOBT were weighed and dissolved in 2000 mL of DMF solution and 80 ml of DIC, the mixture was placed in an ice bath at −10° C. for 0.5 h, and then slowly added into a reactor for reaction, at room temperature, nitrogen was blown, and a reaction was carried out with stirring for 2 h, followed by draining. Washing was performed twice in sequence with 2400 mL of DMF, 2400 mL of absolute ethanol, 2400 mL of DCM, and 2400 mL of DMF, followed by draining. Kaiser test showed light blue. 2400 mL of DCM was added, and then 60 ml of capping reagent was added, nitrogen was blown, and a reaction was carried out with stirring at 25° C.±1° C. for 1 h, followed by draining. Washing was performed twice in sequence with 2400 mL of DMF, 2400 mL of absolute ethanol, 2400 mL of DCM, and 2400 mL of DMF, followed by draining. Kaiser test showed colorlessness.

2400 mL of decapping reagent was added, and washing was performed, followed by draining. 2400 mL of decapping reagent was added, nitrogen was blown, and a reaction was carried out with stirring at 25° C.±1° C. for 0.5 h, followed by draining. Washing was performed twice in sequence with 2400 mL of DMF, 2400 mL of absolute ethanol, 2400 mL of DCM, and 2400 mL of DMF, followed by draining. Kaiser test showed blue.

Step 2: Preparation of NH2-PEG4-Asp(OtBu)-Rink Amide Resin 131.64 g of Fmoc-PEG4-OH and 48.64 g of HOBT were weighed and dissolved in 2000 mL of DMF solution and 80.0 ml of DIC, and the mixture was placed in an ice bath at −10° C. for 0.5 h, and then slowly added into a reactor for reaction. At room temperature, nitrogen was blown, and a reaction was carried out with stirring for 2 to 4 h, followed by draining. Washing was performed twice in sequence with 2400 mL of DMF, 2400 mL of absolute ethanol, 2400 mL of DCM, and 2400 mL of DMF, followed by draining. Kaiser test showed colorlessness.

2400 mL of decapping reagent was added, and washing was performed, followed by draining. 2400 mL of decapping reagent was then added, nitrogen was blown, and a reaction was carried out with stirring at 25±1° C. for 0.5 h, followed by draining. Washing was performed twice in sequence with 2400 mL of DMF, 2400 mL of absolute ethanol, 2400 mL of DCM, and 2400 mL of DMF, followed by draining. Kaiser test showed blue.

Step 3: Preparation of NH2-Asp(OtBu)-PEG4-Asp(OtBu)-Rink Amide Resin 222.18 g of Fmoc-Asp(OtBu)-OH and 72.96 g of HOBT were weighed and dissolved in 2000 mL of DMF solution and 80 ml of DIC, and the mixture was placed in an ice bath at −10° C. for 0.5 h, and then slowly added into a reactor for reaction. At room temperature, nitrogen was blown, and a reaction was carried out with stirring for 2 to 4 h, followed by draining. Washing was performed twice in sequence with 2400 mL of DMF, 2400 mL of absolute ethanol, 2400 mL of DCM, and 2400 mL of DMF, followed by draining. Kaiser test showed colorlessness.

2400 of decapping reagent was added, and washing was performed, followed by draining. 2400 mL of decapping reagent was then added, nitrogen was blown, and a reaction was carried out with stirring at 25±1° C. for 0.5 h, followed by draining. Washing was performed twice in sequence with 2400 mL of DMF, 2400 mL of absolute ethanol, 2400 mL of DCM, and 2400 mL of DMF, followed by draining. Kaiser test showed blue.

Step 4: Preparation of Dde-Lys(NH2)-Asp(OtBu)-PEG4-Asp(OtBu)-Rink Amide Resin 191.75 g of Dde-Lys(Fmoc)-OH and 48.64 g of HOBT were weighed and dissolved in 2000 mL of DMF solution and 80.0 ml of DIC, and the mixture was placed in an ice bath at −10° C. for 0.5 h, and then slowly added into a reactor for reaction. At room temperature, nitrogen was blown, and a reaction was carried out with stirring for 2 to 4 h, followed by draining. Washing was performed twice in sequence with 2400 mL of DMF, 2400 mL of absolute ethanol, 2400 mL of DCM, and 2400 mL of DMF, followed by draining. Kaiser test showed colorlessness.

2400±100 mL of decapping reagent was added, and washing was performed, followed by draining. 2400 mL of decapping reagent was then added, nitrogen was blown, and a reaction was carried out with stirring at 25±1° C. for 0.5 h, followed by draining. Washing was performed twice in sequence with 2400 mL of DMF, 2400 mL of absolute ethanol, 2400 mL of DCM, and 2400 mL of DMF, followed by draining. Kaiser test showed blue.

Step 5: Preparation of Dde-Lys(mPEG12)-Asp(OtBu)-PEG4-Asp(OtBu)-Rink Amide Resin 170.84 g of m-PEG12-CH2CH2COOH and 48.64 g of HOBT were weighed and dissolved in 2000 mL of DMF solution and 80.0 ml of DIC, and the mixture was placed in an ice bath at −10° C. for 0.5 h, and then slowly added into a reactor for reaction. At room temperature, nitrogen was blown, and a reaction was carried out with stirring for 2 to 4 h, followed by draining. Washing was performed twice in sequence with 2400 mL of DMF, 2400 mL of absolute ethanol, 2400 mL of DCM, and 2400 mL of DMF, followed by draining. Kaiser test showed colorlessness.

Step 6: Preparation of NH2-Lys(PEG12)-Asp(OtBu)-PEG4-Asp(OtBu)-Rink Amide Resin 2400 mL of de-dde reagent was added, nitrogen was blown, and a reaction was carried out with stirring at 25° C.±1° C. for 10 min, followed by draining. After this operation was repeated three times, washing was performed twice in sequence with 2400 mL of DMF, 2400 mL of absolute ethanol, 2400 mL of DCM, and 2400 mL of DMF, followed by draining. Kaiser test showed blue.

Step 7: Preparation of Fmoc-Gly-Gly-Gly-Lys(PEG12)-Asp(OtBu)-PEG4-Asp(OtBu)-Rink Amide Resin 111.08 g of Fmoc-Gly-Gly-Gly-OH and 48.64 g of HOBT were weighed and dissolved in 2000 mL of DMF solution and 80.0 ml of DIC, and the mixture was placed in an ice bath at −10° C. for 0.5 h, and then slowly added into a reactor for reaction. At room temperature, nitrogen was blown, and a reaction was carried out with stirring for 2 to 4 h, followed by draining. Washing was performed twice in sequence with 2400 mL of DMF, 2400 mL of absolute ethanol, 2400 mL of DCM, and 2400 mL of DMF, followed by draining. Kaiser test showed colorlessness. Resin peptide was washed three times with 2400 mL of absolute ethanol, drained, and left to cut.

Step 8: Preparation of LP-6-2

10000 mL of cleavage reagent (TFA:TIS:H2O=95:2.5:2.5) was added into a 10 L reactor and cooled to −10° C.±2° C., and the dried weighed resin was added thereinto, followed by heating, at 20° C.±5° C., nitrogen was introduced and stirring was carried out for 2 h. Filtration was performed, the resin was washed once with 100 mL of TFA, and the filtrate and the washing solution were merged.

40 L of pre-cooled (below −10° C.) cold ether was added, and stirred for 10 min, and then centrifugal precipitation was performed. Then the supernatant was discarded. Precipitates were mixed and shaken up with the cold ether. Then centrifugal precipitation was performed again (this step was repeated three times, with the dosage of 10 L, 10 L, and 10 L each time. The revolution speed was set to be 3600 rpm for each centrifugation, the centrifugation time was 5 minutes, and the temperature of the inner chamber of a centrifuge was −5° C.).

The precipitates were collected to afford an LP-6-2 crude product, and the crude product was purified by Prep-HPLC and freeze-dried to afford LP-6-2. MS (ESI) m/z of $C_{74}H_{121}N_9O_{31}{}^{2+}$ [M+2H]$^{2+}$: calc: 815.9, found 816.3.

(3) Synthesis of LP-6-3

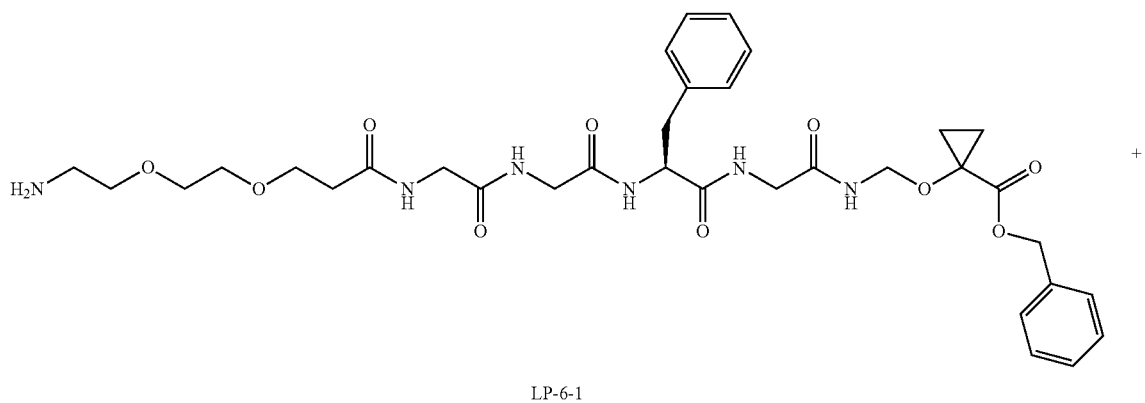

LP-6-1

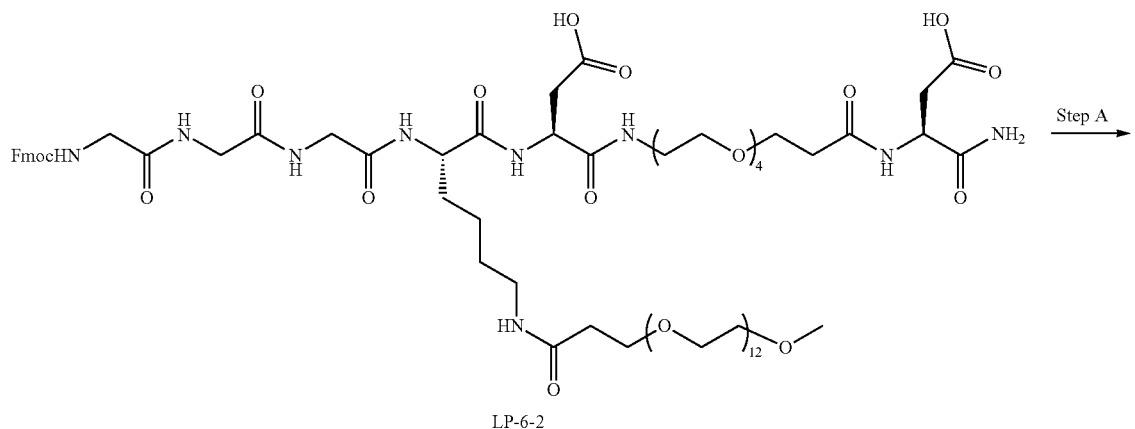

LP-6-2

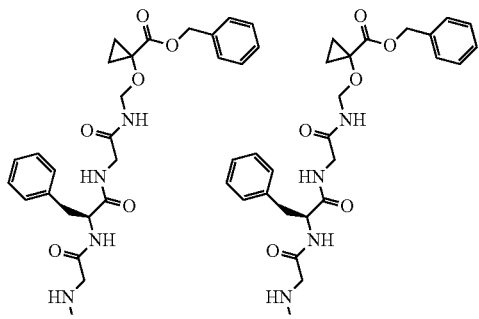

-continued
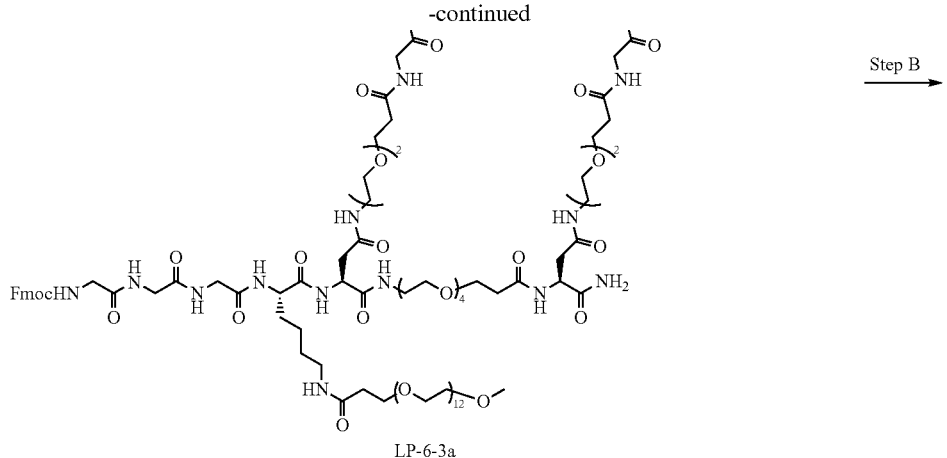
LP-6-3a
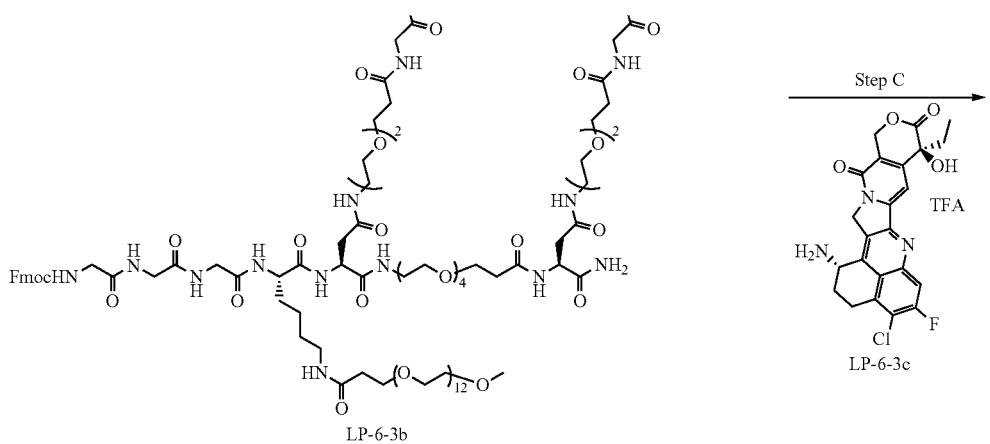
LP-6-3b
Step B →
Step C →
LP-6-3c
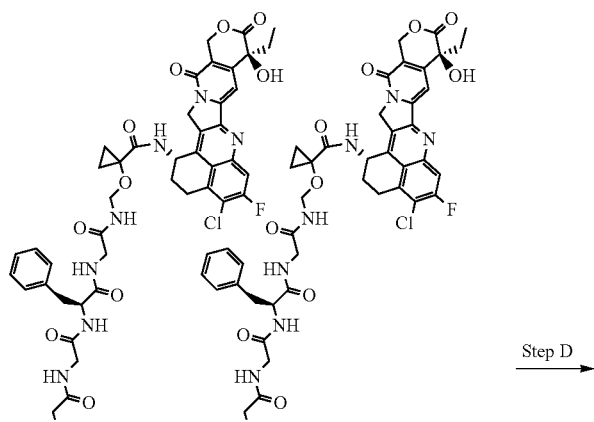
Step D →

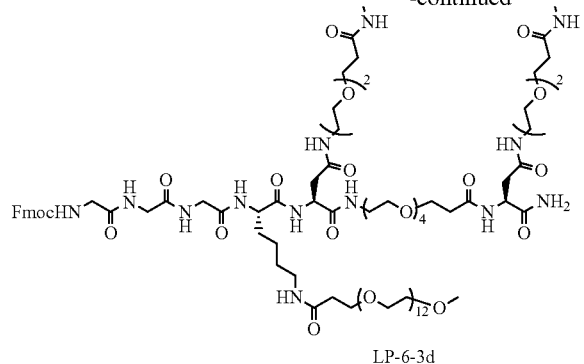

LP-6-3d

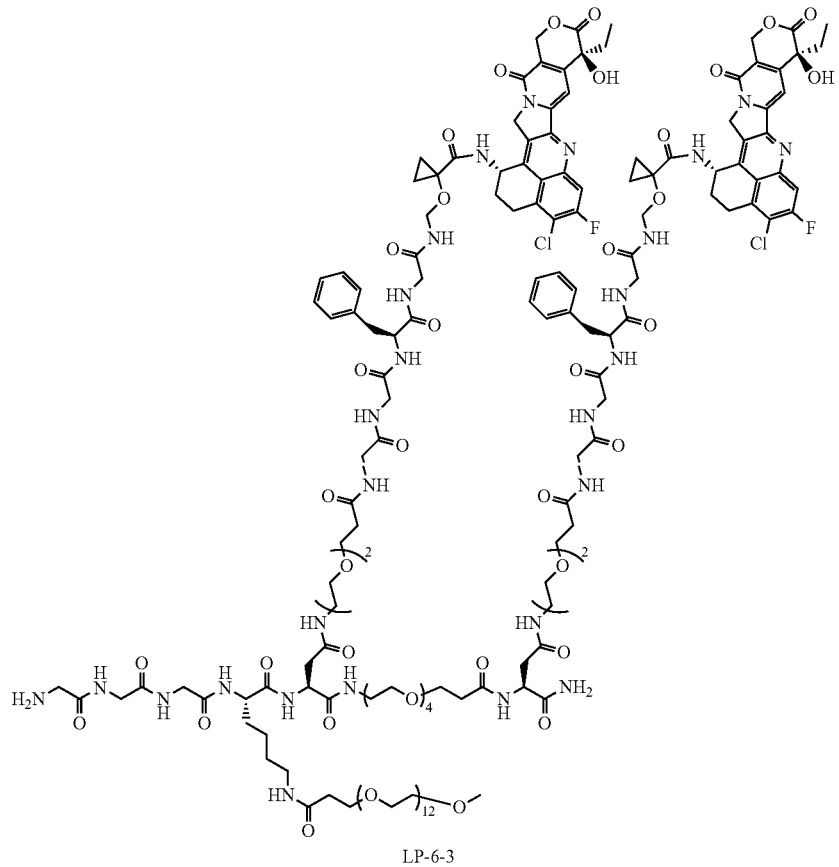

LP-6-3

Step A: Synthesis of Intermediate LP-6-3a

Compound LP-6-1 (2.2 equiv.) and compound LP-6-2 (1.0 equiv.) were added into a reaction flask, and dissolved in DMF. Subsequently, DIPEA (5.0 equiv.) was added and well stirred, and then, HATU (2.5 equiv.) was added into the system for reaction at room temperature. Monitoring by HPLC was performed until the reaction was complete (about 2 h). The reaction system was prepared directly by prep-HPLC. A preparation solution was freeze-dried to afford compound LP-6-3a (white solid, yield 52%). MS (ESI) m/z of $C_{143}H_{212}O_{48}N_{21}^{3+}$ $[M+3H]^{3+}$: calc 997.2, found 875.9 (some functional groups would shed after ionization).

Step B: Synthesis of Intermediate LP-6-3b

The compound LP-6-3a was dissolved in purified water, and a certain amount of palladium hydroxide (10 wt % $Pd(OH)_2$ on carbon) was added. The system was replaced with hydrogen three times and then stirred at room temperature for 1.5 h, during which, the extent of reaction was monitored, and the reaction was immediately stopped after the disappearance of raw materials to prevent the increase of de-Fmoc products. The reaction solution was filtered, and preparation by pre-HPLC was performed to afford compound LP-6-3b (white solid, yield 76%). MS (ESI) m/z of $C_{128}H_{200}O_{48}N_{21}^{3+}$ $[M+3H]^{3+}$: calc 937.1, found 875.9 (some functional groups would shed after ionization).

Step C: Synthesis of Intermediate LP-6-3d

The compound LP-6-3b (1.0 equiv.) and compound LP-6-3c (2.2 equiv.) were weighed and dissolved in DMF. DIPEA (5.0 equiv.) was added and well stirred. Subsequently, HATU (2.5 equiv.) was added for reaction at room temperature. Monitoring by HPLC was performed until the reaction was complete (about 16 h). The reaction system was prepared directly by prep-HPLC. A preparation solution was freeze-dried to afford compound LP-6-3d (yellow solid, yield 66%). MS (ESI) m/z of $C_{174}H_{232}O_{55}Cl_2F_2N_{27}{}^{3+}$ $[M+3H]^{3+}$: calc 1229.2, found 1229.3.

Step D: Synthesis of Compound LP-6-3

The compound LP-6-3d was dissolved in DMF, and diethylamine was added for reaction at room temperature. Monitoring by HPLC was performed until the reaction was complete (about 0.5 h). After the reaction was completed, the pH was regulated to neutral, then preparation by pre-HPLC was performed, and freeze drying was performed to afford compound LP-6-3 (yellow solid, yield 73%). MS (ESI) m/z of $C_{159}H_{222}O_{53}Cl_2F_2N_{27}{}^{3+}$ $[M+3H]^{3+}$: calc 1155.2, found 1155.3.

For the synthesis of compound LP-6-3c, please refer to patent CN202211428194.6.

(4) Synthesis of LP-6

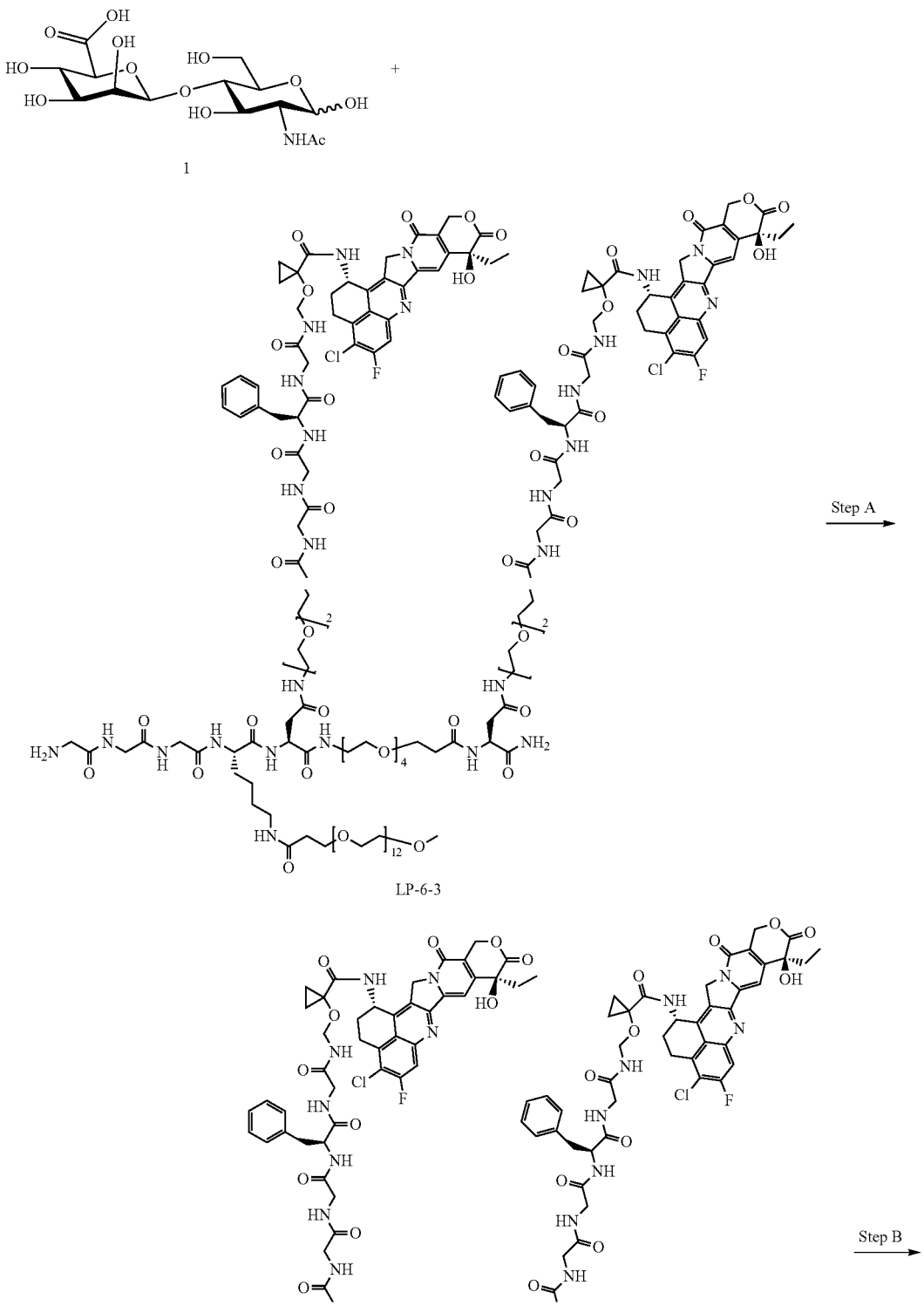

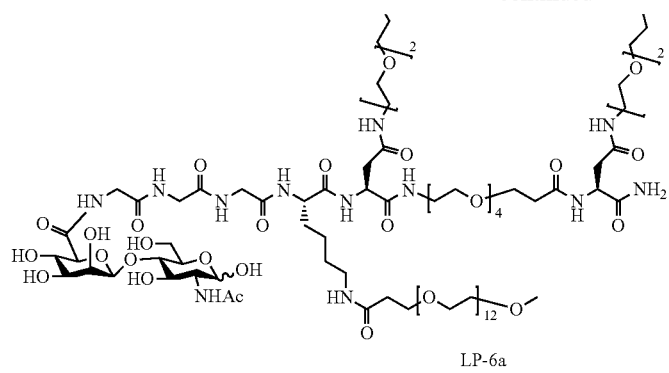
LP-6a
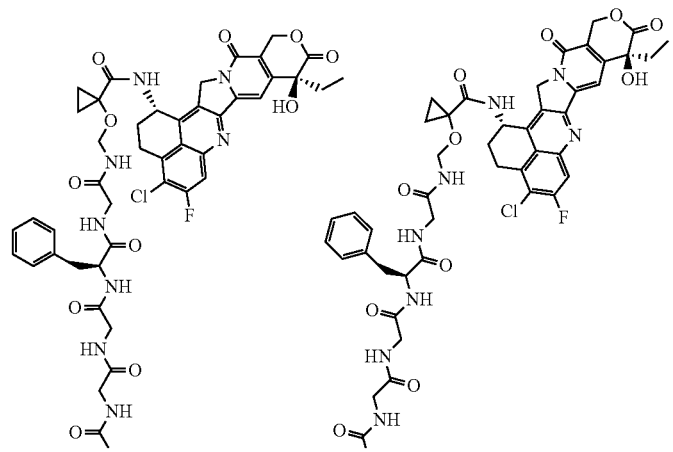
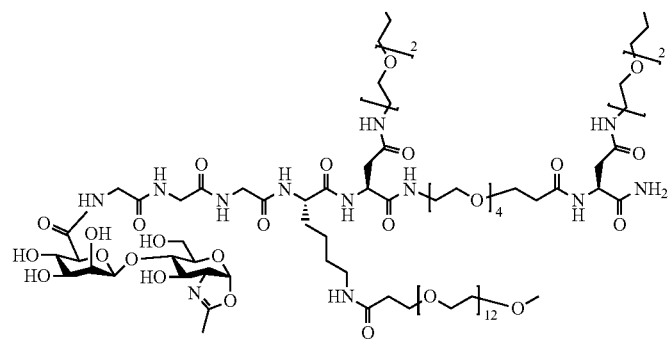
LP-6

Synthesis of LP-6a

The compound 1 (0.5 to 5.0 equiv.) and the compound LP-6-3 (1.0 equiv.) were dissolved in DMF. DIPEA (1 to 10 equiv.) was added and well stirred at 0° C. HATU (0.5 to 10 equiv.) was added. The reaction system was stirred at 0° C. The extent of reaction was monitored by HPLC until the reaction was complete (about 2 h). The reaction system was prepared directly by prep-HPLC. A preparation solution was freeze-dried to afford compound LP-66a (yellow solid, yield 63%). MS (ESI) m/z of $C_{173}H_{243}O_{64}Cl_2F_2N_{28}{}^{3+}$ [M+3H]$^{3+}$: calc 1281.5, found 1281.8.

Synthesis of LP-6

The compound LP-6a was weighed and dissolved in purified water. After the compound was stirred in an ice water bath and cooled, Et$_3$N (1 to 100 equiv.) and DMC (2-chloro-1,3-dimethylimidazolidinium chloride, CAS: 37091-73-9, 1 to 100 equiv.) were added. The extent of reaction was monitored by HPLC. After the reaction was complete, purification was performed by prep-HPLC. A preparation solution was freeze-dried to obtain compound LP-6 (light yellow solid, yield 74%). MS (ESI) m/z of $C_{173}H_{241}O_{63}Cl_2F_2N_{28}{}^{3+}$ [M+3H]$^{3+}$: calc 1275.5, found 1275.9.

Preparation of LP-7

LP-7 has a structure as follows:

LP-7

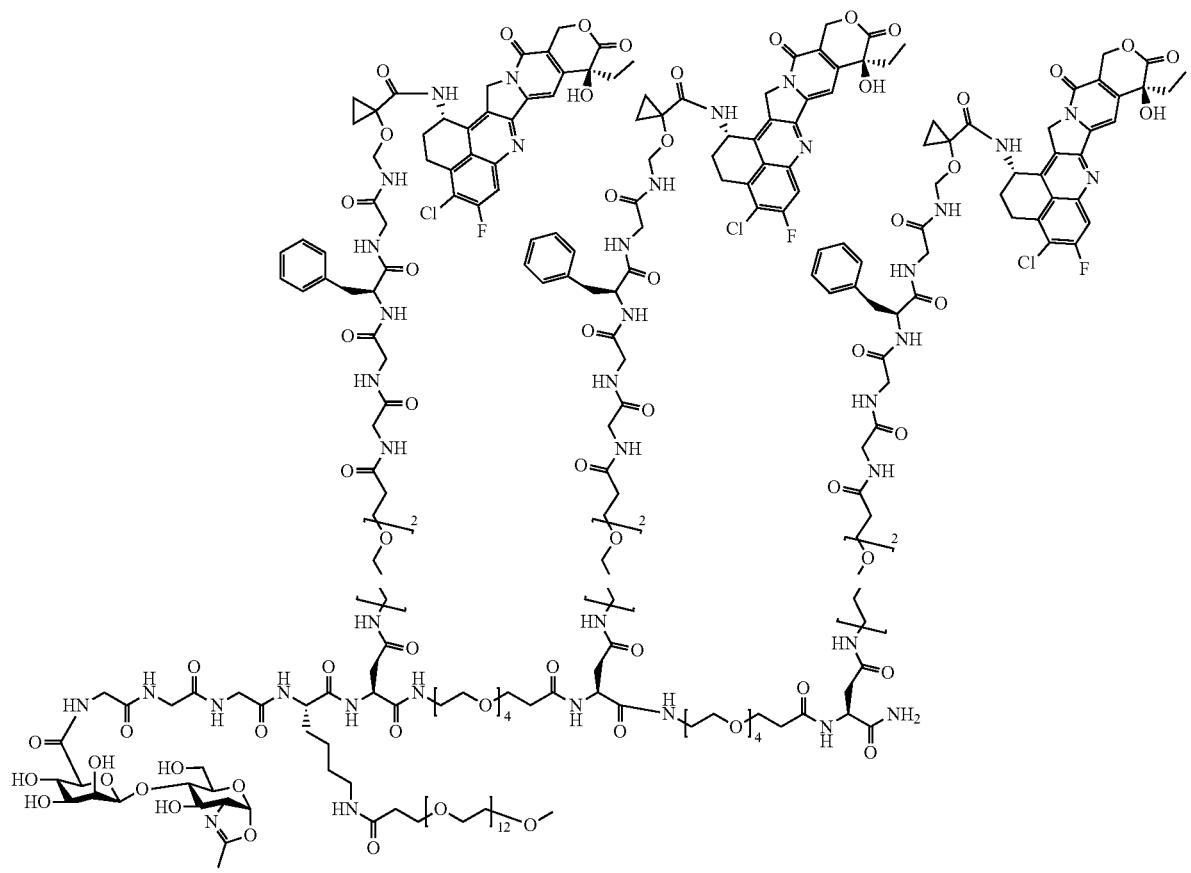

The synthesis route is as follows:
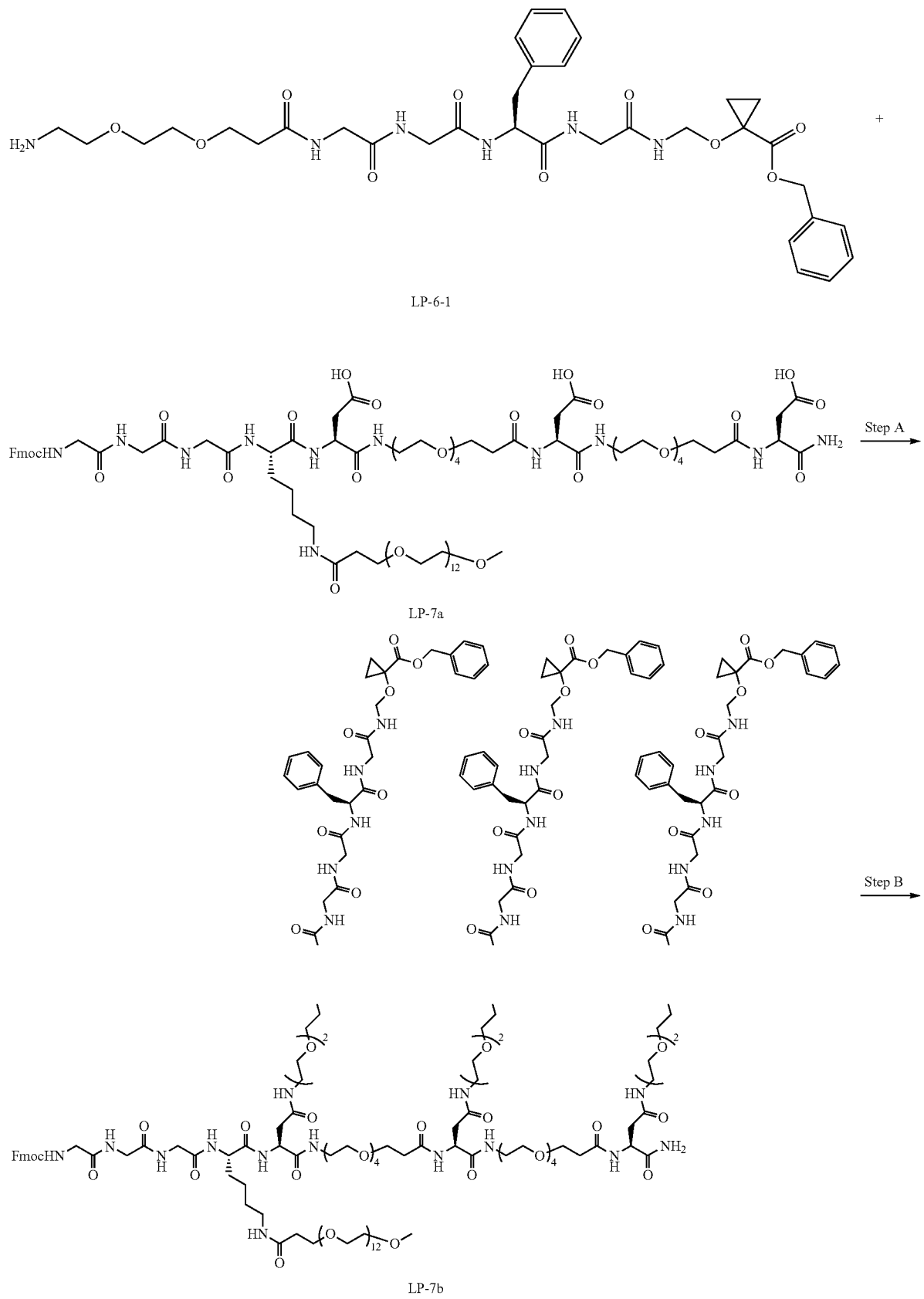
LP-6-1
LP-7a
Step A
LP-7b
Step B 103
104
-continued
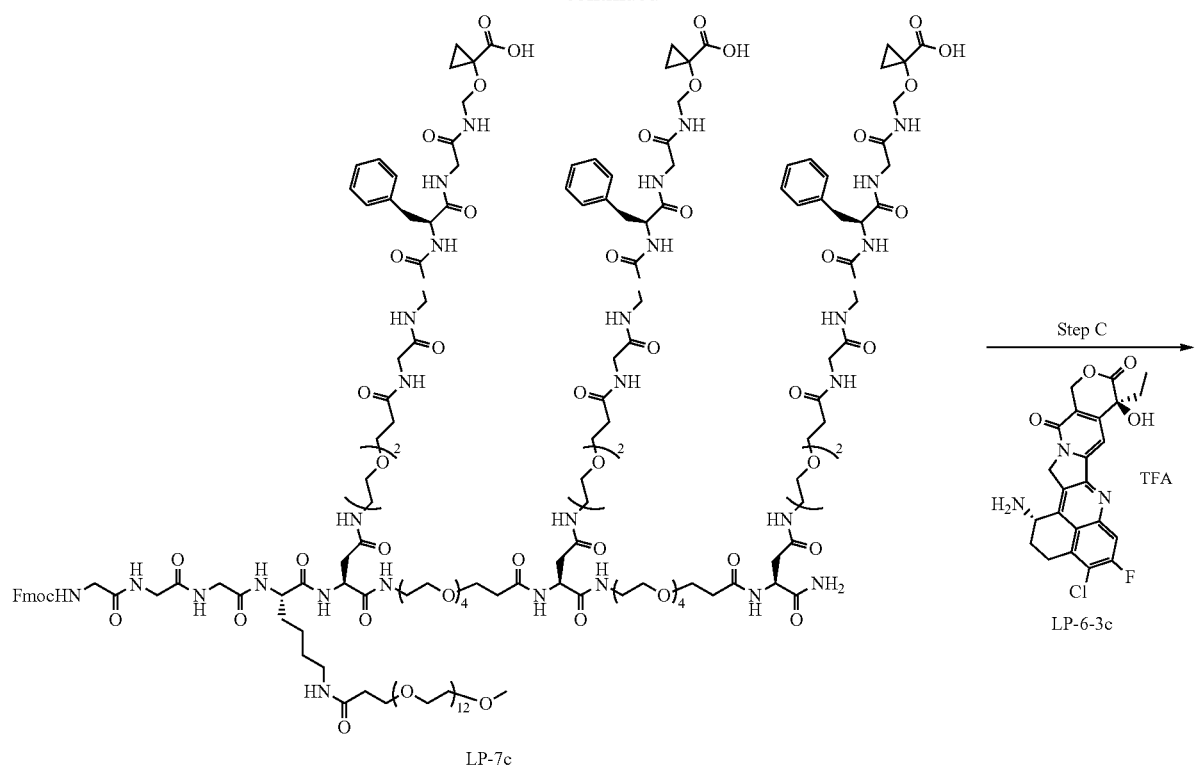
LP-7c
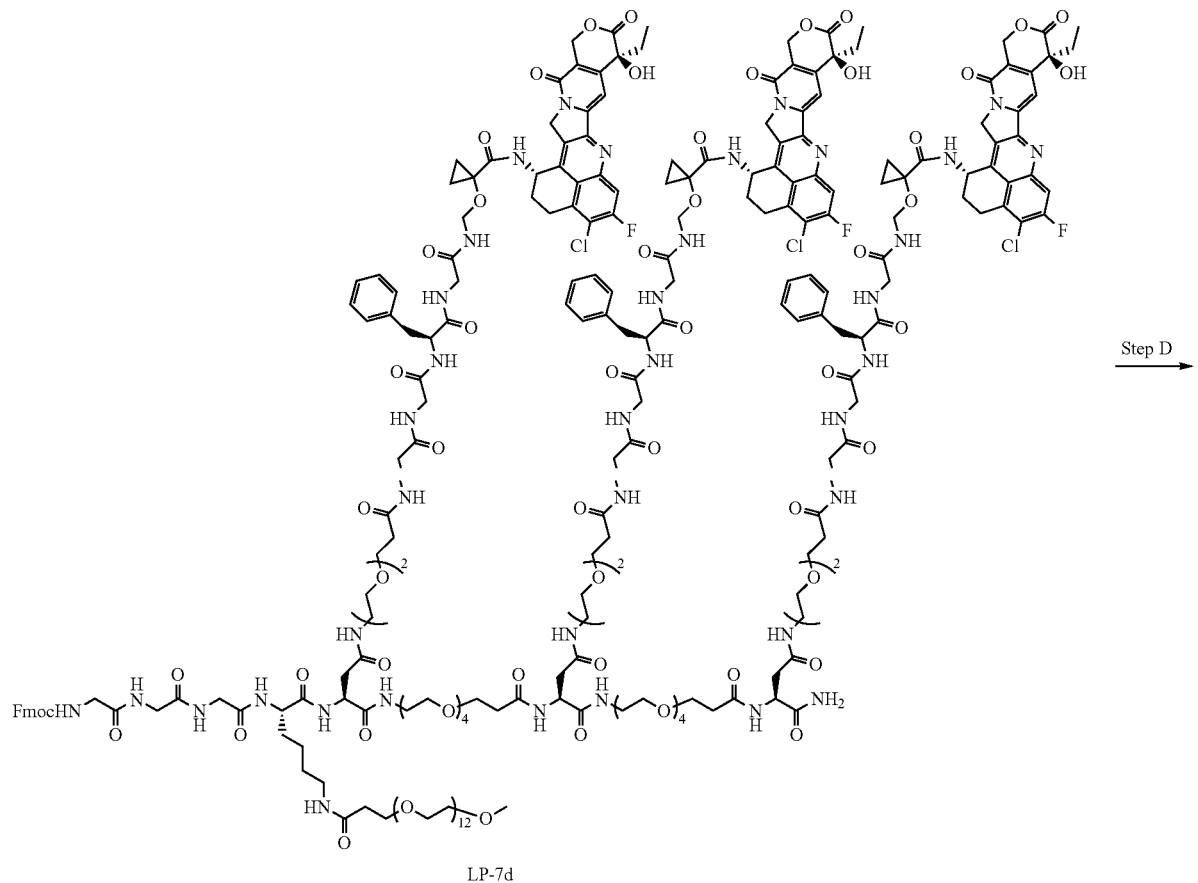
LP-7d

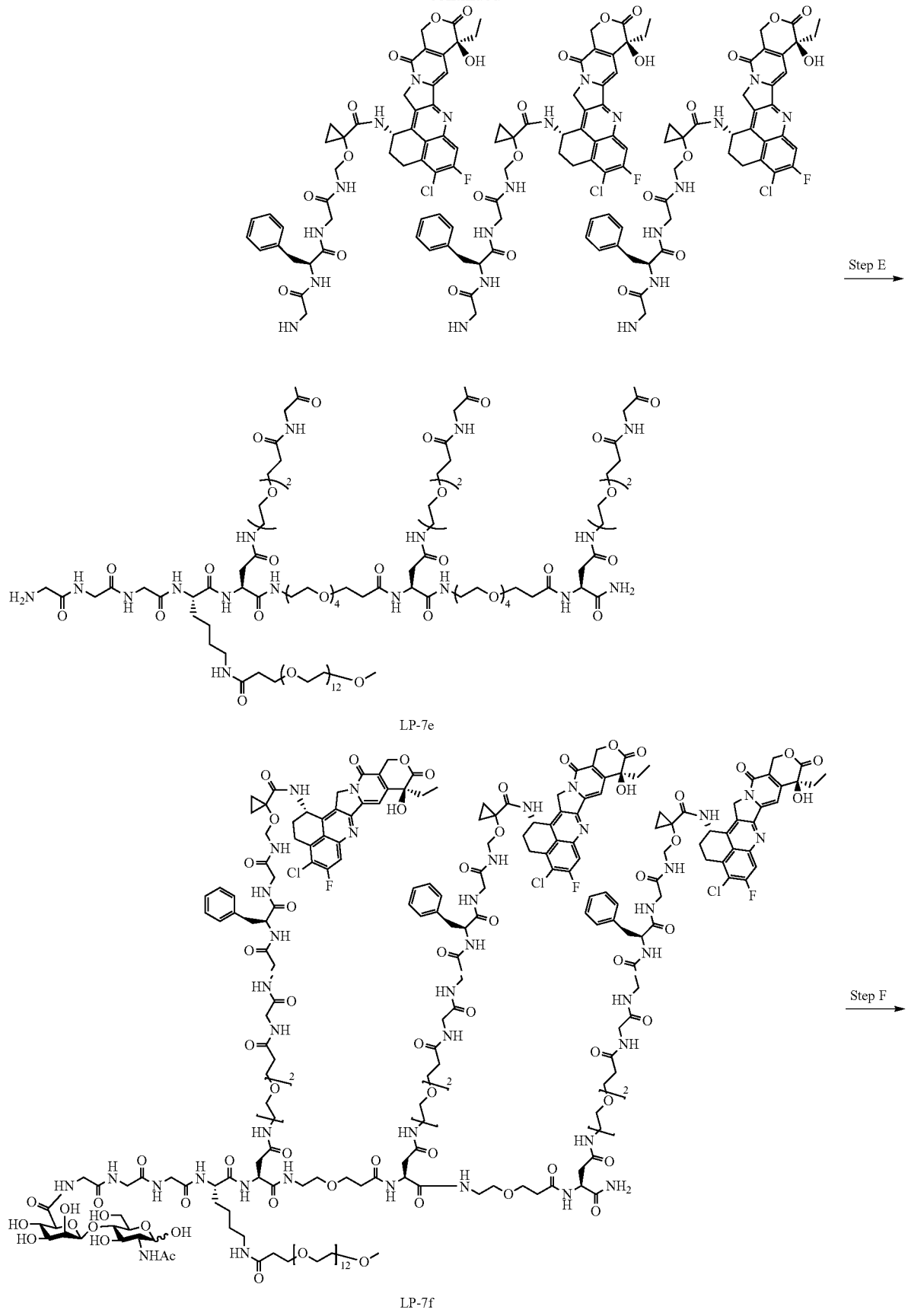

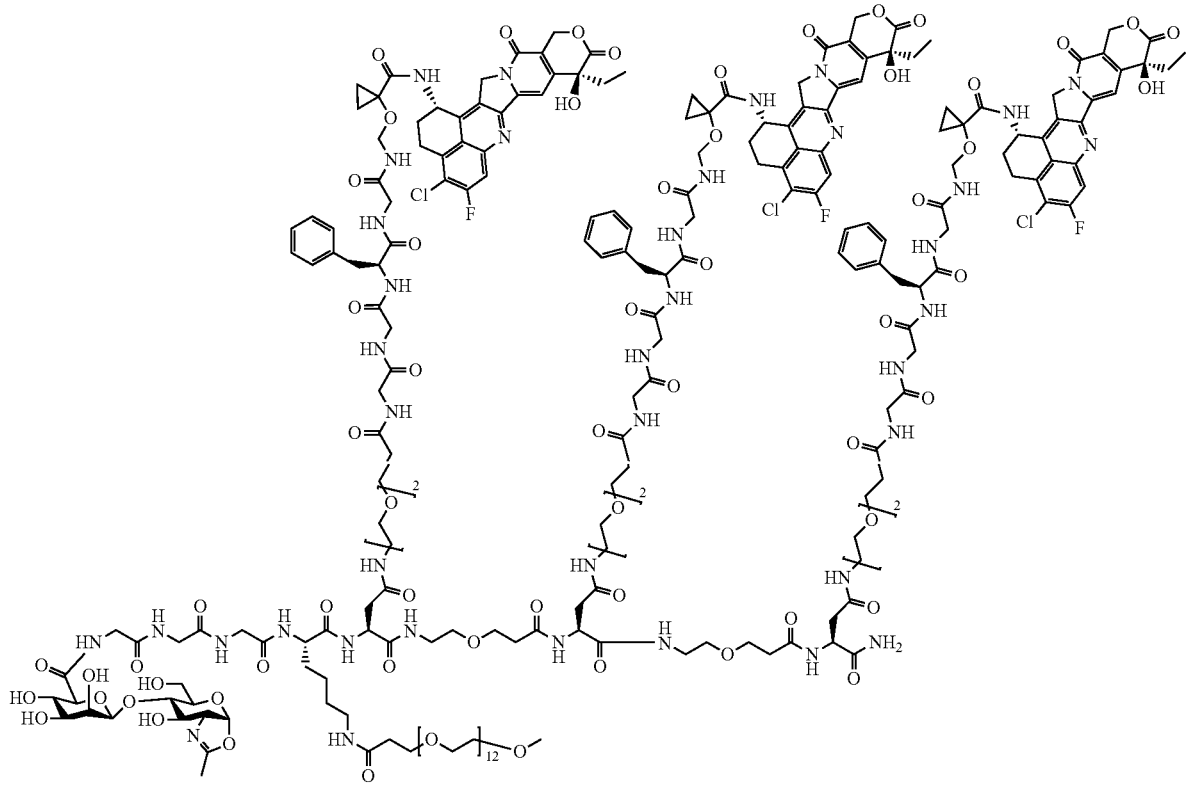

LP-7

Step A: Synthesis of Compound LP-7b

Compound LP-7a was synthesized by a method of polypeptide solid-phase synthesis, refer to a similar method of LP-6-2.

The compound LP-7a (1.0 equiv.) and the compound LP-6-1 (3.6 equiv.) were added into a reaction flask, and dissolved in DMF. Subsequently, DIPEA (6.0 equiv.) was added and well stirred, and then, HATU (3.6 equiv.) was added into the system for reaction at room temperature. Monitoring by HPLC was performed until the reaction was complete (about 2 h). The reaction system was prepared directly by prep-HPLC. A preparation solution was freeze-dried to afford compound LP-7b (white solid, yield 56%). MS (ESI) m/z of $C_{191}H_{280}O_{66}N_{29}^{3+}$ [M+3H]$^{3+}$: calc 1345.3, found 1345.8.

Step B: Synthesis of Intermediate LP-7c

The compound LP-7b was dissolved in purified water, and a certain amount of palladium hydroxide (10 wt % Pd(OH)$_2$ on activated carbon) was added. The system was replaced with hydrogen three times, and stirred at room temperature for 1.5 h, during which, the extent of reaction was monitored, and the reaction solution was prepared directly by prep-HPLC after being purified to afford compound LP-7c (white solid, yield 80%). MS (ESI) m/z of $C_{170}H_{262}O_{66}N_{29}^{3+}$ [M+3H]$^{3+}$: calc 1255.3, found 1255.9.

Step C: Synthesis of Intermediate LP-7d

The compound LP-7c (1.0 equiv.) and the compound LP-6-3 (1 to 10 equiv.) were weighed and dissolved in DMF. DIPEA (1 to 20 equiv.) was added and well stirred. Subsequently, HATU (1 to 10 equiv.) was added for reaction at room temperature. Monitoring by HPLC was performed until the reaction was complete (about 2 h). The reaction was directly used for a next reaction. MS (ESI) m/z of $C_{239}H_{313}O_{75}Cl_3F_3N_{38}^{3+}$ [M+3H]$^{3+}$: calc 1692.4, found 1692.9.

Step D: Synthesis of Compound LP-7e

The compound LP-7d was dissolved in DMF, and diethylamine was added for reaction at room temperature. Monitoring by HPLC was performed until the reaction was complete (about 0.5 h). After the reaction, the pH was regulated to neutral, then preparation by pre-HPLC was performed, and freeze drying was performed to afford compound LP-7e (yellow solid, yield 73%). MS (ESI) m/z of $C_{224}H_{303}O_{73}Cl_3F_3N_{38}^{3+}$ [M+3H]$^{3+}$: calc 1618.3, found 1618.5.

Step E: Synthesis of Compound LP-7f

The compound 1 (0.5 to 5.0 equiv.) and compound LP-7e (1.0 equiv.) were dissolved in DMF. DIPEA (1 to 10 equiv.) was added and well stirred at 0° C. HATU (0.5 to 10 equiv.) was added. The reaction system was stirred at 0° C. The extent of reaction was monitored by HPLC until the reaction was complete (about 2 h). The reaction system was prepared directly by prep-HPLC. A preparation solution was freeze-dried to afford compound LP-7f (yellow solid, yield 65%). MS (ESI) m/z of $C_{238}H_{325}O_{84}Cl_3F_3N_{39}^{4+}$ [M+4H]$^{4+}$: calc 1308.8, found 1309.0.

15.6 Step F: Synthesis of Compound LP-7

The compound LP-7f was weighed and dissolved in purified water. After the compound was stirred in an ice water bath and cooled, Et$_3$N (1 to 100 equiv.) and DMC (2-chloro-1,3-dimethylimidazolidinium chloride, CAS: 37091-73-9, 1 to 100 equiv.) were added. The extent of reaction was monitored by HPLC. After the reaction was complete, purification by prep-HPLC was performed. A preparation solution was freeze-dried to afford compound LP-7 (light yellow solid, yield 50%).

Example 4. Preparation of Anti-HeR$^2$ Antibody

For the production, purification and identification of an anti-human ErbB2/HeR$^2$ antibody T-LCCT$_L$-HC (mAb-1) and anti-human TROP2 antibody mAb-2, see Example 1 of Patent CN106856656B, which is incorporated in its entirety herein as a reference.

Example 5. Suspended Conjugation

Figure 3:
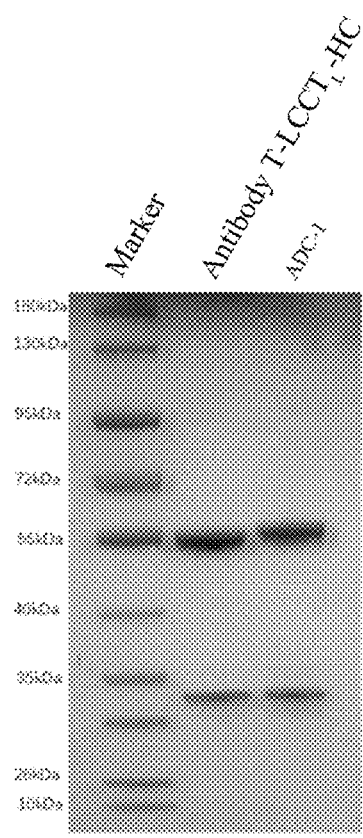
FIG. 3 is an SDS-PAGE electropherogram showing a product obtained by using the endoglycosidase fusion protein (Halo-Endo S2-His) of the present disclosure in a suspended conjugation reaction.
Figure 4:
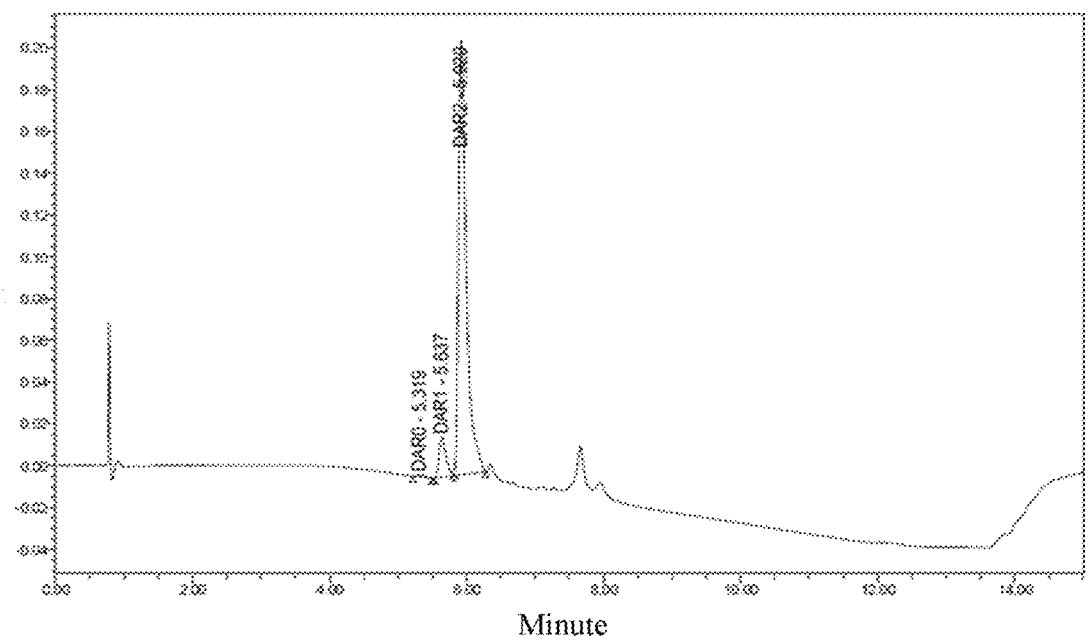
FIG. 4 is an HIC-HPLC chromatogram showing a product obtained by using the endoglycosidase fusion protein (Halo-Endo S2-His) of the present disclosure in a suspended conjugation reaction.

Solid Phase Preparation of ADC-1
ADCs were prepared based on a conjugation reaction between a Halo-Endo S2-His catalytic antibody and a linker-payload. In an endonuclease buffer, the antibody was fully mixed with the linker-payload in an appropriate molar ratio (1:1 to 1:100), a Halo-Endo S2-His medium was added, and well mixing was performed. The conjugation reaction in the well mixed state was carried out at 4° C. to 40° C. for 0.5 to 20 h. After the reaction ended, centrifuging was performed, a solid-phase conjugation reaction mixture was taken out, and the mixture was purified, ultrafiltered or dialyzed to remove an unreacted drug intermediate. Purified ADC1 was stored in 1× PBS pH 7.4 at 4° C. or −80° C.
1) SDS-PAGE Detection Analysis
After the conjugation reaction ended, the purity and conjugation efficiency of ADC-1 could be detected by an SDS-PAGE method. The SDS-PAGE detection results of ADC1 are as shown in FIG. 3. The conjugation reaction occurs on heavy chains of an antibody in a site-specific manner (the heavy chain conjugated with cytotoxin has a significant molecular weight transition compared with a heavy chain unconjugated with the cytotoxin), no heavy chains unconjugated with the cytotoxin are detected in a conjugated product, and the conjugation efficiency is up to 95% or above.
2) HIC-HPLC Detection Analysis
HIC-HPLC: Proteomix HIC Butyl-NP5 4.6*100 mm 5 µm Non-Porous column; column temperature 30° C.; mobile phase A: 1.5 M ammonium sulfate+20 mM phosphate buffer salt, pH 7.0; mobile phase B: 20 mM phosphate buffer salt: isopropanol=7:3 (v/v); flow rate 0.8 mL/min; gradient method: phase B increased from 10% to 100% within 8 min; and 280 nm was selected as the detection wavelength to detect the DAR distribution of ADC1.
The detection results are as shown in FIG. 4 and Table 2. Antibodies unconjugated with the compound LP-1 are less than 1%. The conjugated product is mainly DAR$^2$, and the DAR value of ADC-1 is 1.93.

TABLE 2

Halo-Endo S2-His Conjugation Efficiency Table

| DAR0 Area (%) | DAR1 Area (%) | DAR2 Area (%) | DAR | Conjugation efficiency |
|---|---|---|---|---|
| 0.16 | 6.43 | 93.4 | 1.93 | 96.5% |

The conjugation efficiency in Table 2 is 1.93/2=96.5%
3) Mass Spectrometry
High-precision molecular weight mass spectrometry (ESI-MS) analysis of ADC-1
ADC-1 was analyzed and detected by using high-precision molecular weight mass spectrometry. The analysis and detection results show that the apparent molecular weight is 150539.27 and the theoretical molecular weight is 150538.78, which meets expectation, thereby confirming that an Fc end of each heavy chain is conjugated with one cytotoxin molecule.

Example 6. Column Conjugation

An antibody reaction solution and a small molecule toxin (LP-1) reaction solution are prepared, respectively. The antibody reaction solution had a concentration of 1 to 100 mg/ml, and the small molecule reaction solution had a concentration of 0.1 to 50 mg/ml. A treated immobilized enzyme (Halo-Endo S2-His) medium was packed, heated to 10° C. to 40° C. through air or water bath conduction, and preheated for more than 30 min in advance. The antibody reaction solution and the small molecule reaction solution were mixed evenly in a fixed proportion, and reacted through a conjugation column. The effluent was the ADC. The retention time of the conjugation column was 5 min to 24 h. Samples of a conjugation reaction solution were subjected to SDS-PAGE, HIC-HPLC detection, and RP-HPLC detection.
1) SDS-PAGE Detection Analysis
After the conjugation reaction ended, the purity and conjugation efficiency of ADC-1 could be detected by an SDS-PAGE method. The SDS-PAGE detection results of ADC-1 show that the conjugation reaction occurs on heavy chains of an antibody in a site-specific manner, no heavy chains unconjugated with the cytotoxin are detected in a conjugated product, and the conjugation efficiency is up to 95% or above.
2) HIC-HPLC Detection Analysis
The detection results show that DAR of ADC-1 after the conjugation reaction is 1.93, and the conjugation efficiency is 96.5%.
The efficiency of both the column conjugation and the suspended conjugation can reach 95% or above, and the results of the column conjugation are used for supporting the linear production scale-up of ADCs.
The specific operation flow of the column conjugation is as follows: an appropriate tube (such as a silicone hose of a peristaltic pump) was installed to an appropriate pump head (such as peristaltic pump head (Chongqing Jieheng, BT-600CA/DG4 (10))) for tube equilibration. Then an outlet end of the tube was connected to an inlet end of the conjugation column, and another section of tube was connected to a lower end of the conjugation column. The connected conjugation column was placed in a temperature control device (such as a hybridizer (UVP/HB-1000 Hybridizer)) with a temperature set at 10° C. to 40° C., and the outlet end of the tube at the lower end of the conjugation column was placed outside the temperature control device. The inlet end of the tube was placed in the conjugation reaction solution, the pump speed was enabled for the conjugation reaction, and a conjugation reaction solution was collected. After the conjugation reaction solution was loaded, the conjugation column was flushed with a conjugation equilibration buffer, and collection was performed according to the same collection volume. The effluent was the ADC. After the collection, the concentration of the collected solution was detected with an ultraviolet spectrophotometer, and the collected solution was purified, ultrafiltered or dialyzed to remove an unreacted drug intermediate. Purified ADC was stored in 1× PBS pH 7.4 at 4° C. or −80° C. Samples of a conjugation reaction solution were subjected to SDS-PAGE, HIC-HPLC or RP-HPLC detection.

A solid-phase conjugation column reaction enabled linear scale-up. Under the condition of ensuring that key process parameters (e.g., retention time) are the same, a corresponding process (e.g., pump flow rate) was adjusted according to the size of the conjugation column, thereby achieving that the conjugation column was linearly scaled up to several hundred milliliters (500 mL), several liters (3 L), or larger volumes. Glycosidase conjugation column catalysis and off-line DAR detection were achieved on a laboratory scale. A larger conjugation column was employed to achieve linear scale-up of drug conjugate at a higher flow rate and online DAR value detection. The conjugation device in patent application WO2022170676A is applicable to the glycosylation process of the present disclosure. The feasibility of applying conjugation devices of different scales to a glycosylation conjugation platform was verified in this example.

Example 7. Isolation of Halo-Endo S2-His and ADC

When the pH value of the environment was higher than its isoelectric point, the protein would bind to positively charged packing, namely an anion exchanger. While when the pH value of the environment was lower than its isoelectric point, the protein would bind to negatively charged packing, namely a cation exchanger. The isoelectric point of Halo-Endo S2-His was 5.5. Under the condition of pH 6.0 to pH 8.0, the surface of a Halo-Endo S2-His protein was negatively charged. The Halo-Endo S2-His protein would not bind to negatively charged packing, i.e., a cation exchanger in a flow-through mode. The Halo-Endo S2-His protein would bind to positively charged packing, namely an anion exchanger. The isoelectric point of ADC was generally 8 to 9. Under the condition of pH 6.0 to pH 8.0, the surface of ADC protein was positively charged. ADC would bind to negatively charged packing, i.e., a cation exchanger. ADC would not bind to positively charged packing, i.e., an anion exchanger in a flow-through mode. There was a significant difference of greater than 2 in isoelectric point between Halo-Endo S2-His and ADC. The buffer (pH 6.0 to pH 8.0) was selected to effectively isolate ADC and Halo-Endo S2-His by ion exchange chromatography. That is, site-specific catalysis of ADC was performed with Halo-Endo S2-His. Even if a small amount of Halo-Endo S2-His protein immobilized on the column was shed into an ADC product, it could be eliminated by subsequent anion cation chromatography.

1) Anion Chromatography (AEX)

Q Sepharose FF packing was selected for packing, and 20 mM Tris-HCl (pH 7.5) was employed to equilibrate a chromatography column, and sample loading was performed. After the sample loading, 20 mM Tris HCl (pH 7.5) was further employed to equilibrate to baseline. Finally, samples were eluted with 20 mM Tris-HCl and 1 M NaCl (pH 7.5), and CIP (cleaning) was performed with 1 M NaOH. Purification of ADC and Halo-Endo S2-His was performed using the same method and packing, and ADC-1 and Halo-Endo S2-His were mixed and then purified.

Figure 5A:
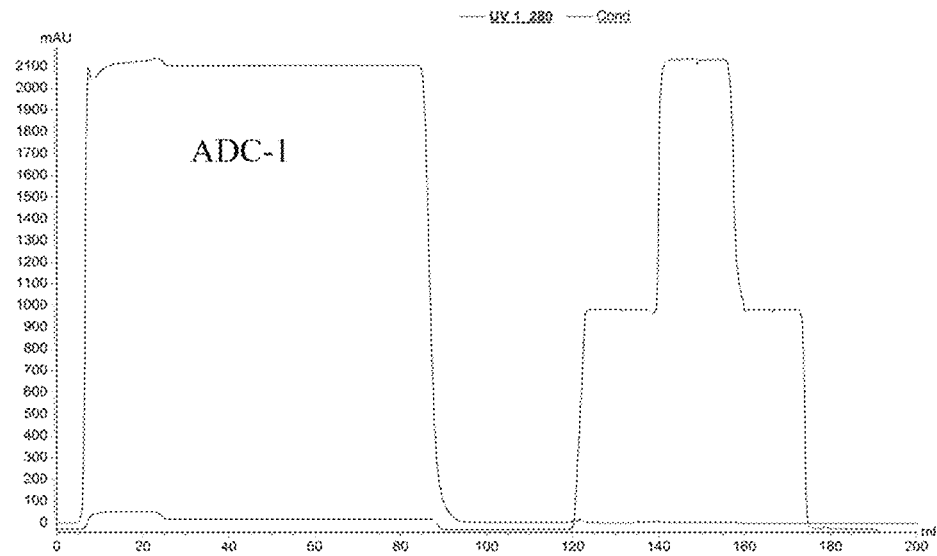
FIG. 5A is a profile showing that ADC is purified by Q Sepharose FF.

The results are as shown in FIG. 5A: ADC-1 samples are subjected to a flow-through mode of a Q FF chromatography column under the condition of pH 7.5.

Figure 5B:
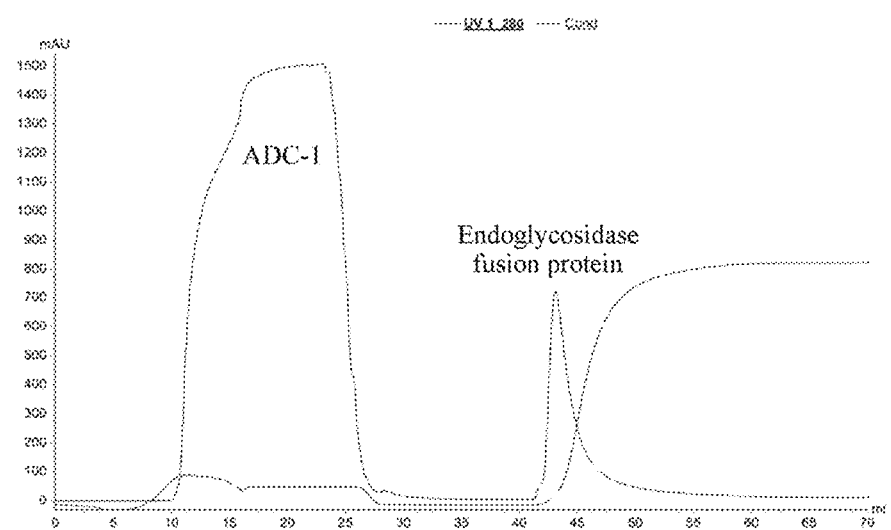
FIG. 5B is a profile showing that ADC and an endoglycosidase fusion protein are purified by Q Sepharose FF.

Halo-Endo S2-His samples are subjected to a binding mode of the Q FF chromatography column under the condition of pH 7.5, and eluted with 20 mM Tris-HCl, and 1 M NaCl (pH 7.5). As shown in FIG. 5B, ADC-1 and Halo-Endo S2-His mixed loaded samples can be efficiently isolated after passing through the Q FF chromatography column, wherein ADC-1 flows through, and Halo-Endo S2-His attaches the column.

2) Cation Chromatography (CEX)

Capto S impact cationic packing was selected for packing, 20 mM citric acid/citric sodium (pH 6.2) was employed to equilibrate a chromatography column, and sample loading was performed. After the sample loading, 20 mM citric acid/citric sodium (pH 6.2) was further employed to equilibrate to baseline. Finally, samples were eluted with 20 mM citric acid/citric sodium and 160 mM NaCl (pH 6.2). The chromatography column was regenerated with 20 mM citric acid/citric sodium and 1 M NaCl (pH 6.2), and chromatography column CIP was performed with 1 M NaOH. Purification of ADC and Halo-Endo S2-His was performed using the same method and packing, and ADC and Halo-Endo S2-His were mixed and then purified.

Figure 6A:
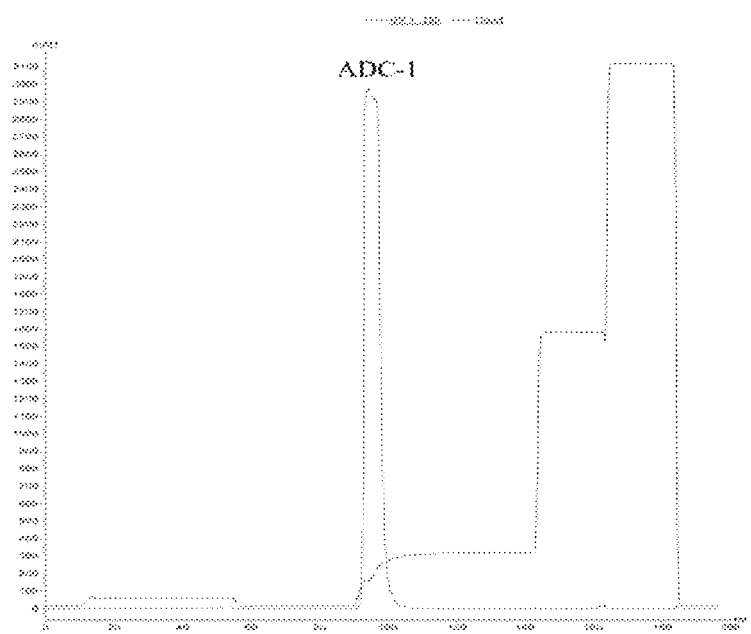
FIG. 6A is a profile showing that ADC is purified after attaching column Capto S impact.

The results are as shown in FIG. 6A: ADC-1 samples are subjected to a binding mode of a Capto S impact cation chromatography column under the condition of pH 6.2.

Figure 6B:
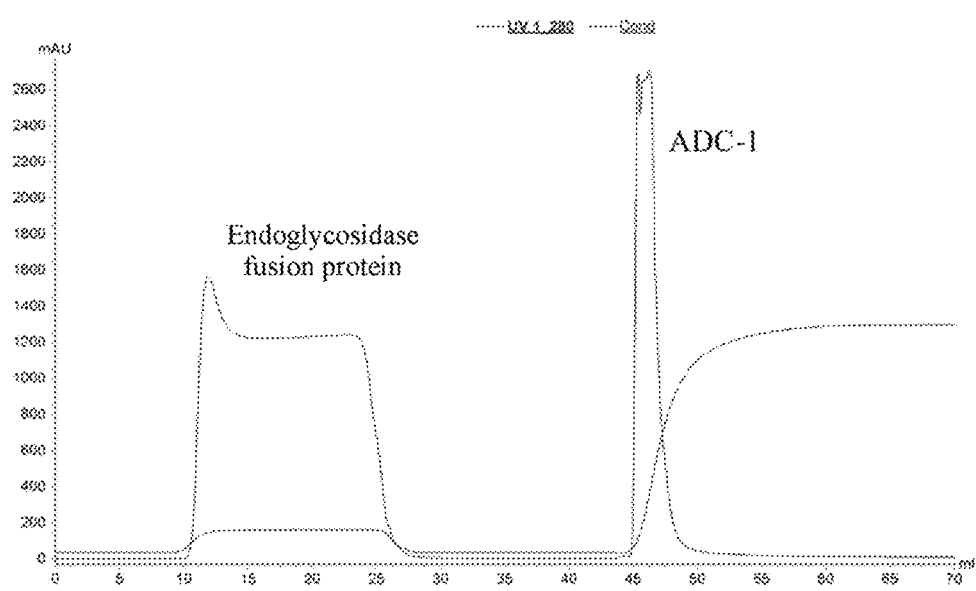
FIG. 6B is a profile showing that ADC and an endoglycosidase fusion protein are purified after attaching column Capto S impact.

Halo-Endo S2-His samples are subjected to a flow-through mode of the Capto S impact cation chromatography column under the condition of pH 7.5. As shown in FIG. 6B, ADC-1 and Halo-Endo S2-His mixed loaded samples can be efficiently isolated after passing through the Capto S impact cation chromatography column, wherein ADC-1 attaches column, and Halo-Endo S2-His flows through.

Example 8. Detection of Affinity of ADC-1 for Cell Surface ErbB2/Her2

HeR$^2$ ECD was taken, prepared with a CBS coating buffer (0.1 M carbonate buffer, pH 9.6) to be 1 μg/ml, with 100 μl per well, and coated at 25° C. for 60 min. After the coating, a plate was washed with PBST three times, the plate was blocked (300 μl/well) with a blocking buffer (5% skimmed milk powder) at 25° C. and 200 rpm, and incubation was performed for 60 min. After the blocking, the plate was washed with PBST three times, antibody T-LCCT$_L$-HC and ADC-1 (100 μl/well) were added, the plate was placed at 25° C., and incubation was performed under the condition of 200 rpm for 60 min. After incubation with the sample, the plate was washed with PBST three times, anti-human IgG Fc-HRP was added, with 100 μL per well and incubation was performed at 25° C. and 200 rpm for 60 min. After incubation for 60 min, color development was performed with TMB (100 μl/well) for 5 min, then the reaction was stopped with a stop buffer, and reading was performed at OD450.

Figure 7:
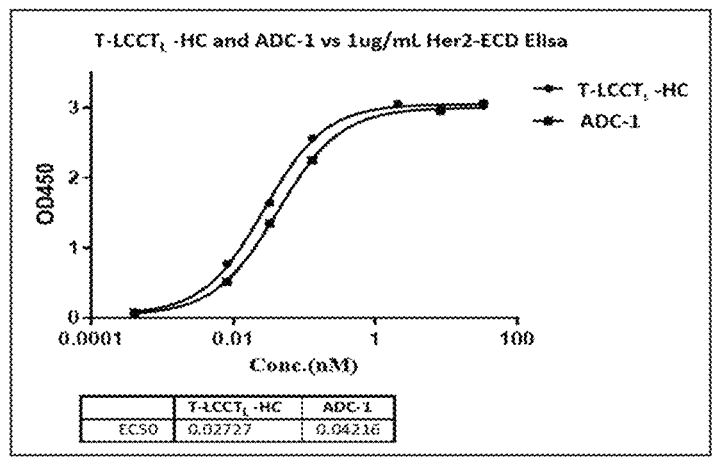
FIG. 7 shows detection of affinity of ADC-1 for extracellular ErbB2/HeR$^2$ (EC50, nM).

The Elisa test results show that there is no significant difference in antigen affinity between T-LCCT$_L$-HC nude monoclonal antibody and ADC-1 for HeR$^2$ ECD, as shown in FIG. 7.

Example 9. Influence of ADC-1 on Proliferation of Tumor Cells at Different Expression Levels of ErbB2/Her2

1) ErbB2/Her2-positive human breast cancer cells BT-474, ErbB2/Her2-positive human gastric cancer cells NCI-N87 and ErbB2/Her2-negative human liver cancer cells HepG2 were inoculated into a 96-well cell plate at 100 μl/well (1000 to 10000 cells), and incubated overnight in a cell incubator under the conditions of 37° C., 5% CO$_2$, and 100% humidity.
2) Different concentrations (10, 3.3, 1.1, 0.37, 0.12, 0.041, 0.014, 0.0046, 0.0015, and 0.00051 nM) of ADC-1 or antibody T-LCCT$_L$-HC or different concentrations (30, 10, 3.3, 1.1, 0.37, 0.12, 0.041, 0.014, 0.0046, and 0.0015 nM) of MMAE (monomethylauristatin E) were added to ErbB2/Her2-positive cells cultured overnight; different concentrations (100, 10, 3.3, 1.1, 0.37, 0.12, 0.041, 0.014, 0.0046, and 0.0015 nM) of ADC-1 or antibody T-LCCTL-HC or different concentrations (30, 10, 3.3, 1.1, 0.37, 0.12, 0.041, 0.014, 0.0046, and 0.0015 nM) of MMAE were added to the ErbB2/Her2-negative cells cultured overnight; and puromycin with a concentration of 50 μM was added to the control group. Incubation was further performed at 37° C. for 72 to 120 h. 3) The cell plate was removed from the 37° C. cell incubator, and equilibrated for about 30 min to room temperature. 100 μl of CellTiter Glo reagent was added into each well, a shaker shook for 2 min, followed by standing in a dark place at room temperature for 10 min, and a relative light unit (RLU) was measured with an MD M4 microplate reader.

Figure 8:
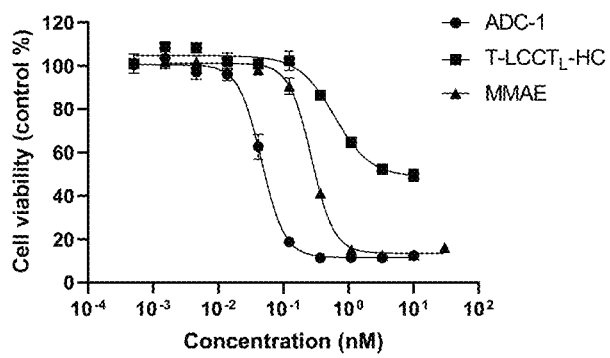
FIG. 8 shows inhibitory effect of different drugs on proliferation of tumor cells BT474 (IC50, nM).
Figure 9:
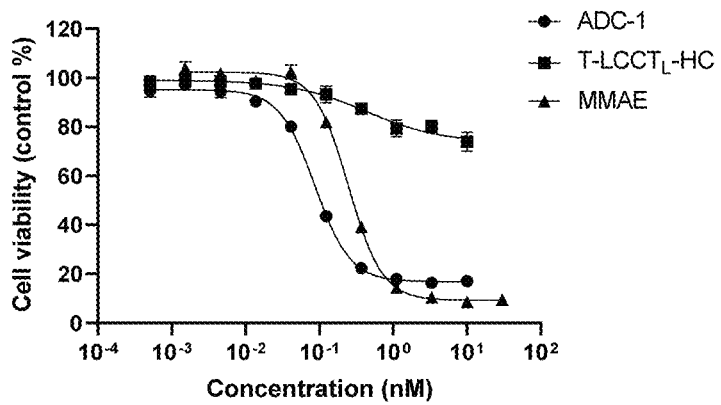
FIG. 9 shows inhibitory effect of different drugs on proliferation of tumor cells NCI-N87 (IC50, nM).
Figure 10:
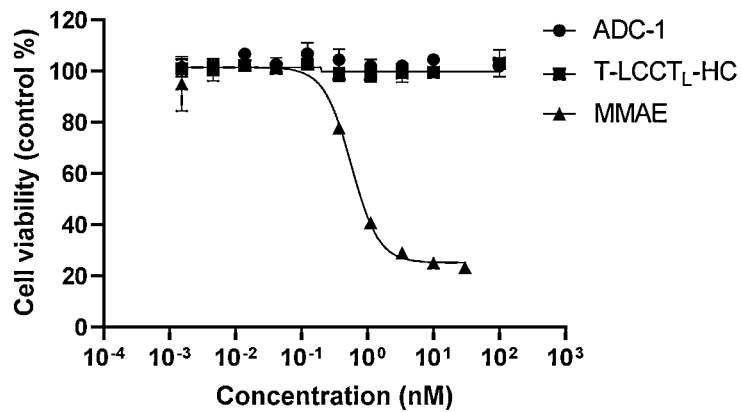
FIG. 10 shows inhibitory effect of different drugs on proliferation of tumor cells HepG2 (IC50, nM).

4) The results of the inhibitory effect of different drugs on proliferation of the tumor cells are shown in Table 3 and FIGS. 8 to 10, wherein ADC1 and MMAE small molecule toxins have obvious inhibitory effect on proliferation of the ErbB2/Her2-positive cells, the antibody T-LCCT$_L$-HC monoclonal antibody has slight inhibitory effect on proliferation of the ErbB2/Her2-positive cells, and ADC-1 is significantly superior to the T-LCCT$_L$-HC monoclonal antibody and the MMAE small molecule toxin. ADC-1 and T-LCCT$_L$-HC monoclonal antibodies have no inhibitory effect on the ErbB2/Her2-negative cells.

TABLE 3

Inhibitory effect of Different Drugs on proliferation of Tumor Cells ($IC_{50}$, nM)

| | ADC-1 | Antibody T-LCCT$_L$-HC | MMAE |
|---|---|---|---|
| BT-474 | 0.04636 | 0.6093 | 0.2715 |
| NCI-N87 | 0.08706 | 0.4251 | 0.2481 |
| HepG2 | — | — | 0.5669 |

Note:
"—" undetected

Example 10: In Vivo Activity Test of ADC-1 (NCI-N87 CDX Mouse Model)

The influence of ADC-1 on the tumor cell growth of an ErbB2/HER$^2$ NCI-N87 CDX mouse model was tested using the following methods 1) Cell culture: NCI-N87 human gastric cancer tumor cells (ATCC, Manassas, VA, cat #CRL-5822) at logarithmic phase were collected, the cell density was adjusted with a matrix gel buffer (PBS:Matrigel=1:1), and 0.2 mL of NCI-N87 cell suspension prepared was subcutaneously injected into right shoulder blades of 7 to 9-week-old SPF-grade female BALB/c nude mice, with a cell inoculum size of $10 \times 10^6$/mouse.

2) The tumor diameter was measured with a vernier caliper, and the tumor volume was calculated according to the formula V=0.5 a*b2 (where a is the longest diameter of the tumor and b is the shortest diameter of the tumor). After 5 days of cell inoculation, when the mean tumor volume range was 100 to 300 mm$^3$, animals were randomly divided into a vehicle control group and ADC-1 3 mg/kg treatment group, with 5 animals in each group. Animals were administered via caudal veins, and the control group was given an equal volume of vehicle, and the day when the animals were grouped and administrated was defined as Day0. The tumor volume of the animal in each group was measured twice a week within 35 days after administration. The tumor volumes of the animals on the day 35 were compared between groups, and the T/C value and TGI value were calculated with the tumor volume. The calculation formula was as follows: T/C %=$T_{RTV}$V/$C_{RTV}$×100% ($T_{RTV}$: treatment group RTV; $C_{RTV}$: vehicle control group RTV). The relative tumor volume (RTV) was calculated according to the results of tumor measurements. The calculation formula was RTV=Vt/V0, with V0 representing an average tumor volume measured at the time of grouping, Vt representing an average tumor volume at a certain measurement, and $T_{RTV}$ and $C_{RTV}$ were taken from data of the same day. Calculation of TGI (%): TGI (%)=[1−(average tumor volume at the end of treatment in a treatment group−average tumor volume at the start of administration in this treatment group)/(average tumor volume at the end of treatment in a vehicle control group−average tumor volume at the start of treatment in the vehicle control group)]×100%.

3) Statistic analyses were performed on data between groups by using independent sample t-tests, and all the analyses were performed by using SPSS 17.0. $P<0.05$ indicates that the difference is statistically significant.

Figure 11:
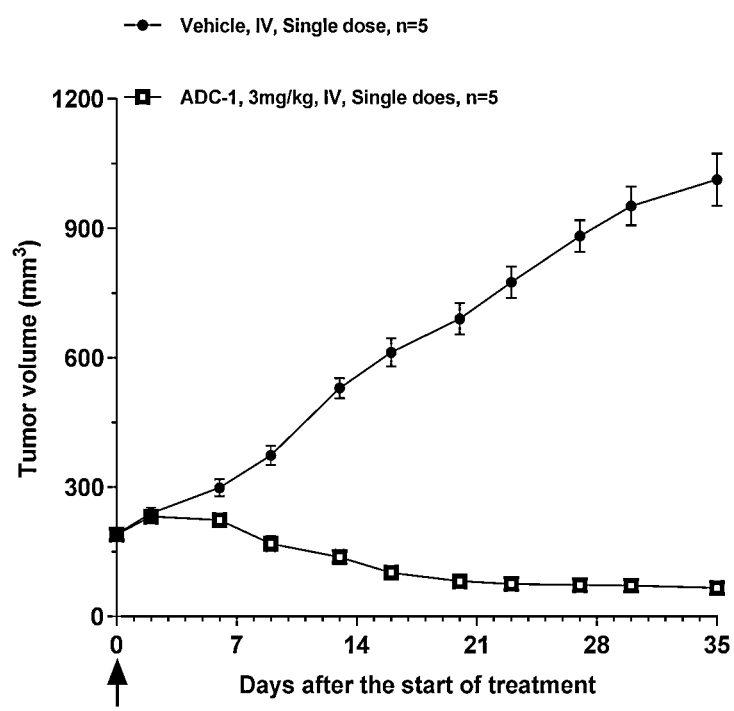
FIG. 11 shows an inhibitory effect of ADC-1 on an NCI-N87 CDX mouse model.

4) Table 4 and FIG. 11 show that ADC-1 can significantly inhibit tumor growth in the NCI-N87 CDX mouse model compared to the vehicle control group.

TABLE 4

Inhibitory Effect of ADC-1 on NCI-N87 CDX Mouse Model

| Administration Regimen | N | Tumor volume (mm$^3$)[1] on day 35 | T/C[2] (%) | TGI[3] (%) | p value[4] |
|---|---|---|---|---|---|
| Vehicle | 5 | 1013 ± 60 | — | — | — |
| ADC-1, 3 mg/kg | 5 | 67 ± 10 | 6.57 | 115.07 | <0.001 |

[1]Mean ± SEM;
[2]T/C % = $T_{RTV}$/$C_{RTV}$ × 100% ($T_{RTV}$: treatment group RTV; $C_{RTV}$: vehicle control group RTV). The relative tumor volume (RTV) was calculated according to the results of tumor measurements. The calculation formula is RTV = $V_{35}$/$V_0$, where $V_0$ is the average tumor volume measured at the time of administration to the group (i.e., $D_0$), $V_{35}$ was the average tumor volume on day 35 after administration, and $T_{RTV}$ and $C_{RTV}$ are taken from data of the same day.
[3]TGI (%) = [1 − ($T_{35}$ − $T_0$)/($V_{35}$ − $V_0$)] × 100)
[4]P value was calculated according to the tumor volume.

Example 11: Preparation and Characterization of ADC-2

See the above-mentioned preparation method for preparation of ADC-2, which differs from ADC-1 in that the linker-payload was LP-6. The characterization data of the antibody-drug conjugate ADC-2 are described below.

SDS-PAGE detection analysis of antibody-drug conjugate ADC-2: after the conjugation reaction, the purity and conjugation efficiency of ADC-2 were detected by an SDS-PAGE method. The SDS-PAGE detection results of ADC-2 show that the conjugation reaction occurs on heavy chains of an antibody in a site-specific manner, and the heavy chain of ADC-2 conjugated with the linker-payload has a significant molecular weight transition compared with a heavy chain of the monoclonal antibody with a glycan chain cutoff, which proves successful site-specific conjugation of the linker-payload onto the heavy chain of the monoclonal antibody.

The antibody unconjugated with the linker-payload is basically not observed in a conjugated product. The conjugation efficiency is up to 95% or above, and the purity of the conjugated product meets expectation.

Figure 12:
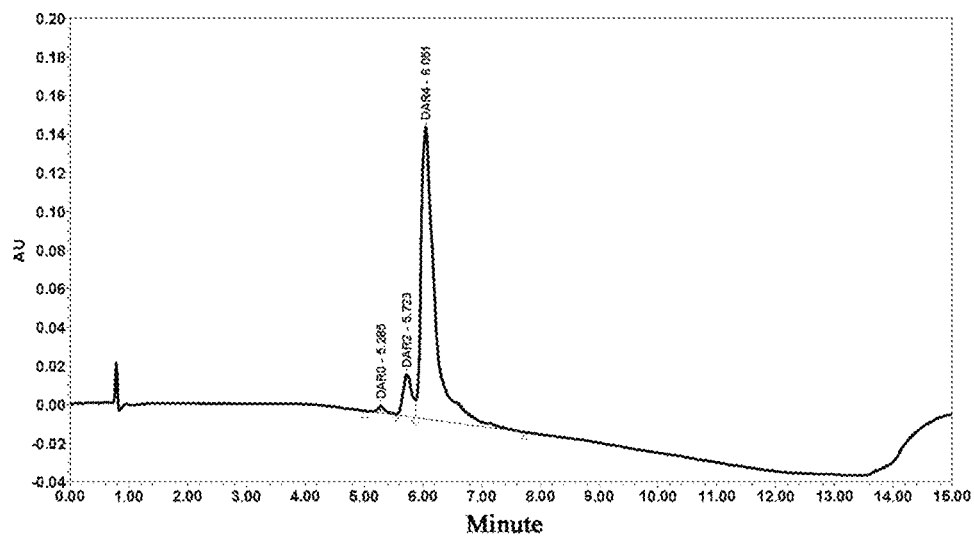
FIG. 12 shows an HIC-HPLC profile of ADC-2.

The HIC-HPLC detection analysis of ADC-2 has results as shown in FIG. 12, wherein the antibodies unconjugated with a cytotoxin are less than 5%, the conjugated product is mainly $DAR^4$, and overall, the DAR value of ADC-2 is around 3.8.

Plasma Stability Test of ADC-2
Experimental Design:

Mixed healthy human plasma (5 males and 5 females, mixed in an equal volume) was taken, and ADC-2 was added to a specific final concentration. The mixed healthy human plasma was divided into 4 portions, with 450 µL per portion, and incubated in an incubator at 37° C. The samples were collected at 0 h, 24 h, 48 h and 96 h. After the collection, the samples were stored in a refrigerator at −60° C. to −90° C. to detect the free load shedding rate and the DAR change rate.

LC-MS detection of small molecule toxins (the small molecule toxin of LP-6 involved in this example was represented by payload)

40 µL of each sample (except double blank) was taken, a certain amount of internal standard precipitant (1 ng/mL DXd) was added, and the mixture was shaken for at least 10 min; 40 µL of blank matrix was taken from the double blank and 120 µL of internal standard-free precipitant was added, and was shaken for at least 10 min, and centrifuged at 3600 g and 4° C. for 15 min. 60 µL of supernatant was pipetted into a sample injection vial, a certain amount of 0.1% FA ultrapure water was added, the mixture was shaken for at least 3 min, and HPLC detection was performed.

DAR Detection by Hybrid LC-MS Method 1 g of CNBr-activated agarose (Sigma, Cat #C9142) was weighed and put in a 50 mL centrifuge tube, and 50 mL of pre-cooled 1 mM HCl was added. The centrifuge tube was placed on a rotary mixer and incubated for at least 30 min under the incubation conditions of 4° C. and 10 RPM. Centrifugation was performed for a certain time to remove 1 mM HCl. Washed Sol once using deionized water with 5 to 10 times volume of sol, and then washed three times with 0.1 M $NaHCO_3$. An appropriate amount of $HER^2$ ECD was taken, 0.1 M $NaHCO_3$ was used to exchanged by using a 30 kD ultrafiltration tube, and then exchanged $HER^2$ ECD was mixed with packing. The mixture was placed in a rotary mixer. Incubation was performed at 25° C. and 10 RPM for 2 h±10 min, and conjugation was performed. 5 mL of 0.1 M $NaHCO_3$ buffer was then added, and centrifugation was performed for a certain time and washing was performed three times to remove unconjugated proteins. A certain amount of glycine (pH 8.0) was taken and added into packing, and the mixture was allowed to stand and block at 2° C. to 8° C. for 16 h to block unreacted chemical groups on the packing. First, the packing was washed with 5 mL of 0.1 M $NaHCO_3$ and centrifuged for a certain time, then the packing was washed with a certain amount of acetic acid buffer, and centrifuged for a certain time. The washing cycle was repeated several times. 0.1 mL of each sample was taken and put in a 1.5 mL EP tube. 0.1 mL of $HER^2$ ECD conjugated packing was added. Incubation was performed at 25° C. and 10 RPM for 2 h. Washing was performed with 1 mL of PBST three times, and centrifugation was performed for a certain time. Elution and centrifugation were performed, and supernatant was taken for concentration determination, and LC-MS detection was performed.

Result Analysis:

ADC-2 is incubated in healthy mixed human plasma for 0 h, 24 h, 48 h and 96 h, with the DAR change rates of 100.00%, 106.7%, 104.2% and 106.5%. The shedding ratios of the small molecule toxins are only 0.006%, 0.179%, 0.373% and 1.07%, respectively. The above results show that after ADC-2 is incubated at 37° C. for 96 h in the healthy mixed human plasma, its toxin shedding amount is extremely low, and DAR remains stable. Low toxin shedding indicates that the toxic side effects caused by free toxins clinically are significantly reduced, and high DAR stability indicates that the antibody molecules can target and deliver more toxin molecules to tumor sites, thereby improving the drug efficacy. The synergy of low toxin shedding and high DAR stability can significantly broaden the therapeutic window of ADC-2.

Example 13: In Vitro Activity Test of ADC-2 (in SK-BR-3, HCC1954, MDA-MB-468)

Figure 13:
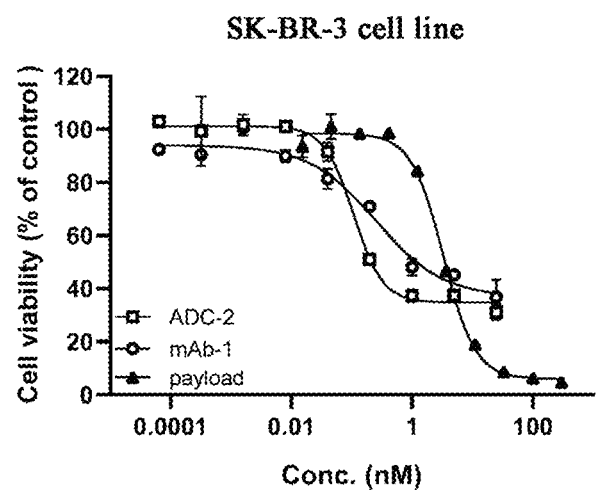
FIG. 13 shows inhibitory effect of ADC-2 and different drugs on proliferation of tumor cell SK-BR-3 (IC50, nM).
Figure 14:
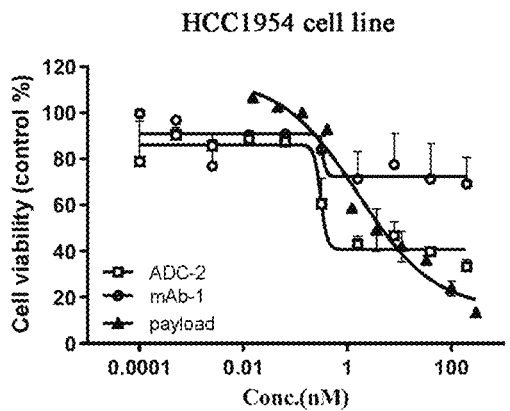
FIG. 14 shows inhibitory effect of ADC-2 and different drugs on proliferation of tumor cells HCC1954 (IC50, nM).
Figure 15:
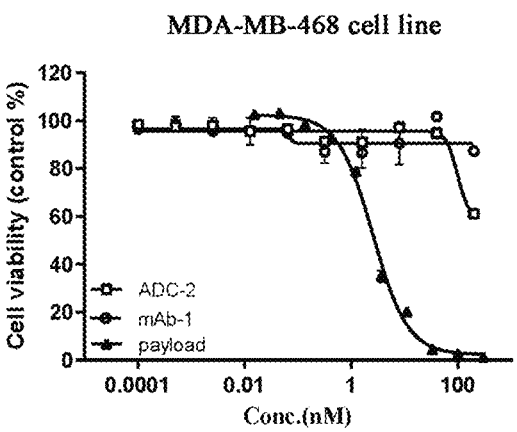
FIG. 15 shows inhibitory effect of ADC-2 and different drugs on proliferation of tumor cells MDA-MB-468 (IC50, nM).

The effect of ADC-2 on the proliferation of the tumor cell at different expression levels of ErbB2/HER2 was tested by the following methods Referring to the method described in Example 9, the antibody-drug conjugate ADC-2 was tested for its inhibitory effect on proliferation of the cancer cells at different expression levels of ErbB2/HER2. For example, ErbB2/HER2-positive human tumor cells such as SK-BR-3 and HCC1954, and ErbB2/HER2-negative human tumor cells such as MDA-MB-468 were selected. The results of the inhibitory effect of different drugs on proliferation of the tumor cells are as shown in Table 5 and FIGS. 13 to 15, wherein ADC-2 and small molecule toxins have obvious inhibitory effect on proliferation of the ErbB2/HER2-positive cells, the monoclonal antibody mAb-1 has certain inhibitory effect on proliferation of the ErbB2/HER2-positive cells, and ADC-2 is significantly superior to mAb-1. ADC-2 and monoclonal antibody mAb-1 have no inhibitory effect on proliferation of the ErbB2/HER2-negative cells, which shows good targeting performance.

TABLE 5

Inhibitory effect of Different Drugs on proliferation of Tumor Cells (IC50, nM)

| | ADC-2 | mAb-1 | Small molecule toxin |
|---|---|---|---|
| SK-BR-3 | 0.1076 | 0.2565 | 3.321 |
| HCC1954 | 0.4355 | — | 1.622 |
| MDA-MB-468 | — | — | 2.558 |

Note:
"—" undetected

Example 14: Preparation and Characterization of ADC-3

See the above-mentioned preparation method for preparation of an antibody-drug conjugate ADC-3, which differs from ADC-1 in that the antibody used was an anti-TROP2 antibody, i.e., mAb-2, and the linker-payload used was LP-6. The characterization data of the antibody-drug conjugate ADC-3 are described below.

SEC-HPLC of ADC-3 shows that the high molecular weight polymer is less than 5%, and ADC samples are mainly present in the form of monomers. The damage of the conjugation reaction to the antibody is negligible.

High-Resolution Mass Spectrometry (ESI-MS) DAR value analysis of Antibody-Drug Conjugate ADC-3

Figure 16:
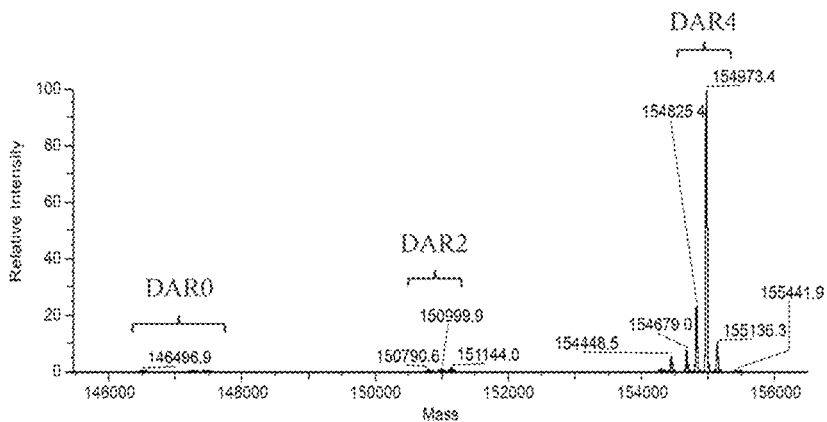
FIG. 16 shows a high-resolution mass spectrometry deconvolution diagram of ADC-3.

The molecular weight of ADC-3 was resolved by a high-resolution mass spectrometer. A deconvolved mass spectrum is shown in FIG. 16. By comparing the measured molecular weight with the theoretical molecular weight, each major molecular weight variants can be assigned. DAR value analysis was performed by using the mass spectrometry abundance of each major molecular weight variant, and its DAR value was calculated to be 3.93.

Example 15: In Vitro Activity Test of ADC-3 (BxPC-3, FaDu, HepG2)

Figure 17:
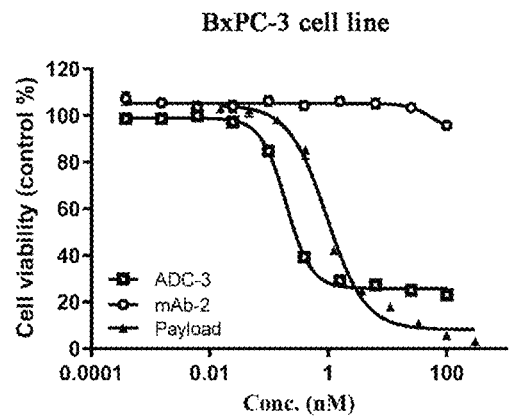
FIG. 17 shows inhibitory effect of ADC-3 and other different drugs on proliferation of tumor cells BxPC-3 (IC50, nM).
Figure 18:
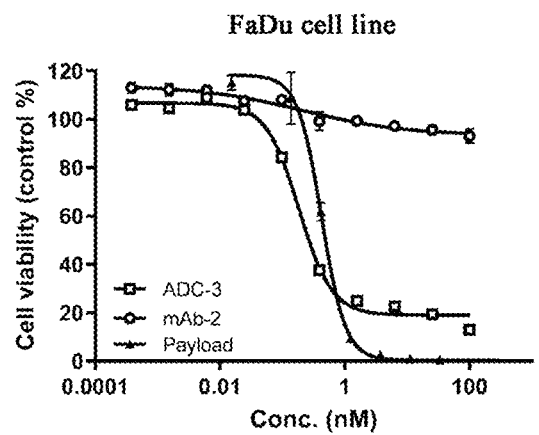
FIG. 18 shows inhibitory effect of ADC-3 and different drugs on proliferation of tumor cells FaDu (IC50, nM).
Figure 19:
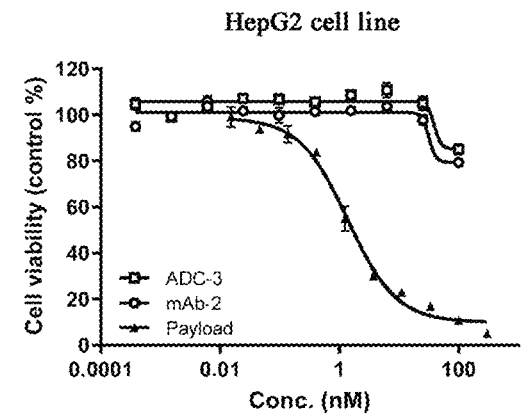
FIG. 19 shows inhibitory effect action of ADC-3 and different drugs on proliferation of tumor cells HepG2 (IC50, nM).

Referring to a similar operation of the method described in Example 9, an antibody-drug conjugate ADC-3 was tested for its inhibitory effect at different concentration gradients on proliferation of the cancer cells at different expression levels of TROP2. BxPC-3, FaDu, HepG2 and other human tumor cells were selected. The results of the inhibitory effect of different drugs on proliferation of the tumor cell are as shown in Table 6 and FIGS. 17 to 19, wherein ADC-3 and small molecule toxins have obvious inhibitory effect on proliferation of TROP2-positive cells, the TROP2 antibody, i.e., mAb-2, has no obvious inhibitory effect on the proliferation of TROP2-positive cells, and ADC-3 is significantly superior to the monoclonal antibody and the small molecule toxins. ADC-3 and monoclonal antibody mAb-2 have no inhibitory effect on the TROP2-negative cells, which shows good targeting performance.

TABLE 6

Inhibitory effect of Different Drugs on proliferation of Tumor Cells (IC50, nM)

| | $IC_{50}$ (nM) | | |
|---|---|---|---|
| | BxPC-3/TROP2 high expression | FaDu/TROP2 high expression | HepG2/TROP2 negative |
| ADC-3 | 0.1928 | 0.1839 | — |
| mAb-2 | — | — | — |
| Small molecule toxin | 0.9460 | 0.4250 | 1.383 |

Note:
"—" undetected

Example 16: In Vivo Activity Test of ADC-3 (NCI-N87 CDX Mouse Model)

Figure 20:
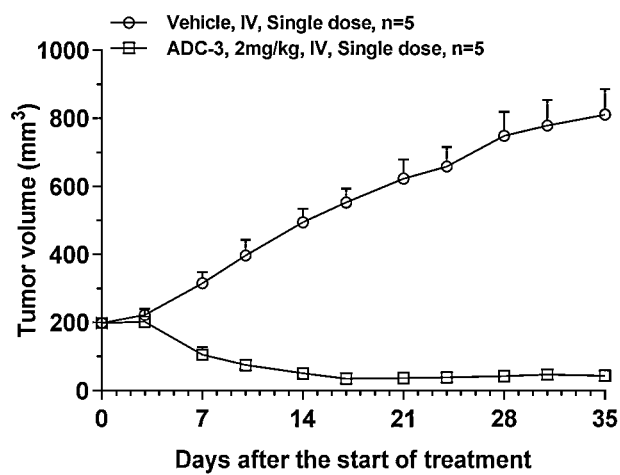
FIG. 20 shows a tumor inhibitory effect of ADC-3 on an NCI-N87 CDX mouse.
Figure 21:
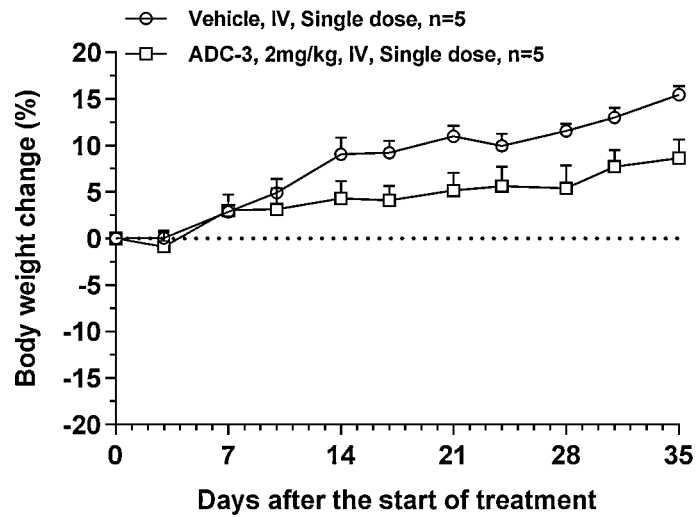
FIG. 21 shows an effect of ADC-3 on body weight of an NCI-N87 CDX mouse.

Referring to a similar method described in Example 10, the effect of ADC-3 on tumor growth inhibition method in an NCI-N87 CDX mouse model was evaluated. A tumor growth curve and a body weight change curve after administration are shown in FIGS. 20 to 21. ADC-3 shows good tumor growth inhibitory effect and good safety, and the experimental mice does not show weight loss-related toxicity.

Example 17: Preparation and Characterization of ADC-4

See the above-mentioned preparation method for preparation of an antibody-drug conjugate ADC-4, which differs from ADC-1 in that the antibody used was an anti-TROP2 antibody, i.e., mAb-2. The characterization data of the antibody-drug conjugate ADC-4 are described below.

Figure 22:
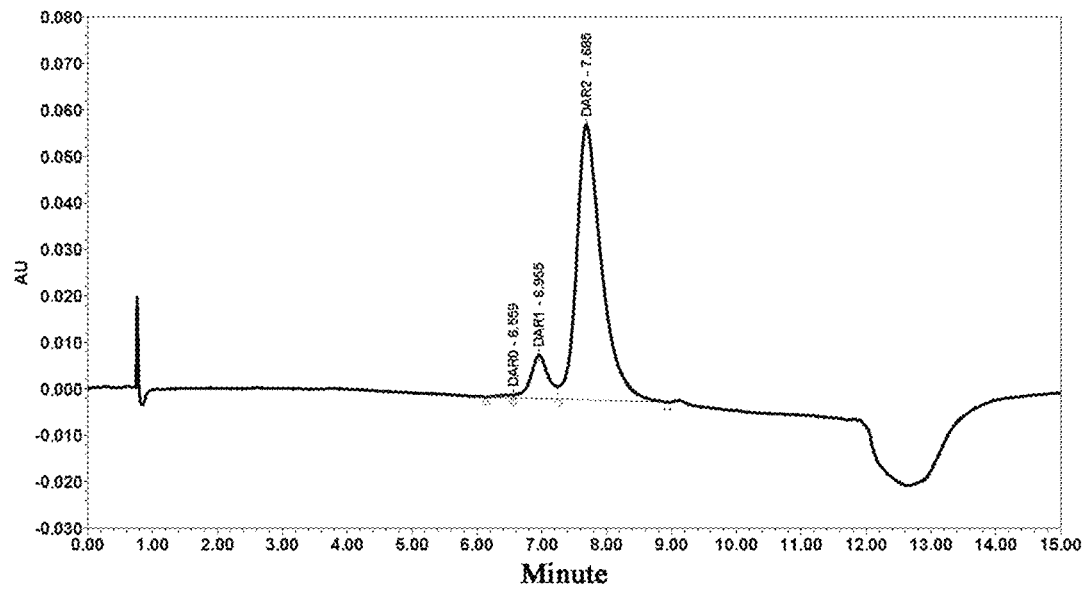
FIG. 22 is an HIC-HPLC detection analysis diagram of ADC-4.

HHIC-HPLC detection analysis of ADC-4 has detection results as shown in FIG. 22. Antibodies unconjugated with a cytotoxin are less than 5%. A conjugated product is mainly $DAR^2$, and overall, the DAR value of ADC-4 is 1.89. The SEC-HPLC detection results of ADC-4 show that the high molecular weight polymer in ADC is less than 5%, and ADC samples are mainly present in the form of monomers.

Example 18: Preparation and Characterization of ADC-5

See the above-mentioned preparation method for preparation of an antibody-drug conjugate ADC-5, which differs from ADC-1 in that the antibody used was an anti-TROP2 antibody, i.e., mAb-2, and the linker-payload used was LP-2. The characterization data of the antibody-drug conjugate ADC-5 are described below.

Figure 23:
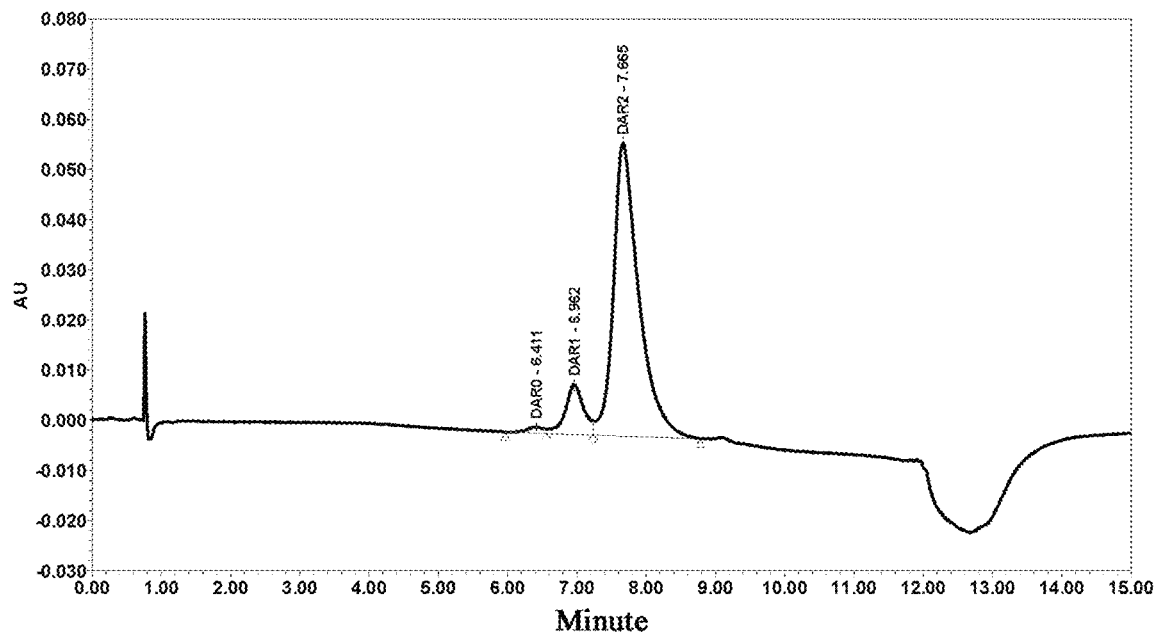
FIG. 23 is an HIC-HPLC detection analysis diagram of ADC-5.

HIC-HPLC detection analysis of ADC-5 has detection results as shown in FIG. 23. Antibodies unconjugated with a cytotoxin are less than 5%. A conjugated product is mainly $DAR^2$, and overall, the DAR value of ADC-5 is 1.87. HIC-HPLC detection of ADC-5 shows that the high molecular weight polymer in ADC is less than 5%, and ADC samples are present mainly in the form of monomers.

Example 19: In Vitro Activity Comparison of ADC-4 and ADC-5 (BxPC-3, FaDu, HepG2)

Figure 24:
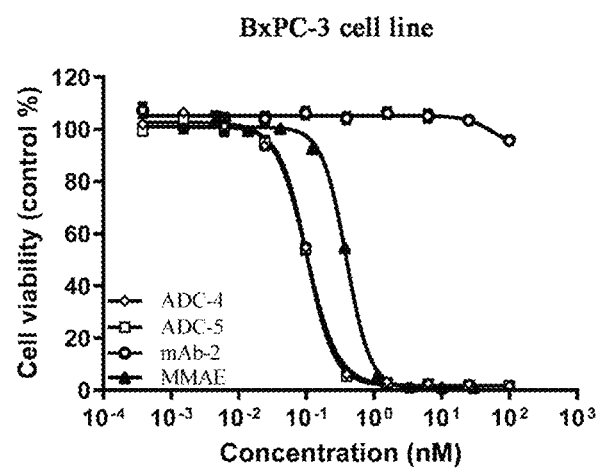
FIG. 24 shows in vitro inhibition activity of ADC-4 and ADC-5 against BxPC-3.
Figure 25:
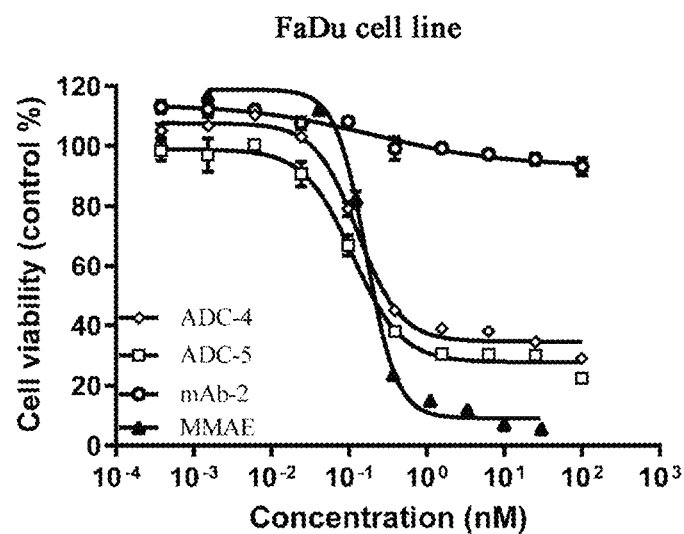
FIG. 25 shows in vitro inhibition activity of ADC-4 and ADC-5 against FaDu.
Figure 26:
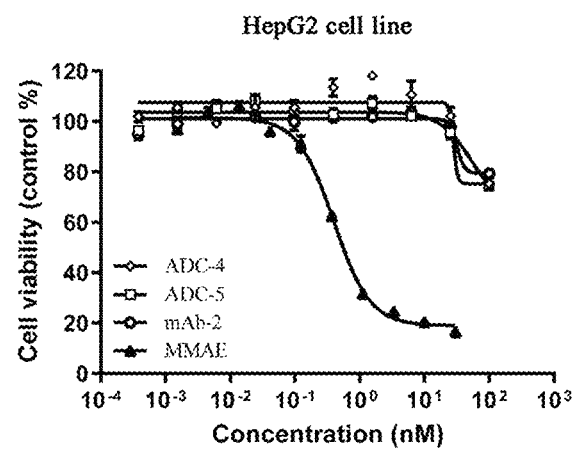
FIG. 26 shows in vitro inhibition activity of ADC-4 and ADC-5 against HepG2-3.

Referring to the method described in Example 9, the antibody-drug conjugates ADC-4 and ADC-5 were tested for its inhibitory effect on proliferation of the cancer cells at various different expression levels of TROP2. TROP2-positive human tumor cells such as BxPC-3 (human pancreatic cancer cell) and FaDu (human throat cancer cell), and TROP2-negative tumor cells such as HepG2 (human liver cancer cell) were selected. The results of the inhibitory effect of different drugs on proliferation of the tumor cells are as shown in Table 7 and FIGS. 24 to 26, wherein ADC-4, ADC-5 and MMAE small molecule toxins have obvious inhibitory effect on proliferation of the positive cells, and there is no significant difference in activity between ADC-4 and ADC-5. The monoclonal antibody has no significant inhibitory effect on proliferation of the TROP2-positive cells. ADC-4, ADC-5 and the monoclonal antibody have no inhibitory effect on proliferation of the antigen-negative cells, which shows good targeting performance.

TABLE 7

Inhibitory effect of Different Drugs on proliferation of Tumor Cells (IC50, nM)

| | ADC-4 | ADC-5 | mAb-2 | MMAE |
|---|---|---|---|---|
| BxPC-3 | 0.09995 | 0.1017 | — | 0.3878 |
| FaDu | 0.1297 | 0.1121 | — | 0.1667 |
| HepG2 | — | — | — | 0.3976 |

Note:
"—" undetected

Example 20: Preparation and Characterization of ADC-6

Figure 27:
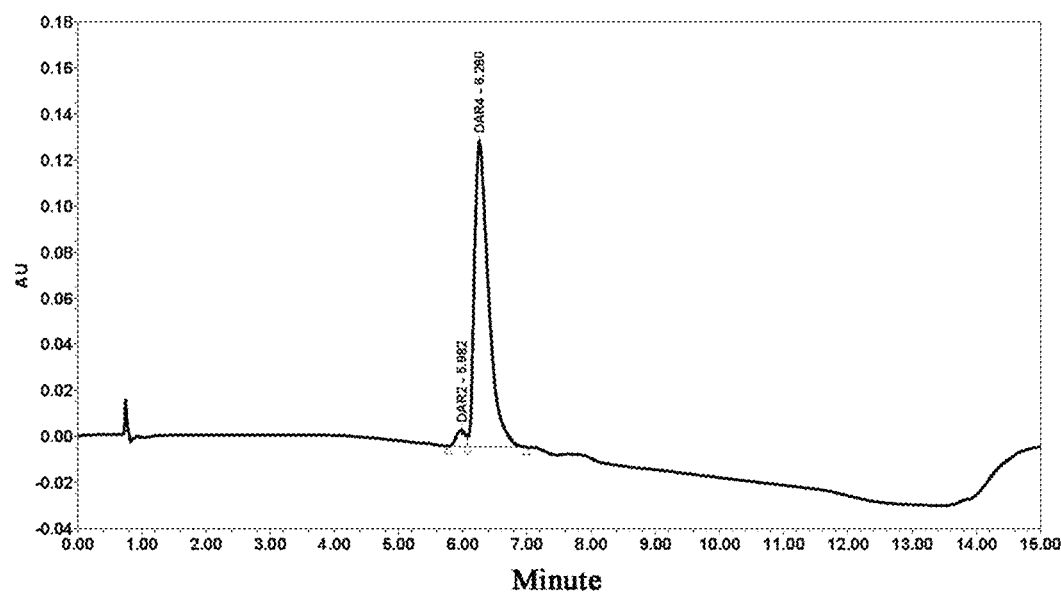
FIG. 27 shows HIC-HPLC detection analysis of ADC-6.

See the above-mentioned preparation method for preparation of an antibody-drug conjugate, which differs from ADC-1 in that the antibody used was mAb-3 (Trastuzumab), i.e., and the linker-payload used was LP-6. The characterization data of the antibody-drug conjugate ADC-6 are described below. HIC-HPLC detection analysis of ADC-6 has detection results as shown in FIG. 27. Antibodies unconjugated with a cytotoxin are less than 5%. A conjugated product is mainly DAR$^4$, and overall, the DAR value of ADC-6 is 3.93. SEC-HPLC detection of ADC-6 shows that the high molecular weight polymer in ADC is less than 5%, and ADC samples were present mainly in the form of monomers.

Example 21: In Vitro Activity Test of ADC-6 (SK-BR-3, NCI-N87)

Figure 28:
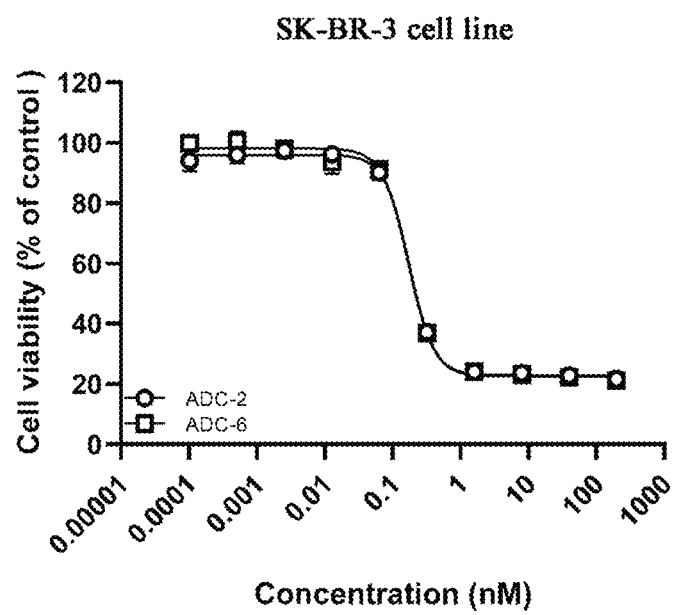
FIG. 28 shows in vitro inhibition activity of ADC-6 against SK-BR-3.
Figure 29:
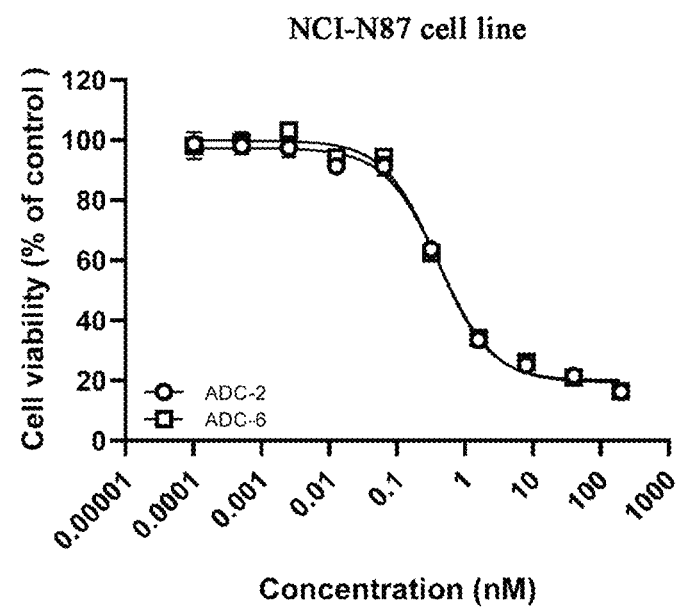
FIG. 29 shows in vitro inhibition activity of ADC-6 against NCI-N87.

Referring to the method described in Example 9, the antibody-drug conjugate ADC-6 was tested for its inhibitory effect on proliferation of the cancer cells at various different expression levels of HER2. Two groups of HER$^2$ cell lines, SK-BR-3 and NCI-N87, were selected, and activity differences between ADC-2 (with a Sortase recognition sequence) and ADC-6 (without the Sortase recognition sequence) were compared. The results show that the target ADC has no difference in terms of the cell killing activity of the above-mentioned two cell lines, with or without the recognition sequence of an Srt A enzyme (see FIGS. 28 to 29).

The sequences involved in this application are described below:

SEQ ID No: 1 (Halo-Endo S2-His):
MAEIGTGFPFDPHYVEVLGERMHYVDVGPRDGTPVLFLHGNPTSSYVWR
NIIPHVAPTHRCIAPDLIGMGKSDKPDLGYFFDDHVRFMDAFIEALGLE
EVVLVIHDWGSALGFHWAKRNPERVKGIAFMEFIRPIPTWDEWPEFARE
TFQAFRTTDVGRKLIIDQNVFIEGTLPMGVVRPLTEVEMDHYREPFLNP
VDREPLWRFPNELPIAGEPANIVALVEEYMDWLHQSPVPKLLFWGTPGV
LIPPAEAARLAKSLPNCKAVDIGPGLNLLQEDNPDLIGSEIARWLSTLE
ISGGGGGSGGGGSMDKHLLVKRTLGCVCAATLMGAALATHHDSLNTVKA
EEKTVQTGKTDQQVGAKLVQEIREGKRGPLYAGYFRTWHDRASTGIDGK
QQHPENTMAEVPKEVDILFVFHDHTASDSPFWSELKDSYVHKLHQQGTA
LVQTIGVNELNGRTGLSKDYPDTPEGNKALAAAIVKAFVTDRGVDGLDI
DIEHEFTNKRTPEEDARALNVFKEIAQLIGKNGSDKSKLLIMDTTLSVE
NNPIFKGIAEDLDYLLRQYYGSQGGEAEVDTINSDWNQYQNYIDASQFM
IGFSFFEESASKGNLWFDVNEYDPNNPEKGKDIEGTRAKKYAEWQPSTG
GLKAGIFSYAIDRDGVAHVPSTYKNRTSTNLQRHEVDNISHTDYTVSRK
LKTLMTEDKRYDVIDQKDIPDPALREQIIQQVGQYKGDLERYNKTLVLT
GDKIQNLKGLEKLSKLQKLELRQLSNVKEITPELLPESMKKDAELVMVG
MTGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEHD
ILTDFVFGTVTKRNTFIGDEEAFAIYKEGAVDGRQYVSKDYTYEAFRKD
YKGYKVHLTASNLGETVTSKVTATTDETYLVDVSDGEKVVHHMKLNIGS
GAIMMENLAKGAKVIGTSGDFEQAKKIFDGEKSDRFFTWGQTNWIAFDL
GEINLAKEWRLFNAETNTEIKTDSSLNVAKGRLQILKDTTIDLEKMDIK
NRKEYLSNDENWTDVAQMDDAKAIFNSKLSNVLSRYWRFCVDGGASSYY
PQYTELQILGQRLSNDVANTLKD*HHHHHHHHHH*

SEQ ID No: 2 (mAb-1 Light Chain):
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGECGALPETGG SEQ ID No: 3 (mAb-1 Heavy Chain):
EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSR
WGGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQ
KSLSLSPGK SEQ ID No: 4 (mAb-2 Light Chain):
DIQLTQSPSSLSASVGDRVSITCKASQDVSIAVAWYQQKPGKAPKLLIY
SASYRYTGVPDRFSGSGSGTDFTLTISSLQPEDFAVYYCQQHYITPLTF
GAGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGECGALPETGG SEQ ID No: 5 (mAb-2 Heavy Chain):
QVQLQQSGSELKKPGASVKVSCKASGYTFTNYGMNWVKQAPGQGLKWMG
WINTYTGEPTYTDDFKGRFAFSLDTSVSTAYLQISSLKADDTAVYFCAR
GGFGSSYWYFDVWGQGSLVTVSSASTKGPSVFPLAPSSKSTSGGTAALG
CLVKDYFPEPVTVSWNSGALTSGVHTFPAVLQSSGLYSLSSVVTVPSSS
LGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYT
QKSLSLSPGK SEQ ID No: 6 (mAb-3 Light Chain):
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID No: 7 (mAb-3 Heavy Chain):
EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSR -continued

```
WGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK
```

The applicant declares that the detailed methods of the present disclosure are illustrated with the foregoing embodiments in the present disclosure, but the present disclosure is not limited to the foregoing detailed methods, which does not mean that the present disclosure can be implemented only by relying on the foregoing detailed methods. Those skilled in the art should know that any improvement to the present disclosure, the equivalent substitution of each raw material of the product of the present disclosure and the addition of auxiliary ingredients, the selection of specific methods, and the like all fall within the scope of protection and disclosure of the present disclosure.

The invention claimed is:

1. A method for preparing an antibody-drug conjugate, wherein the antibody-drug conjugate is subjected to site-specific conjugation, based on an N-glycosylation site in an Fc region, and the method comprises the steps of:
   (1) providing a donor containing an oxazoline oligosaccharide, a protein containing the Fc region, and an immobilized endoglycosidase with glycosyltransferase activity; wherein the Fc contains a GlcNAc motif, wherein the GlcNAc motif is a glycan chain with N-acetylglucose-B-(1, 4)-N-acetylglucose; and
   (2) covalently attaching the donor containing the oxazoline oligosaccharide to the protein containing the Fc region under the catalysis of the endoglycosidase,
   wherein the donor containing the oxazoline oligosaccharide is a linker-payload compound of formula (I):

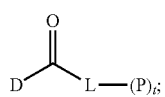

wherein P is a payload;
   wherein D is the oxazoline oligosaccharide, wherein the oxazoline oligosaccharide has the following structure: first hexosyl derivative-(second hexosyl)$_f$-β-D-glucopyranosyloxazoline, wherein carbon at position 6 of the first hexosyl derivative is in the form of—C(O)-; f is 0, 1, 2, 3, 4, 5 or 6; the β-D-glucopyranosyloxazoline has the following structure:

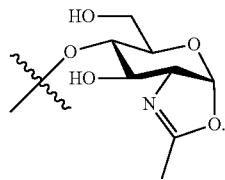

wherein L is a linker end, L is directly attached to carbonyl in D-C(O)-via-NH-therein, and the carbon at position 6 of the first hexosyl derivative in the form of—C(O)—is the same carbon in D-C(O) in formula (I),
   wherein when L is an unbranched linker end, L is attached to one P, and t is 1; while when L is a branched linker end, each branch can be attached to one P, and t is an integer greater than 1, wherein the protein containing the Fc region is an antibody or an antigen-binding fragment thereof.

2. The method according to claim 1, wherein the protein containing the Fc region is an antibody.

3. The method according to claim 1, wherein the first hexosyl derivative is selected from glucosyl, mannosyl, galactosyl, fructosyl, gulosyl, and idosyl with carbon at position 6 of the first hexosyl in the form of —C(O)—; and/or
   the second hexosyl, at each occurrence, is independently selected from glucosyl, mannosyl, galactosyl, and fructosyl; and/or
   individual monosaccharide moieties in an oligosaccharide structure are attached by β-(1→4) glycosidic bonds.

4. The method according to claim 1, wherein the oxazoline oligosaccharide has the following structure: first hexosyl derivative-B-D-glucopyranosyloxazoline, and wherein the first hexosyl derivative is mannosyl with carbon at position 6 in the form of —C(O)—; or the oxazoline oligosaccharide has the following structure: first hexosyl derivative-β-D-glucopyranosyloxazoline, and wherein the first hexosyl or its derivative is galactosyl with carbon at position 6 in the form of -C(O)-; or the oxazoline oligosaccharide has the following structure: first hexosyl derivative-β-D-glucopyranosyloxazoline, and wherein the first hexosyl derivative is glucosyl with carbon at position 6 in the form of -C(O)-; or the oxazoline oligosaccharide has the following structure: first hexosyl derivative-β-D-glucopyranosyloxazoline, and wherein the first hexosyl derivative is fructosyl with carbon at position 6 in the form of -C(O)-; or the oxazoline oligosaccharide has the following structure: first hexosyl derivative-β-D-glucopyranosyloxazoline, and wherein the first hexosyl derivative is gulosyl with carbon at position 6 in the form of -C(O)-; or the oxazoline oligosaccharide has the following structure: first hexosyl derivative-β-D-glucopyranosyloxazoline, and wherein the first hexosyl derivative is idosyl with carbon at position 6 in the form of -C(O)-.

5. The method according to claim 1, wherein the oxazoline oligosaccharide has the structure below:

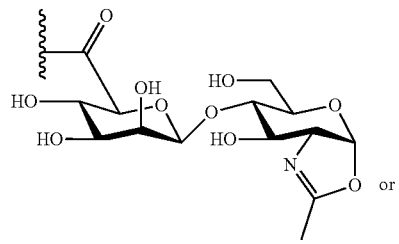 or

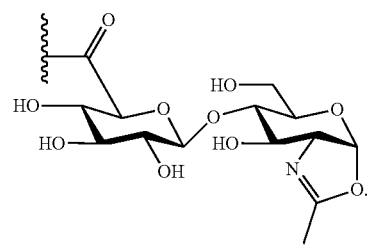

6. The method according to claim 1
wherein the antibody-drug conjugate has a structure as shown in formula (II):

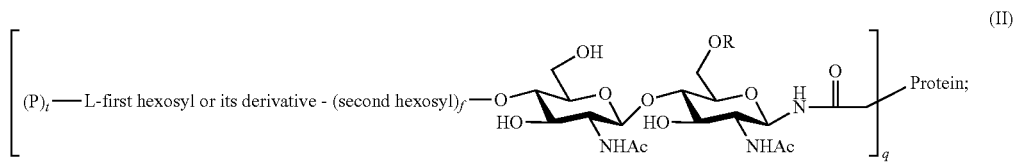

R is hydrogen or α-L-fucosyl;
q is 1 or 2; and
Protein is the antibody or the antigen-binding fragment thereof.

7. The method according to claim 6,
wherein the antibody-drug conjugate has a structure as shown in formula (II-1), (II-2), (II-3), (II-4) or (II-5):

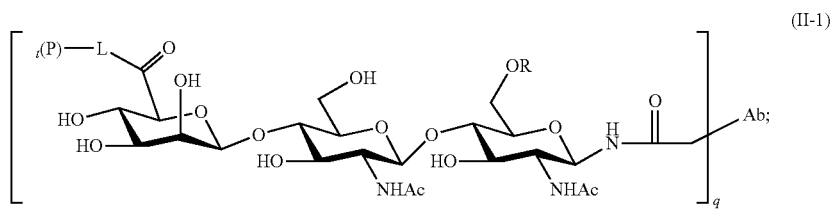

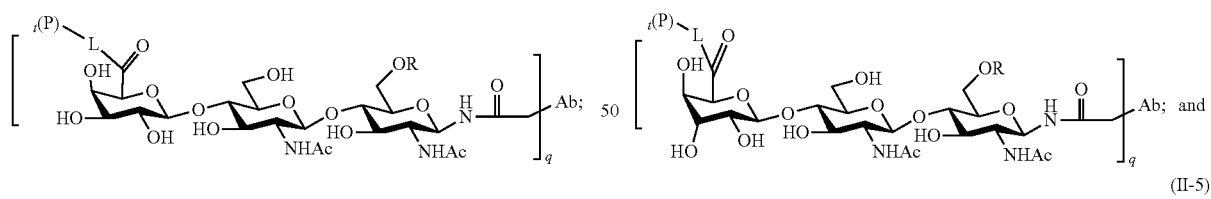

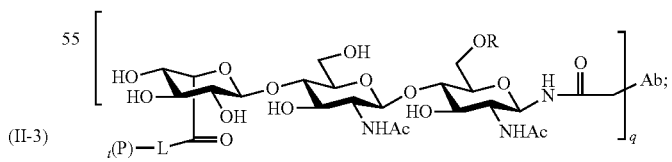

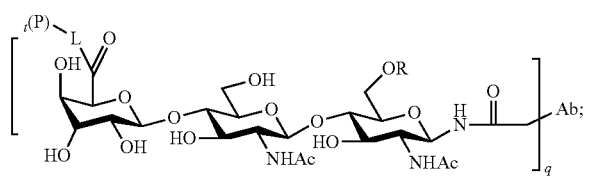

R is hydrogen or α-L-fucosyl;
q is 1 or 2; and
Ab is the antibody or the antigen-binding fragment thereof.

8. The method of claim 7 wherein the antibody-drug conjugate has a structure as shown in formula (II-1):

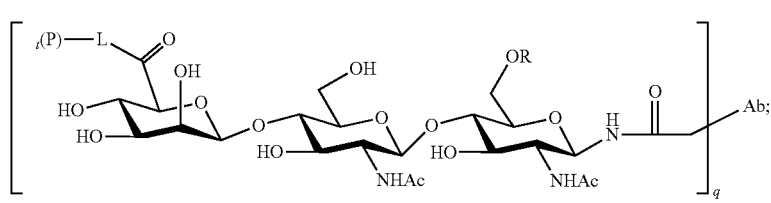

and

D-C(O)— is a disaccharide structure

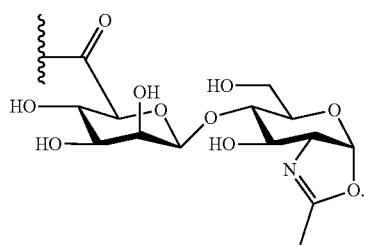

9. The method according to claim 1, wherein -L-(P)$_t$ is -L$^2$-L$^1$-B-P, that is, formula (I) is:

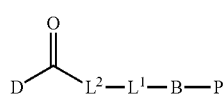

wherein

B is independently absent, or is 1) below, or 2) below, or a combination of 1) and 2) below: 1) A self-immolative spacer Sp1; 2) a divalent group, or a combination of two or more divalent groups, wherein the divalent group is selected from: -CR$^1$R$^2$-, C$_{1-10}$ alkylene, C$_{4-10}$ cycloalkylene, C$_{4-10}$ heterocyclylene and —(CO)-;

L$^1$ is independently absent, or is an uncleavable sequence; or is a cleavable sequence comprising an amino acid sequence that is enzymatically cleavable, and the amino acid sequence that is enzymatically cleavable comprises 1, 2, 3, 4, 5, 6, 7, 8, 9 or 10 amino acids;

L$^2$ is independently absent; or is 1) below; or 2) below; or a combination of 1) and 2) below:

1) -NH-C$_{2-20}$ alkylene, wherein one or more -CH$_2$- structures in the alkylene are optionally replaced by the following groups: -CR$^3$R$^4$-, -O-, -(CO)-, -S-, -S(=O)$_2$-, -NR$^5$-, -NR$^\oplus$R$^6$R$^7$-, C$_{4-10}$ cycloalkylene, C$_{4-10}$ heterocyclylene and phenylene, wherein the cycloalkylene, the heterocyclylene and the phenylene are each independently unsubstituted or substituted with at least one substituent selected from halogen, -C$_{1-10}$ alkyl, -C$_{1-10}$ haloalkyl, -C$_{1-10}$ alkylene-NH-R$^8$ and —C$_{1-10}$ alkylene-O-R$^9$;

2) an amino acid residue sequence, i.e., -*(AA)$_n$**-, wherein n is an integer from 1, 2, 3, 4, 5, 6, 7, 8, 9 or 10 to 100, AA, at each occurrence, is independently an amino acid residue, * represents an N-terminus of a corresponding amino acid, ** represents a C-terminus of the corresponding amino acid, and -(C$_2$H$_4$-O)$_m$-(CH$_2$)$_p$— is optionally present between amino and α-carbon of an amino acid, wherein m is 1, 2, 3, 4, 5, 6, 7, 8, 9 or 10; p is 0, 1, 2 or 3, and a * terminus forms an amide bond with the carbonyl in the disaccharide structure;

R$^1$, R$^2$, R$^3$, R$^4$, R$^5$, R$^6$, R$^7$, R$^8$ and R$^9$ are each independently selected from hydrogen, halogen, substituted or unsubstituted -C$_{1-10}$ alkyl, and C$_{4-10}$ cycloalkylene; or R$^1$ and R$^2$ and carbon atoms attached thereto together form a 3 to 6-membered cycloalkylene, and/or R$^3$ and R$^4$ and carbon atoms attached thereto together form a 3 to 6-membered cycloalkylene;

P is a payload attached to moiety B, or moiety L$^1$, or moiety L$^2$.

10. The method according to claim 1, wherein -L-(P) t is

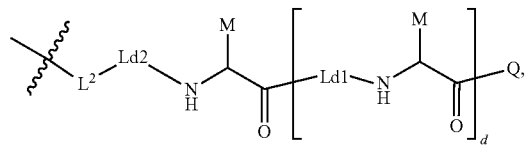

that is, formula (I) is:

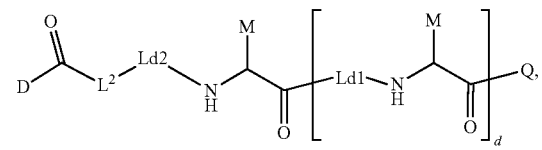

wherein

Ld2 and each Ld1 are independently bonds, or are selected from —NH—C$_{1-20}$ alkylene-(CO)— and —NH-(PEG)$_i$-(CO)—, or are natural amino acids independently unsubstituted or substituted with —CO—(PEG)$_j$-R$^{11}$ on a side chain or oligomeric natural amino acids with a polymerization degree of 2 to 10 (i.e., 2, 3, 4, 5, 6, 7, 8, 9 or 10); R$^{11}$ is C$_{1-10}$ alkyl;

d is 0, 1, 2, 3, 4, 5 or 6;

(PEG)$_i$- and -(PEG)$_j$- are each a PEG fragment, comprising a specified number of continuous —(O—C$_2$H$_4$)- structural units or continuous —(C$_2$H$_4$—O)— structural units, optionally with C$_{1-10}$ alkylene attached at one end; each i is independently an integer from 1 to 100, and each j is independently an integer from 1 to 100;

M is hydrogen or LKa-L$^2$-L$^1$-B-P;

Q is NH$_2$ or L$^2$-L$^1$-B-P;

provided that the following cases are excluded: M is hydrogen and Q is NH$_2$;

each LKa is independently selected from

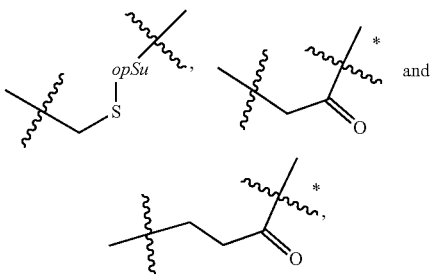

opSu is

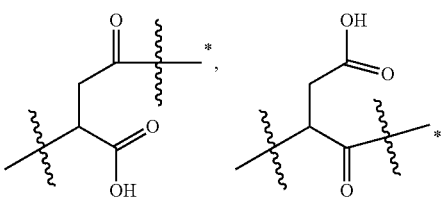 [SMILES: *C(=O)CC(*)C(=O)O ; *C(=O)C(*)CC(=O)O]

or a mixture thereof, wherein * represents a moiety attached to $L^2$;

B is independently absent, or is 1) below, or 2) below, or a combination of 1) and 2) below: 1) A self-immolative spacer Sp1; 2) a divalent group, or a combination of two or more divalent groups, wherein the divalent group is selected from: -$CR^1R^2$-, $C_{1-10}$ alkylene, $C_{4-10}$ cycloalkylene, $C_{4-10}$ heterocyclylene and —(CO)-;

L' is independently absent, or is an uncleavable sequence; or is a cleavable sequence comprising an amino acid sequence that is enzymatically cleavable, and the amino acid sequence that is enzymatically cleavable comprises 1, 2, 3, 4, 5, 6, 7, 8, 9 or 10 amino acids;

$L^2$ is independently absent; or is 1) below; or 2) below; or a combination of 1) and 2) below:

1) -NH-$C_{2-20}$ alkylene, wherein one or more-$CH_2$-structures in the alkylene are optionally replaced by the following groups:—$CR^3R^4$-, -O-, —(CO)-, -S-, -S(=O)$_2$-, -$NR^5$-, -$N^{\oplus}R^6R^7$-, $C_{4-10}$ cycloalkylene, $C_{4-10}$ heterocyclylene and phenylene, wherein the cycloalkylene, the heterocyclylene and the phenylene are each independently unsubstituted or substituted with at least one substituent selected from halogen, -$C_{1-10}$ alkyl, -$C_{1-10}$ haloalkyl, -$C_{1-10}$ alkylene-NH-$R^8$ and —$C_{1-10}$ alkylene -O-$R^9$;

2) an amino acid residue sequence, i.e., -*(AA)$_n$**-, wherein n is an integer from 1, 2, 3, 4, 5, 6, 7, 8, 9 or 10 to 100, AA, at each occurrence, is independently an amino acid residue, * represents an N-terminus of a corresponding amino acid, ** represents a C-terminus of the corresponding amino acid, and —($C_2H_4$-O)$_m$—($CH_2$)$_p$- is optionally present between amino and α-carbon of an amino acid, wherein m is 1, 2, 3, 4, 5, 6, 7, 8, 9 or 10; p is 0, 1, 2 or 3, and a * terminus forms an amide bond with the carbonyl in the disaccharide structure;

$R^1$, $R^2$, $R^3$, $R^4$, $R^5$, $R^6$, $R^7$, $R^8$ and $R^9$ are each independently selected from hydrogen, halogen, substituted or unsubstituted -$C_{1-10}$ alkyl, and $C_{4-10}$ cycloalkylene; or $R^1$ and $R^2$ and carbon atoms attached thereto together form a 3 to 6-membered cycloalkylene, and/or $R^3$ and $R^4$ and carbon atoms attached thereto together form a 3 to 6-membered cycloalkylene;

P is a payload attached to moiety B, or moiety $L^1$, or moiety $L^2$.

11. The method according to claim 9, wherein $L^2$ is the amino acid residue sequence, i.e., -*(AA)$_n$**-, wherein n is an integer from 1 to 100, AA, at each occurrence, is independently an amino acid residue, * represents the N-terminus of the corresponding amino acid, ** represents the C-terminus of the corresponding amino acid, and —($C_2H_4$-O)$_m$—($CH_2$)$_p$—is optionally present between the amino and the α-carbon of the amino acid, wherein m is 1, 2, 3, 4, 5, 6, 7, 8, 9 or 10; p is 0, 1, 2 or 3, and the * terminus forms the amide bond with the carbonyl in the disaccharide structure.

12. The method according to claim 1, wherein the endoglycosidase with the glycosyltransferase activity is N-acetyl glucosamine endohydrolase, optionally wherein the N-acetyl glucosamine endohydrolase comprises at least one of Endo-S(*Streptococcus pyogenes* endoglycosidase-S), Endo F3 (*Elizabethkingia miricola* endoglycosidase-F3), Endo S2 (Endoglycosidase-S2, *S. pyogenes* endoglycosidase-S2), Endo Sd (Endoglycosidase-Sd, *S. pyogenes* endoglycosidase-Sd) and Endo CC (Endoglycosidase-CC, *S. pyogenes* endonuclease-CC); or the N-acetyl glucosamine endohydrolase comprises at least one of Endo H, Endo D, Endo F2, Endo F3, Endo M, Endo CC1, Endo CC2, Endo Om, Endo S and Endo S2.

13. The method according to claim 1, wherein the endoglycosidase with the glycosyltransferase activity is covalently attached to a Halo tag, and is immobilized on a support containing haloalkyl linker via the Halo tag, and the Halo tag is a dehalogenase or its variant or truncated functional active moiety, optionally wherein one end of the endoglycosidase is covalently attached to the Halo tag, and the other end is covalently attached to a His tag; or an amino end of the endoglycosidase is covalently attached to the Halo tag, and a carboxyl end is covalently attached to the His tag, i.e., Halo-endoglycosidase-His; or the amino end of the endoglycosidase is attached to the Halo tag, the carboxyl end is attached to the His tag, and the endoglycosidase is Endo-S2, i.e., Halo-Endo S2-His.

14. The method according to claim 13, wherein the support comprises a chloroalkyl linker, such that the endoglycosidase is immobilized on the support under the covalent interaction between the chloroalkyl linker and the Halo tag, optionally wherein the chloroalkyl linker is generated by a chloroalkyl substrate with a structure of formula (III):

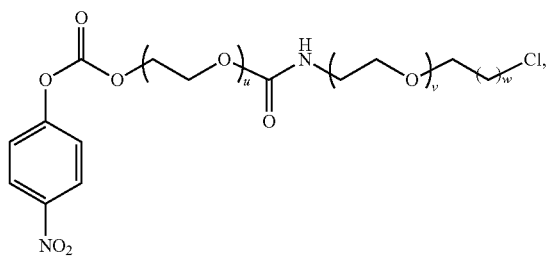

wherein u is an integer from 1 to 20, v is an integer from 0 to 20, and w is an integer from 1 to 19.

15. The method according to claim 13, wherein the support has a structure of formula (IV):

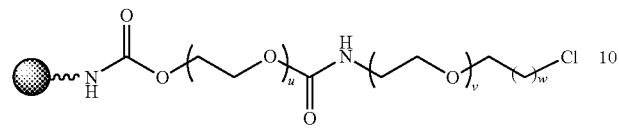

(IV)

wherein u is an integer from 1 to 20, v is an integer from 0 to 20, and w is an integer from 1 to 19;

◯ is resin, a bead, a membrane, gel, a matrix, a film, a plate, a well, a tube, a glass slide or a surface.

16. The method according to claim 15, wherein the resin is selected from agarose resin, silicone resin, polymethyl methacrylate resin and cellulose resin.

17. The method according to claim 15, wherein the resin is highly cross-linked agarose resin or polymethyl methacrylate resin.

* * * * *

SEQUENCE LISTING

```
Sequence total quantity: 7
SEQ ID NO: 1              moltype = AA   length = 1160
FEATURE                   Location/Qualifiers
source                    1..1160
                          mol_type = protein
                          organism = synthetic construct
REGION                    1..1160
                          note = Halo-Endo S2-His
SEQUENCE: 1
MAEIGTGFPF DPHYVEVLGE RMHYVDVGPR DGTPVLFLHG NPTSSYVWRN IIPHVAPTHR    60
CIAPDLIGMG KSDKPDLGYF FDDHVRFMDA FIEALGLEEV VLVIHDWGSA LGFHWAKRNP   120
ERVKGIAFME FIRPIPTWDE WPEFARETFQ AFRTTDVGRK LIIDQNVFIE GTLPMGVVRP   180
LTEVEMDHYR EPFLNPVDRE PLWRFPNELP IAGEPANIVA LVEEYMDWLH QSPVPKLLFW   240
GTPGVLIPPA EAARLAKSLP NCKAVDIGPG LNLLQEDNPD LIGSEIARWL STLEISGGGG   300
GSGGGGSMDK HLLVKRTLGC VCAATLMGAA LATHHDSLNT VKAEEKTVQT GKTDQQVGAK   360
LVQEIREGKR GPLYAGYFRT WHDRASTGID GKQQHPENTM AEVPKEVDIL FVFHDHTASD   420
SPFWSELKDS YVHKLHQQGT ALVQTIGVNE LNGRTGLSKD YPDTPEGNKA LAAAIVKAFV   480
TDRGVDGLDI DIEHEFTNKR TPEEDARALN VFKEIAQLIG KNGSDKSKLL IMDTTLSVEN   540
NPIFKGIAED LDYLLRQYYG SQGGEAEVDT INSDWNQYQN YIDASQFMIG FSFFEESASK   600
GNLWFDVNEY DPNNPEKGKD IEGTRAKKYA EWQPSTGGLK AGIFSYAIDR DGVAHVPSTY   660
KNRTSTNLQR HEVDNISHTD YTVSRKLKTL MTEDKRYDVI DQKDIPDPAL REQIIQQVGQ   720
YKGDLERYNK TLVLTGDKIQ NLKGLEKLSK LQKLELRQLS NVKEITPELL PESMKKDAEL   780
VMVGMTGLEK LNLSGLNRQT LDGIDVNSIT HLTSFDISHN SLDLSEKSED RKLLMTLMEQ   840
VSNHQKITVK NTAFENQKPK GYYPQTYDTK EGHYDVDNAE HDILTDFVFG TVTKRNTFIG   900
DEEEAFAIYKE GAVDGRQYVS KDYTYEAFRK DYKGYKVHLT ASNLGETVTS KVTATTDETY   960
LVDVSDGEKV VHHMKLNIGS GAIMMENLAK GAKVIGTSGD FEQAKKIFDG EKSDRFFTWG  1020
QTNWIAFDLG EINLAKEWRL FNAETNTEIK TDSSLNVAKG RLQILKDTTI DLEKMDIKNR  1080
KEYLSNDENW TDVAQMDDAK AIFNSKLSNV LSRYWRFCVD GGASSYYPQY TELQILGQRL  1140
SNDVANTLKD HHHHHHHHH                                              1160

SEQ ID NO: 2              moltype = AA   length = 222
FEATURE                   Location/Qualifiers
source                    1..222
                          mol_type = protein
                          organism = synthetic construct
REGION                    1..222
                          note = mAb-1 Light chain
SEQUENCE: 2
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGALPET GG                     222

SEQ ID NO: 3              moltype = AA   length = 450
FEATURE                   Location/Qualifiers
```

```
                        -continued
source              1..450
                    mol_type = protein
                    organism = synthetic construct
REGION              1..450
                    note = mAb-1 Heavy chain
SEQUENCE: 3
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 4        moltype = AA  length = 222
FEATURE             Location/Qualifiers
source              1..222
                    mol_type = protein
                    organism = synthetic construct
REGION              1..222
                    note = mAb-2 Light chain
SEQUENCE: 4
DIQLTQSPSS LSASVGDRVS ITCKASQDVS IAVAWYQQKP GKAPKLLIYS ASYRYTGVPD    60
RFSGSGSGTD FTLTISSLQP EDFAVYYCQQ HYITPTFGSA GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGALPET GG                      222

SEQ ID NO: 5        moltype = AA  length = 451
FEATURE             Location/Qualifiers
source              1..451
                    mol_type = protein
                    organism = synthetic construct
REGION              1..451
                    note = mAb-2 Heavy chain
SEQUENCE: 5
QVQLQQSGSE LKKPGASVKV SCKASGYTFT NYGMNWVKQA PGQGLKWMGW INTYTGEPTY    60
TDDFKGRFAF SLDTSVSTAY LQISSLKADD TAVYFCARGG FGSSYWYFDV WGQGSLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 6        moltype = AA  length = 214
FEATURE             Location/Qualifiers
source              1..214
                    mol_type = protein
                    organism = synthetic construct
REGION              1..214
                    note = mAb-3 Light chain
SEQUENCE: 6
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 7        moltype = AA  length = 450
FEATURE             Location/Qualifiers
source              1..450
                    mol_type = protein
                    organism = synthetic construct
REGION              1..450
                    note = mAb-3 Heavy chain
SEQUENCE: 7
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450
```